(12) United States Patent
Zimmermann et al.

(10) Patent No.: US 7,867,992 B2
(45) Date of Patent: *Jan. 11, 2011

(54) SUBSTITUTED QUINOLONES

(75) Inventors: Holger Zimmermann, Wuppertal (DE); Rudolf Schohe-Loop, Wuppertal (DE); Kerstin Henninger, Wuppertal (DE); Dieter Lang, Velbert (DE); Kai Thede, Berlin (DE); Chantal Fuerstner, Muelheim An der Ruhr (DE); David Brueckner, Essen (DE); Daniela Paulsen, Wuppertal (DE); Thomas Roelle, Leverkusen (DE); Johannes Koebberling, Grevenbroich (DE); Marcus Bauser, Berlin (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 334 days.

This patent is subject to a terminal disclaimer.

(21) Appl. No.: 11/655,589

(22) Filed: Jan. 19, 2007

(65) Prior Publication Data

US 2007/0293478 A1 Dec. 20, 2007

Related U.S. Application Data

(63) Continuation of application No. PCT/EP2005/007601, filed on Jul. 13, 2005.

(30) Foreign Application Priority Data

Jul. 21, 2004 (DE) ........................ 10 2004 035 203

(51) Int. Cl.
A01N 43/62 (2006.01)
A61K 31/55 (2006.01)
C07D 413/00 (2006.01)
(52) U.S. Cl. ........................ 514/183; 514/218; 544/121
(58) Field of Classification Search ................ 514/183, 514/218; 544/121
See application file for complete search history.

(56) References Cited

U.S. PATENT DOCUMENTS

| 4,908,366 | A | 3/1990 | Schriewer et al. |
| 4,959,363 | A | 9/1990 | Wentland |
| 5,051,418 | A | 9/1991 | Schriewer et al. |
| 6,995,262 | B1 | 2/2006 | Deroover et al. |
| 7,141,565 | B1 | 11/2006 | Whitten et al. |
| 7,569,563 | B2 | 8/2009 | Schohe-Loop et al. |
| 2007/0293478 | A1 | 12/2007 | Zimmermann et al. |

FOREIGN PATENT DOCUMENTS

| CA | 2115021 A1 | 8/1994 |
| DE | 34 20 743 | 12/1985 |
| DE | 199 37 024 | 2/2001 |
| EP | 0 241 206 | 10/1987 |
| EP | 0 276 700 | 8/1988 |
| EP | 0 352 123 | 1/1990 |
| EP | 0 612 731 | 8/1994 |
| GB | 932487 A | 7/1963 |
| WO | WO-96/01262 | 1/1996 |
| WO | WO-97/04775 | 2/1997 |
| WO | WO-97/04779 | 2/1997 |
| WO | WO-00/40561 | 7/2000 |
| WO | WO-02/09758 | 2/2002 |
| WO | WO-02/26713 | 4/2002 |
| WO | WO-02/085886 | 10/2002 |
| WO | WO-03/031397 A1 | 4/2003 |
| WO | WO-03/050107 | 6/2003 |
| WO | WO-2006/008046 A1 | 1/2006 |
| WO | WO-2007/003308 A1 | 1/2007 |

OTHER PUBLICATIONS

STN accession No. 2004147650 corresponding to compound CAS# 371216-54-5.*
Patani et. al., Chem. Rev. (1996) 96:3147-3176.*
Dorwald F. A. (Side reactions in organic synthesis, 2005, Wiley, VCH, Weinheim, p. IX of Preface).*
Drug Evaluations 6th Edition (1986) pp. 1615-1627.*
Alvernhe et al., J. Org. Chem. (1981) 46:4938-4948.
Chong et al., Abstracts of the 39th Interscience Conference on Antimicrobial Agents and Chemotherapy (1999) p. 439.
Cinatl Jr. et al., FEMS Microbiology Reviews (2004) 28:59-77.
Cowden et al., Tetrahedron Letters (2000) 41:8661-8664.
Da Silva et al., Current Medicinal Chemistry (2003) 10:21-39.
Database Chemicals 'Online! Chemical Abstracts Service, Columbus, Ohio, Jan. 1, 2004, Accession No. 2003:1549264, CAS Registry No. 384803-97-8.
International Search Report for PCT/EP2005/007601, mailed on Oct. 21, 2005, 3 pages.
Kimura et al., J. Med. Chem. (1994) 37:3344-3352.
Sanchez et al., J. Med. Chem. (1995) 38:4478-4487.
Translation of the International Preliminary Report on Patentability for PCT/EP2005/007601, mailed Feb. 15, 2007, 7 pages.
Written Opinion of the International Searching Authority for PCT/EP2005/007601, Jan. 21, 2007, 5 pages.
Caroon et al., *J. Med. Chem.*, 24:1320-1328 (1981).
Chiu et al., *J. Pharmacol. Sci.*, 95:311-319 (2004).
Drug Evaluations by American Medical Association, 6th Ed., pp. 1615-1627 (1986).
McGuirk et al., *J. Med. Chem.*, 35(4):611-620 (1992).
Smith et al., *J. Med. Chem.*, 38(19):3772-3779 (1995).
International Preliminary Report on Patentability for Application No. PCT/EP2007/000923, dated Nov. 6, 2008.
International Search Report and Written Opinion for Application No. PCT/EP2007/000923, dated Sep. 12, 2007.

* cited by examiner

*Primary Examiner*—Brandon J Fetterolf
*Assistant Examiner*—Marcos Sznaidman
(74) *Attorney, Agent, or Firm*—Marshall, Gerstein & Borun LLP

(57) ABSTRACT

The invention relates to substituted quinolones and to processes for their preparation as well as to their use for the production of medicaments for the treatment and/or prophylaxis of diseases, especially for use as antiviral agents, particularly against cytomegaloviruses.

16 Claims, No Drawings

SUBSTITUTED QUINOLONES

CROSS-REFERENCE TO RELATED APPLICATIONS

This application is a continuation of pending International Patent Application PCT/EP2005/007601, filed on Jul. 13, 2005, designating US, which claims priority from German Patent Application DE 10 2004 035 203.8, filed on Jul. 21, 2004. The contents of the above-referenced applications are incorporated herein by this reference in their entirety.

BACKGROUND OF THE INVENTION

The invention relates to substituted quinolones and to processes for their preparation as well as to their use for the production of medicaments for the treatment and/or prophylaxis of diseases, especially for use as antiviral agents, particularly against cytomegaloviruses.

WO 00/040561 and U.S. Pat. No. 4,959,363 describe quinolones with activity against viruses of the herpes family. EP-A 612731 describes quinolones as antiviral agents, particularly against HIV. WO 02/009758, WO 02/085886 and WO 03/050107 claim quinolones as broad-spectrum antibiotics. WO 97/004775 and WO 97/004779 describe quinolones as inhibitors of PDE4 and TNFα, among other things for the treatment of antiinflammatory diseases and HIV. EP-A 276700 describes 8-cyanoquinolones as antibiotics. WO 02/026713 describes quinolones as antiparasitic compounds.

On the market there are structurally different agents having antiviral activity, but their breadth of application is severely restricted owing to a pronounced side-effect profile and a possible development of resistances. New agents for a better and more effective therapy are therefore desirable.

One object of the present invention is therefore to provide new compounds with equal or improved antiviral action for the treatment of viral infectious diseases in humans and animals.

SUMMARY OF THE INVENTION

Surprisingly it has been found that the substituted quinolones described in the present invention have antiviral activity.

The invention relates to compounds of formula

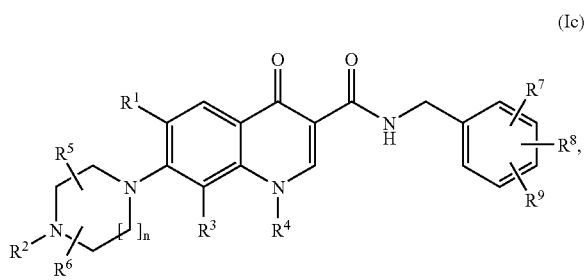

(Ic)

in which n represents a number 1 or 2, $R^1$ represents fluorine, chlorine or trifluoromethyl, $R^2$ represents hydrogen or $C_1$-$C_6$-alkyl, whereby alkyl can be substituted with 1 to 2 substituents, whereby the substituents are selected independently of one another from the group consisting of hydroxy, aminocarbonyl, $C_1$-$C_6$-alkoxy, $C_1$-$C_6$-alkylcarbonyl, $C_1$-$C_6$-alkylaminocarbonyl, $C_3$-$C_8$-cycloalkylaminocarbonyl, $C_1$-$C_6$-alkylaminocarbonylaminocarbonyl, $C_1$-$C_6$-alkylsulfonylaminocarbonyl, phenoxy, 5- or 6-membered heteroaryloxy, 5- to 7-membered heterocyclyl, 5- or 6-membered heteroaryl, 5- to 7-membered heterocyclylcarbonyl and 5- or 6-membered heteroarylcarbonyl, wherein alkoxy in turn can be substituted with a substituent, whereby the substituent is selected from the group consisting of hydroxy, phenyl, 5- to 7-membered heterocyclyl and 5- or 6-membered heteroaryl, or $R^2$ represents $C_1$-$C_6$-alkylcarbonyl, optionally $C_1$-$C_4$-alkoxy-substituted $C_1$-$C_6$-alkylaminocarbonyl, or $C_3$-$C_8$-cycloalkylaminocarbonyl, whereby alkylcarbonyl can be substituted with a substituent, whereby the substituent is selected from the group consisting of amino, $C_1$-$C_6$-alkylamino, $C_3$-$C_8$-cycloalkylamino, and 4- to 7-membered heterocyclyl, $R^3$ represents halogen, cyano, methoxy, monofluoromethoxy, difluoromethoxy, trifluoromethoxy or ethynyl, $R^4$ represents $C_1$-$C_6$-alkyl or $C_3$-$C_8$-cycloalkyl, whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl, and whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl, $R^5$ and $R^6$ independently of one another represent hydrogen, methyl or ethyl, $R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy, $R^9$ represents hydrogen, halogen, hydroxy, cyano, trifluoromethyl, monofluoromethoxy, difluoromethoxy, trifluoromethoxy, $C_1$-$C_3$-Alkyl or $C_1$-$C_3$-alkoxy, and their salts, their solvates, and the solvates of their salts.

Compounds of the invention are the compounds of formula (Ic), (I), (Ia) and (Ib) and their salts, solvates and solvates of the salts; the compounds of the formulae given below, encompassed by formula (Ic), (I), (Ia) and (Ib), and their salts, solvates and solvates of the salts, as well as the compounds specified below as exemplary embodiments, encompassed by formula (Ic), (I), (Ia) and (Ib), and their salts, solvates and solvates of the salts, in so far as the compounds mentioned below and encompassed by formula (Ic), (I), (Ia) and (Ib) are not already salts, solvates and solvates of the salts.

The compounds of the invention may, depending on their structure, exist in stereoisomeric forms (enantiomers, diastereomers). The invention therefore relates to the enantiomers or diastereomers and their respective mixtures. From such mixtures of enantiomers and/or diastereomers it is possible to isolate the stereoisomerically pure constituents, in a known way.

Where the compounds of the invention can occur in tautomeric forms, the present invention includes all tautomeric forms.

Salts preferred for the purposes of the present invention are physiologically acceptable salts of the compounds of the invention. Also included, however, are salts which are themselves not suitable for pharmaceutical applications, but can be used, for example, for the isolation or purification of the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-rhethylmorpholine, arginine, lysine, ethylenediamine and N-methylpiperidine.

Solvates for the purposes of the invention refer to those forms of the compounds of the invention which in solid or liquid state form a complex through coordination with solvent molecules. Hydrates are a special form of the solvates, in which the coordination takes place with water.

For the purposes of the present invention, the substituents have the following meaning, unless specified otherwise:

Alkyl per se and "alk" and "alkyl" in alkoxy, alkylamino, alkylcarbonyl, alkoxycarbonyl, alkylaminocarbonyl, alkylaminocarbonylaminocarbonyl and alkylsulfonylaminocarbonyl represent a linear or branched alkyl radical usually having 1 to 6, preferably 1 to 4, particularly preferably 1 to 3 carbon atoms, by way of example and preferably methyl, ethyl, n-propyl, isopropyl, tert-butyl, n-pentyl and n-hexyl.

Alkoxy by way of example and preferably represents methoxy, ethoxy, n-propoxy, isopropoxy, tert-butoxy, n-pentoxy and n-hexoxy.

Alkylamino represents an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkylamino represents for example a monoalkylamino radical having 1 to 3 carbon atoms or a dialkylamino radical having 1 to 3 carbon atoms per alkyl substituent.

Alkylcarbonyl represents by way of example and preferably acetyl and propanoyl.

Alkoxycarbonyl represents by way of example and preferably methoxycarbonyl, ethoxycarbonyl, n-propoxycarbonyl, isopropoxycarbonyl, tert-butoxycarbonyl, n-pentoxycarbonyl and n-hexoxycarbonyl.

Alkylaminocarbonyl represents an alkylaminocarbonyl radical having one or two alkyl substituents (chosen independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propyl-aminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl represents for example a monoalkylaminocarbonyl radical having 1 to 3 carbon atoms or a dialkylaminocarbonyl radical having 1 to 3 carbon atoms per alkyl substituent.

Alkylaminocarbonylaminocarbonyl represents an alkylaminocarbonylaminocarbonyl radical having one or two alkyl substituents (chosen independently of one another), by way of example and preferably methylaminocarbonylaminocarbonyl, ethylaminocarbonylaminocarbonyl, n-propylaminocarbonylaminocarbonyl, isopropylaminocarbonylaminocarbonyl, tert-butylaminocarbonylaminocarbonyl, n-pentylaminocarbonlyaminocarbonyl, n-hexylaminocarbonylaminocarbonyl, N,N-dimethylaminocarbonylaminocarbonyl, N,N-diethylaminocarbonylaminocarbonyl, N-ethyl-N-methylaminocarbonylaminocarbonyl, N-methyl-N-n-propylaminocarbonylaminocarbonyl, N-isopropyl-N-n-propylaminocarbonylaminocarbonyl, N-tert-butyl-N-methylaminocarbonylaminocarbonyl, N-ethyl-N-n-pentylaminocarbonylaminocarbonyl and N-n-hexyl-N-methylaminocarbonylaminocarbonyl. $C_1$-$C_3$-alkylaminocarbonylaminocarbonyl represents for example a monoalkylaminocarbonylaminocarbonyl radical having 1 to 3 carbon atoms or a dialkylaminocarbonylaminocarbonyl radical having 1 to 3 carbon atoms per alkyl substituent.

Alkylsulfonylaminocarbonyl represents by way of example and preferably methylsulfonylaminocarbonyl, ethylsulfonylaminocarbonyl, n-propylsulfonylaminocarbonyl, isopropylsulfonylaminocarbonyl, tert-butylsulfonylaminocarbonyl, n-pentylsulfonylaminocarbonyl and n-hexylsulfonylaminocarbonyl.

Cycloalkyl represents a cycloalkyl group usually having 3 to 8, preferably 3 to 5 carbon atoms, by way of example and preferably cycloalkyl includes cyclopropyl, cyclobutyl, cyclopentyl, cyclohexyl and cycloheptyl.

Cycloalkylamino represents by way of example and preferably cyclopropylamino, cyclobutylamino, cyclopentylamino, cyclohexylamino and cycloheptylamino.

Cycloalkylaminocarbonyl represents by way of example and preferably cyclopropylaminocarbonyl, cyclobutylaminocarbonyl, cyclopentylaminocarbonyl, cyclohexylaminocarbonyl and cycloheptylaminocarbonyl.

Heteroaryl per se and "heteroaryl" in heteroaryloxy and heteroarylcarbonyl represents an aromatic, mono- or bicyclic radical usually having 5 to 10, preferably 5 to 6 ring atoms and up to 5, preferably up to 4 heteroatoms from the series S, O and N, whereby heteroaryl can carry an oxo substituent, by way of example and preferably thienyl, furyl, pyrrolyl, thiazolyl, oxazolyl, isoxazolyl, oxadiazolyl, pyrazolyl, imidazolyl, tetrazolyl, pyridyl, pyrimidyl, pyridazinyl, pyrazinyl, indolyl, indazolyl, benzofuranyl, benzothiophenyl, quinolinyl, isoquinolinyl.

Heteroaryloxy by way of example and preferably represents thienyloxy, furyloxy, pyrrolyloxy, thiazolyloxy, oxazolyloxy, isoxazolyloxy, oxadiazolyloxy, pyrazolyloxy, imidazolyloxy, tetrazolyloxy, pyridyloxy, pyrimidyloxy, pyridazinyloxy, pyrazinyloxy, indolyloxy, indazolyloxy, benzofuranyloxy, benzothiophenyloxy, quinolinyloxy, isoquinolinyloxy.

Heteroarylcarbonyl by way of example and preferably represents thienylcarbonyl, furylcarbonyl, pyrrolylcarbonyl, thiazolylcarbonyl, oxazolylcarbonyl, isoxazolylcarbonyl, oxadiazolylcarbonyl, pyrazolylcarbonyl, imidazolylcarbonyl, tetrazolylcarbonyl, pyridylcarbonyl, pyrimidylcarbonyl, pyridazinylcarbonyl, pyrazinylcarbonyl, indolylcarbonyl, indazolylcarbonyl, benzofuranylcarbonyl, benzothiophenylcarbonyl, quinolinylcarbonyl, isoquinolinylcarbonyl.

Heterocyclyl per se and "heterocyclyl" in heterocyclylcarbonyl represents a mono- or polycyclic, preferably mono- or bicyclic, heterocyclic radical usually having 4 to 10, preferably 5 to 8 ring atoms and up to 3, preferably up to 2 heteroatoms and/or hetero-groups from the series N, O, S, SO, $SO_2$. The heterocyclyl radicals may be saturated or partly unsaturated. Preference is given to 5- to 8-membered, monocyclic saturated heterocyclyl radicals having up to two heteroatoms from the series O, N and S, such as, by way of example and preferably, tetrahydrofuran-2-yl, tetrahydrofuran-3-yl, pyrrolidin-2-yl, pyrrolidin-3-yl, pyrrolinyl, piperidin-1-yl, piperidin-2-yl, piperidin-3-yl, piperidin-4-yl, piperazin-1-yl, piperazin-2-yl, morpholin-2-yl, morpholin-3-yl, morpholin-4-yl, thiomorpholin-2-yl, thiomorpholin-3-yl, thiomorpholin-4-yl, perhydroazepin-1-yl, perhydroazepin-2-yl, perhydroazepin-3-yl, perhydroazepin-4-yl.

Pyrrolinyl per se and "pyrrolinyl" in pyrrolinylcarbonyl represents 3,4-dihydro-2H-pyrrol-2-yl, 3,4-dihydro-2H-pyrrol-3-yl, 3,4-dihydro-2H-pyrrol-4-yl, 3,4-dihydro-2H-pyrrol-5-yl, 2,3-dihydro-1H-pyrrol-1-yl, 2,3-dihydro-1H-pyrrol-2-yl, 2,3-dihydro-1H-pyrrol-3-yl, 2,3-dihydro-1H-pyrrol-4-yl, 2,3-dihydro-1H-pyrrol-5-yl, 2,5-dihydro-1H-pyrrol-1-yl, 2,5-dihydro-1H-pyrrol-2-yl, 2,5-dihydro-1H-pyrrol-3-yl, 2,5-dihydro-1H-pyrrol-4-yl and 2,5-dihydro-1H-pyrrol-5-yl.

Heterocyclylcarbonyl by way of example and preferably represents tetrahydrofuran-2-ylcarbonyl, tetrahydrofuran-3-ylcarbonyl, pyrrolidin-2-ylcarbonyl, pyrrolidin-3-ylcarbonyl, pyrrolinylcarbonyl, piperidin-1-ylcarbonyl, piperidin-2-ylcarbonyl, piperidin-3-ylcarbonyl, piperidin-4-ylcarbonyl, piperazin-1-ylcarbonyl, piperazin-2-ylcarbonyl, morpholin-2-ylcarbonyl, morpholin-3-ylcarbonyl, morpholin-4-ylcarbonyl, thiomorpholin-2-ylcarbonyl, thiomorpholin-3-ylcarbonyl, thiomorpholin-4-ylcarbonyl, perhydroazepin-1-ylcarbonyl, perhydroazepin-2-ylcarbonyl, perhydroazepin-3-ylcarbonyl, perhydroazepin-4-ylcarbonyl.

Halogen represents fluorine, chlorine, bromine and iodine, preferably fluorine and chlorine.

Preference is given to those compounds of formula (Ic) which correspond to formula

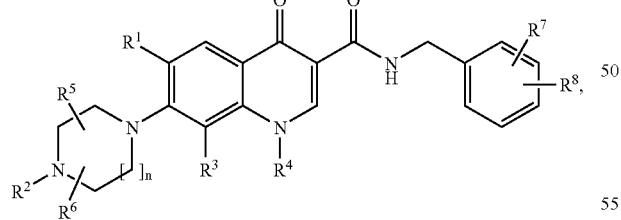

(I)

in which
n represents a number 1 or 2,
$R^1$ represents fluorine, chlorine or trifluoromethyl,
$R^2$ represents hydrogen or $C_1$-$C_6$-alkyl,
whereby alkyl can be substituted with 1 to 2 substituents, whereby the substituents are selected independently of one another from the group consisting of hydroxy, aminocarbonyl, $C_1$-$C_6$-alkoxy, $C_1$-$C_6$-alkylcarbonyl, $C_1$-$C_6$-alkylaminocarbonyl, $C_3$-$C_8$-cycloalkylaminocarbonyl, $C_1$-$C_6$-alkylsulfonylaminocarbonyl, phenoxy, 5- or 6-membered heteroaryloxy, 5- to 7-membered heterocyclyl, 5- or 6-membered heteroaryl, 5- to 7-membered heterocyclylcarbonyl and 5- or 6-membered heteroarylcarbonyl,
wherein alkoxy in turn can be substituted with a substituent, whereby the substituent is selected from the group consisting of hydroxy, phenyl, 5- to 7-membered heterocyclyl and 5- or 6-membered heteroaryl, or
$R^2$ represents $C_1$-$C_6$-alkylcarbonyl, optionally $C_1$-$C_4$-alkoxy-substituted $C_1$-$C_6$-alkylaminocarbonyl, or $C_3$-$C_8$-cycloalkylaminocarbonyl,
whereby alkylcarbonyl can be substituted with a substituent, whereby the substituent is selected from the group consisting of amino, $C_1$-$C_6$-alkylamino, $C_3$-$C_8$-cycloalkylamino, and 4- to 7-membered heterocyclyl,
$R^3$ represents halogen, cyano, methoxy, monofluoromethoxy, difluoromethoxy, trifluoromethoxy or ethynyl,
$R^4$ represents $C_1$-$C_6$-alkyl or $C_3$-$C_8$-cycloalkyl,
whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl, and
whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl,
$R^5$ and $R^6$ independently of one another represent hydrogen, methyl or ethyl,
$R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy,
and their salts, their solvates and the solvates of their salts.

Preference is also given to those compounds of formula (I), in which
n represents a number 1 or 2,
$R^1$ represents fluorine, chlorine or trifluoromethyl
$R^2$ represents hydrogen or $C_1$-$C_6$-alkyl,
whereby alkyl can be substituted with 1 to 2 substituents, whereby the substituents are selected independently of one another from the group consisting of hydroxy, aminocarbonyl, $C_1$-$C_6$-alkoxy, $C_1$-$C_6$-alkylaminocarbonyl, phenoxy, 5- or 6-membered heteroaryloxy, 5- to 7-membered heterocyclyl, 5- or 6-membered heteroaryl, 5- to 7-membered heterocyclylcarbonyl and 5- or 6-membered heteroarylcarbonyl,
wherein alkoxy in turn can be substituted with a substituent, whereby the substituent is selected from the group consisting of hydroxy, phenyl, 5- to 7-membered heterocyclyl and 5- or 6-membered heteroaryl,
$R^3$ represents halogen, cyano, methoxy, monofluoromethoxy, difluoromethoxy, trifluoromethoxy or ethynyl,
$R^4$ represents $C_1$-$C_6$-alkyl or $C_3$-$C_8$-cycloalkyl, whereby alkyl can be substituted with 1 to 3 substituents, whereby the substituents are selected independently of one another from the group consisting of hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl, and whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl, $R^5$ and $R^6$ independently of one another represent hydrogen, methyl or ethyl, $R^7$ and $R^8$ independently of one another represent halogen, hydroxy, cyano, monofluoromethoxy, difluoromethoxy, trifluoromethoxy, $C_1$-$C_3$-alkyl or $C_1$-$C_3$-alkoxy, and their salts, their solvates and the solvates of their salts.

Preference is also given to those compounds of formula (I) which correspond to formula

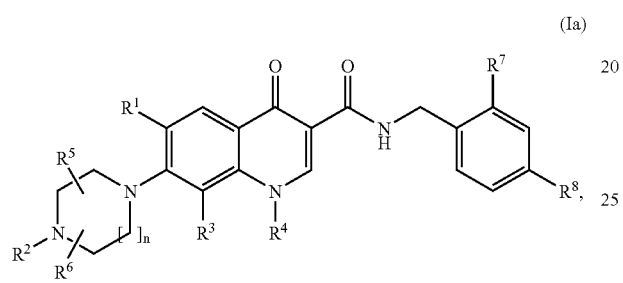

(Ia)

in which n represents a number 1 or 2, $R^1$ represents fluorine, $R^2$ represents hydrogen or $C_1$-$C_6$-alkyl, whereby alkyl can be substituted with 1 to 2 substituents, whereby the substituents are selected independently of one another from the group consisting of hydroxy, $C_1$-$C_6$-alkoxy, 5- or 6-membered heterocyclyl and 5- or 6-membered heterocyclylcarbonyl, wherein alkoxy in turn can be substituted with a substituent, whereby the substituent is selected from the group consisting of hydroxy and 5- or 6-membered heterocyclyl, or $R^2$ represents $C_1$-$C_6$-alkylcarbonyl, whereby alkylcarbonyl is substituted with an amino substituent, $R^3$ represents fluorine, chlorine, methoxy, monofluoromethoxy, difluoromethoxy, trifluoromethoxy or ethynyl, $R^4$ represents $C_1$-$C_4$-alkyl or $C_3$-$C_5$-cycloalkyl, whereby alkyl can be substituted with 1 to 3 substituents, whereby the substituents are selected independently of one another from the group consisting of hydroxy, and $C_1$-$C_3$-alkoxy, and whereby cycloalkyl can be substituted with 1 to 3 substituents, whereby the substituents are selected independently of one another from the group consisting of halogen, hydroxy, trifluoromethyl, $C_1$-$C_3$-alkyl, $C_1$-$C_3$-alkoxy, $R^5$ and $R^6$ independently of one another represent hydrogen or methyl, $R^7$ and $R^8$ independently of one another represent fluorine, chlorine, cyano, trifluoromethyl, difluoromethoxy, trifluoromethoxy $C_1$-$C_3$-alkyl or $C_1$-$C_3$-alkoxy, and their salts, their solvates and the solvates of their salts.

Preference is also given to those compounds of formula (I) which correspond to formula

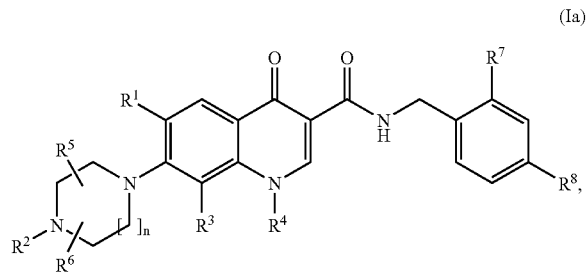

(Ia)

in which n represents a number 1 or 2, $R^1$ represents fluorine, $R^2$ represents hydrogen or $C_1$-$C_6$-alkyl, whereby alkyl can be substituted with 1 to 2 substituents, whereby the substituents are selected independently of one another from the group consisting of hydroxy, $C_1$-$C_6$-alkoxy, 5- or 6-membered heterocyclyl and 5- or 6-membered heterocyclylcarbonyl, wherein alkoxy in turn can be substituted with a substituent, whereby the substituent is selected from the group consisting of hydroxy and 5- or 6-membered heterocyclyl, $R^3$ represents fluorine, chlorine, methoxy, monofluoromethoxy, difluoromethoxy, trifluoromethoxy or ethynyl, $R^4$ represents $C_1$-$C_4$-alkyl or $C_3$-$C_5$-cycloalkyl, whereby alkyl can be substituted with 1 to 3 substituents, whereby the substituents are selected independently of one another from the group consisting of hydroxy, and $C_1$-$C_3$-alkoxy, and whereby cycloalkyl can be substituted with 1 to 3 substituents, whereby the substituents are selected independently of one another from the group consisting of halogen, hydroxy, trifluoromethyl, $C_1$-$C_3$-alkyl, $C_1$-$C_3$-alkoxy, $R^5$ and $R^6$ independently of one another represent hydrogen or methyl, $R^7$ and $R^8$ independently of one another represent fluorine, chlorine, cyano, difluoromethoxy, trifluoromethoxy $C_1$-$C_3$-alkyl or $C_1$-$C_3$-alkoxy, and their salts, their solvates and the solvates of their salts.

Preference is given in particular to those compounds of formula (I) or (Ia) which correspond to formula

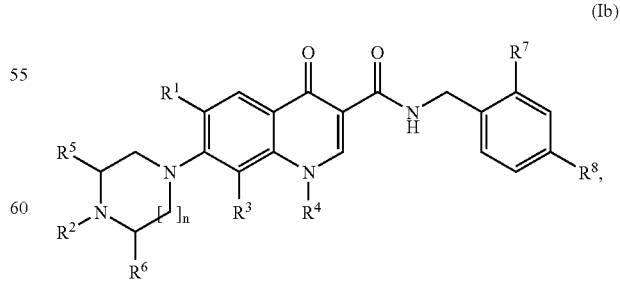

(Ib)

in which n represents a number 1 or 2, $R^1$ represents fluorine, $R^2$ represents hydrogen or $C_1$-$C_3$-alkyl,
whereby alkyl can be substituted with 1 or 2 substituents, whereby the substituents are selected independently of one another from the group consisting of hydroxy, morpholin-2-ylcarbonyl, morpholin-3-ylcarbonyl, morpholin-4-ylcarbonyl, piperidin-1-ylcarbonyl, piperidin-2-ylcarbonyl, piperidin-3-ylcarbonyl, piperidin-4-ylcarbonyl, pyrrolidin-2-ylcarbonyl, pyrrolidin-3-ylcarbonyl and $C_1$-$C_3$-alkoxy which is optionally substituted with a hydroxy substituent, or $R^2$ represents $C_1$-$C_4$-alkylcarbonyl,
whereby alkylcarbonyl is substituted with an amino substituent, $R^3$ represents chlorine, methoxy, difluoromethoxy or trifluoromethoxy, $R^4$ represents methyl, ethyl or cyclopropyl,
whereby ethyl can be substituted with 1 to 3 fluorine substituents, and
whereby cyclopropyl can be substituted with 1 to 2 fluorine substituents, $R^5$ and $R^6$ independently of one another represent hydrogen or methyl, $R^7$ and $R^8$ independently of one another represent chlorine, trifluoromethyl, trifluoromethoxy or methyl.

and their salts, their solvates and the solvates of their salts.

Preference is given in particular to those compounds of formula (I) or (Ia) which correspond to formula

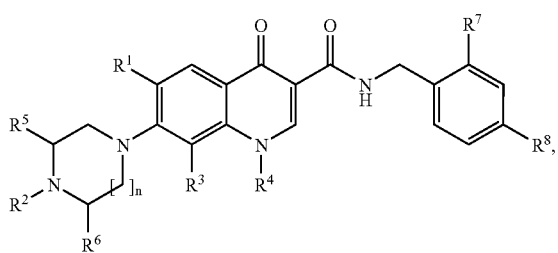

(Ib)

in which
n represents a number 1 or 2,
$R^1$ represents fluorine,
$R^2$ represents hydrogen or $C_1$-$C_3$-alkyl,
whereby alkyl can be substituted with 1 to 2 substituents, whereby the substituents are selected independently of one another from the group consisting of hydroxy, morpholin-2-ylcarbonyl, morpholin-3-ylcarbonyl, morpholin-4-ylcarbonyl, piperidin-1-ylcarbonyl, piperidin-2-ylcarbonyl, piperidin-3-ylcarbonyl, piperidin-4-ylcarbonyl, pyrrolidin-2-ylcarbonyl, pyrrolidin-3-ylcarbonyl and $C_1$-$C_3$-alkoxy which is optionally substituted with a hydroxy substituent, $R^3$ represents chlorine, methoxy, difluoromethoxy or trifluoromethoxy, $R^4$ represents methyl, ethyl or cyclopropyl,
whereby cyclopropyl can be substituted with 1 to 2 fluorine substituents, $R^5$ and $R^6$ independently of one another represent hydrogen or methyl, $R^7$ and $R^8$ independently of one another represent chlorine or methyl.

and their salts, their solvates and the solvates of their salts.

Preference is also given to those compounds of formula (Ic), (I), (Ia) and (Ib) in which $R^1$ represents fluorine.

Preference is also given to those compounds of formula (Ic), (I), (Ia) and (Ib) in which $R^3$ represents chlorine, methoxy or difluoromethoxy.

Preference is also given to those compounds of formula (Ic), (I), (Ia) and (Ib) in which $R^4$ represents cyclopropyl or 2-fluorocycloprop-1-yl.

Preference is also given to those compounds of formula (Ic), (I), (Ia) and (Ib) in which $R^4$ represents 2,2,2-trifluoroethyl.

Preference is also given to those compounds of formula (Ic), (I), (Ia) and (Ib) in which $R^7$ and $R^8$ represent chlorine.

Preference is also given to those compounds of formula (Ic), (I), (Ia) and (Ib) in which $R^7$ represents chlorine or methyl and $R^8$ represents trifluoromethoxy.

Preference is also given to those compounds of formula (Ic), (I), (Ia) and (Ib) in which $R^2$ represents hydrogen, aminomethylcarbonyl or 2,3-dihydroxyprop-1-yl and $R^5$ and $R^6$ represent methyl.

Preference is also given to those compounds of formula (Ic), (I), (Ia) and (Ib) in which $R^2$ represents hydrogen and $R^5$ and $R^6$ represent methyl.

Preference is also given to those compounds of formula (Ic) in which $R^9$ represents hydrogen.

The radical definitions stated specifically in the respective combinations and preferred combinations of radicals are also replaced as desired by radical definitions of other combinations, irrespective of the particular combinations of the radicals that are specified.

Very particular preference is given to combinations of two or more of the abovementioned preference ranges.

The invention further relates to a process for the preparation of the compounds of formula (Ic), whereby compounds of the formula

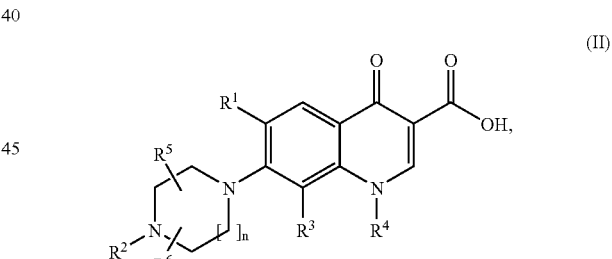

(II)

in which
n, $R^1$, $R^2$, $R^3$, $R^4$, $R^5$ and $R^6$ have the meaning indicated above,
are reacted with compounds of formula

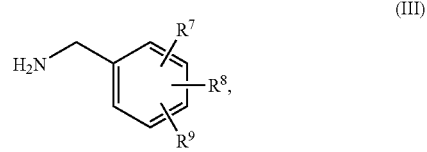

(III)

in which
$R^7$, $R^8$ and $R^9$ have the meaning indicated above.

The reaction generally takes place in inert solvents, in the presence of a dehydrating reagent, optionally in the presence of a base, preferably in a temperature range from −30° C. to 50° C. under atmospheric pressure.

Inert solvents are for example halogenated hydrocarbons such as dichloromethane or trichloromethane, hydrocarbon such as benzene, nitromethane, dioxane, dimethylformamide or acetonitrile. It is also possible to use mixtures of the solvents. Particularly preferred is dichloromethane or dimethylformamide.

Bases are for example alkali metal carbonates, such as sodium or potassium carbonate, or hydrogen carbonate, or organic bases such as trialkylamines, for example triethylamine, N-methylmorpholine, N-methylpiperidine, 4-dimethylaminopyridine or diisopropylethylamine.

Dehydrating reagents suitable here include for example carbodiimides such as N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride, or O-(benzo-triazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt) or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures of these with bases.

Preferably the condensation is carried out with HATU, benzotriazol-1-yloxytris(pyrrolidino)phosphonium hexafluorophosphate (PyBOP) or with EDC in the presence of HOBt.

The compounds of formula (II) are known or can be prepared by reacting compounds of formula

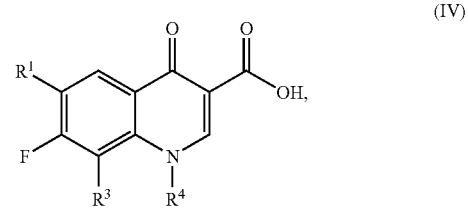

(IV)

in which

R¹, R³ and R⁴ have the meaning indicated above,
with compounds of formula

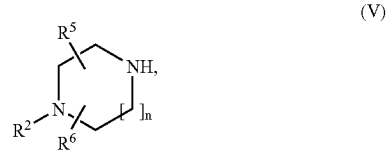

(V)

in which n, R², R⁵ and R⁶ have the meaning indicated above,

The reaction can be carried out according to the methods described in A. Da Silva, M. De Almeida, V. De Souza, M. Couri, *Current Medicinal Chemistry* (2003) 10:21-39 or J. P. Sanchez, et al., *Journal of Medicinal Chemistry* (1995) 38:4478-4487.

The compounds of formula (III) and (V) are known or can be synthesized by known methods from the corresponding starting materials.

The compounds of formula (V) optionally carry protecting groups known to a man of the art during the reaction, which can be removed either directly after the reaction of the compounds of formula (IV) with compounds of formula (V) to compounds of formula (II) or after a further reaction to compounds of formula (Ic).

The compounds of formula (IV) are known or can be synthesized according to known methods from the corresponding starting materials, as described for example in A. Da Silva, M. De Almeida, V. De Souza, M. Couri, *Current Medicinal Chemistry* (2003) 10:21-39.

In an alternative method substituent R² in compounds of formula (Ic) can be introduced by reacting compounds of formula

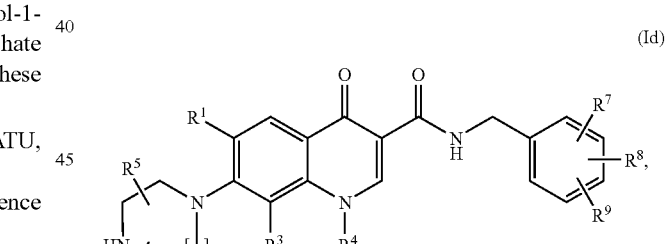

(Id)

in which n, R¹, R³, R⁴, R⁵, R⁶, R⁷, R⁸ and R⁹ have the meaning indicated above, with electrophiles such as carboxylic acid chlorides, optionally substituted chloroacetamide, optionally substituted 2-chloropropionamide, chloromethylketones or optionally substituted 3-bromopropionamide, in the presence of a base or by reaction with isocyanates, Michael acceptors or epoxides.

In an alternative method for the production of compounds of formula (Ic) the nucleophilic substitution in 7-position of the quinolone and the formation of the amide can be exchanged in the order of reaction.

The preparation of the compounds of the invention can be illustrated with the following synthesis scheme.

Synthesis scheme:
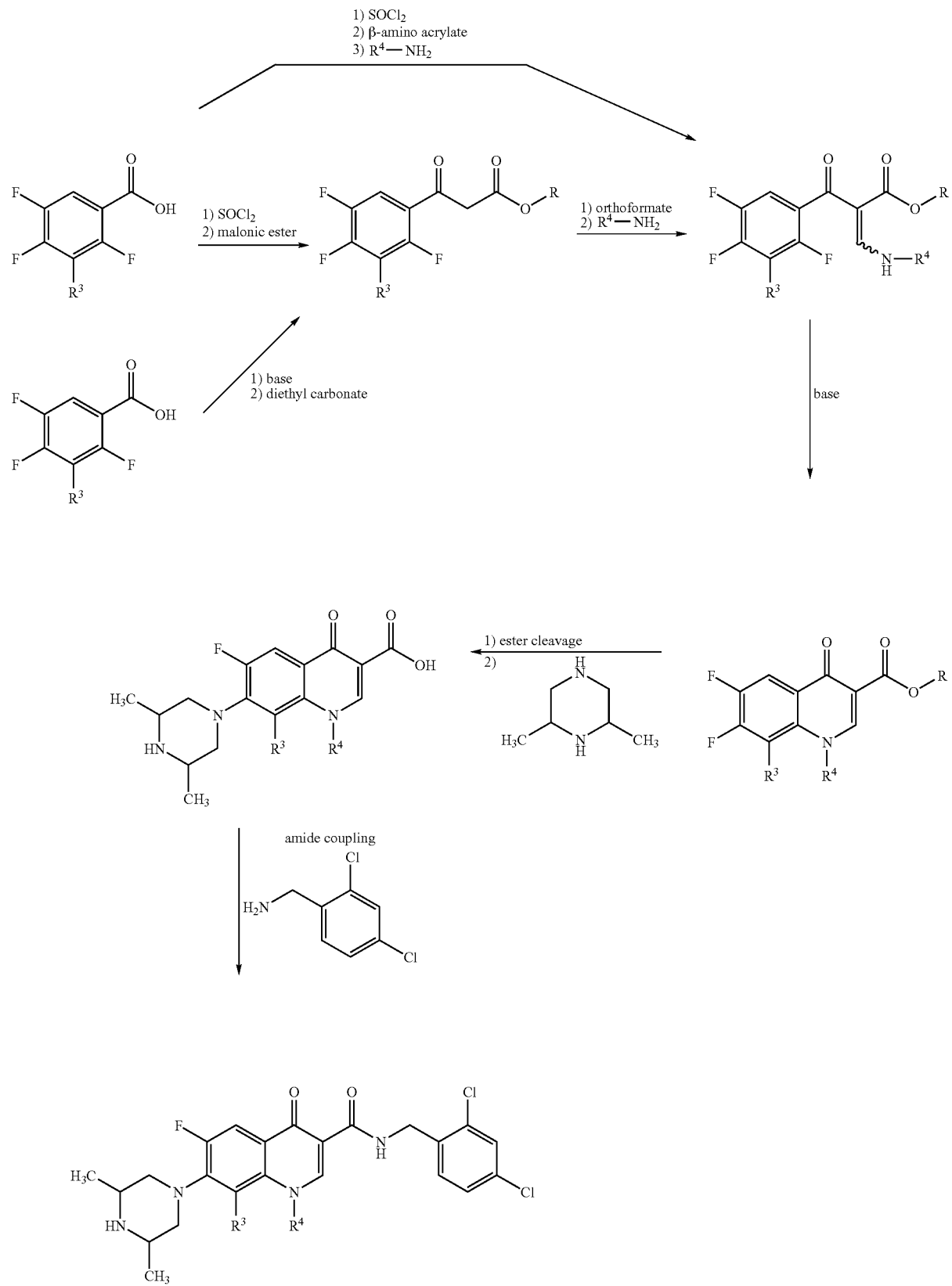

The compounds of the invention show a surprising range of effects which could not have been predicted. They show an antiviral effect on representatives of the group of herpes viridae (herpes viruses), in particular on cytomegaloviruses (CMV) and especially on the human cytomegalovirus (HCMV).

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone-marrow and organ transplant patients who develop often life-threatening HCMV pneumonitis or encephalitis, as well as gastrointestinal and systemic HCMV infections.
3) Treatment and prophylaxis of HCMV infections in neonates and infants.
4) Treatment of an acute HCMV infection in pregnant women.
5) Treatment of an HCMV infection in immunosuppressed patients during cancer and cancer therapy.
6) Treatment of HCMV-positive cancer patients with the aim of reducing HCMV-mediated tumour progression (cf. J. Cinatl, et al., *FEMS Microbiology Reviews* (2004) 28:59-77.

The present invention further relates to the use of the compounds of the invention for the treatment and/or prophylaxis of diseases, in particular of infections with viruses, especially the aforementioned viruses, and of the infectious diseases caused thereby. A viral infection means hereinafter both an infection with a virus and a disease caused by an infection with a virus.

The present invention further relates to the use of the compounds of the invention for the treatment and/or prophylaxis of diseases, especially of the aforementioned diseases.

The present invention further relates to the use of the compounds of the invention for the production of a medicament for the treatment and/or prophylaxis of diseases, especially of the aforementioned diseases.

The compounds of the invention are preferably used for the production of medicaments which are suitable for the prophylaxis and/or treatment of infections with a representative of the group of herpes viridae, particularly a cytomegalovirus, in particular the human cytomegalovirus.

The present invention further relates to a method for the treatment and/or prophylaxis of diseases, especially the aforementioned diseases, using an antivirally effective amount of the compounds of the invention.

The present invention further relates to medicaments comprising at least one compound of the invention and at least one or more further active ingredients, in particular for the treatment and/or prophylaxis of the aforementioned diseases. Suitable active ingredients in the combination which may be mentioned by way of example and preferably are: antiviral active ingredients such as valganciclovir, ganciclovir or aciclovir.

The compounds of the invention may act systemically and/or locally. They can for this purpose be administered in a suitable way, such as, for example, orally, parenterally, pulmonarily, nasally, sublingually, lingually, buccally, rectally, dermally, transdermally, conjunctivally, otically or topically, or as implant or stent.

For these administration routes it is possible to administer the compounds of the invention in suitable administration forms.

Suitable for oral administration are administration forms which function according to the prior art and deliver the compounds of the invention rapidly and/or in modified fashion and which comprise the compounds of the invention in crystalline and/or amorphicized and/or dissolved form, such as, for example, tablets (uncoated or coated tablets, for example having coatings which are resistant to gastric juice or dissolve with a delay or are insoluble and control the release of the compound of the invention), tablets or films/wafers, which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (for example intravenous, intraarterial, intracardial, intraspinal or intralumbar) or with inclusion of an absorption (for example intramuscular, subcutaneous, intracutaneous, percutaneous, or intraperitoneal). Administration forms suitable for parenteral administration are, inter alia, preparations for injection and infusion in the form of solutions, suspensions, emulsions, lyophilisates or sterile powders.

Suitable for the other administration routes are for example pharmaceutical forms for inhalation (including powder inhalers, nebulizers), nasal drops, solutions, sprays; tablets, films/wafers or capsules, for lingual, sublingual or buccal administration, suppositories, preparations for the ears or eyes, vaginal capsules, aqueous suspensions (lotions, shaking mixtures), lipophilic suspensions, ointments, creams, transdermal therapeutic systems, milk, pastes, foams, dusting powders, implants or stents.

The compounds of the invention can be converted into the stated administration forms. This can take place in a manner known per se by mixing with inert, non-toxic, pharmaceutically acceptable excipients. These excipients include, inter alia, carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants such as ascorbic acid), colors (for example inorganic pigments such as iron oxides) or taste- and/or odor corrigents.

The present invention further relates to medicaments which comprise at least one compound of the invention, usually together with one or more inert, non-toxic, pharmaceutically acceptable excipients, and to the use thereof for the aforementioned purposes.

It has generally proven advantageous on intravenous administration to administer amounts of about 0.001 to 10 mg/kg, preferably about 0.01 to 5 mg/kg of body weight to achieve effective results, and the dosage on oral administration is about 0.01 to 25 mg/kg, preferably 0.1 to 10 mg/kg of body weight.

It may nevertheless be necessary where appropriate to deviate from the amounts mentioned, depending on the body weight, administration route, individual behavior towards to the active ingredient, nature of the preparation and time or interval over which administration takes place. Thus it may be sufficient in some cases to make do with less than the aforementioned minimum amount, whereas in other cases the stated upper limit must be exceeded. In the case of an administration of larger amounts it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

DETAILED DESCRIPTION OF PREFERRED EMBODIMENTS

A. EXAMPLES

| Abbreviations: | |
|---|---|
| BINAP | 2,2'-bis(diphenylphosphino)-1,1'-binaphthyl |
| CDCl$_3$ | Deuterochloroform |
| DCI | direct chemical ionization (in MS) |
| DCM | Dichloromethane |
| DIEA | N,N-diisopropylethylamine |
| DMSO | dimethyl sulfoxide |
| DMF | N,N-dimethylformamide |
| EE | ethyl acetate (acetic acid ethyl ester) |
| EI | electron impact ionization (in MS) |
| ESI | electrospray ionization (in MS) |
| H | Hour |
| HPLC | high pressure, high performance liquid chromatography |
| LC-MS | coupled liquid chromatography-mass spectroscopy |
| LDA | lithium diisopropylamide |
| min | Minutes |
| m.p. | melting point |
| MS | mass spectroscopy |
| MTBE | methyl tert-butyl ether |
| NMR | nuclear magnetic resonance spectroscopy |
| Pd-C | palladium on carbon |
| PyBOP | 1-benzotriazolyloxytripyrrolidinophosphonium hexafluorophosphate |
| RP-HPLC | reverse phase HPLC |
| RT | room temperature |
| R$_t$ | retention time (in HPLC) |
| THF | Tetrahydrofuran |
| TLC | thin layer chromatography |

General LC-MS and HPLC Methods:

Method 1 (LC-MS): Instrument: Micromass Quattro LCZ with HPLC Agilent series 1100; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 2 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 3 (LC-MS): MS instrument type: Micromass ZQ; HPLC instrument type: HP 1100 series; UV DAD; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (preparative HPLC): column: RP18; gradient, with addition of 0.2% diethylamine to the acetonitrile: 30% acetonitrile/70% water→95% acetonitrile/5% water.

Method 5 (preparative HPLC, formic acid): Column: Grom-Sil 120 ODS-4HE, 10 μm, SNr. 3331, 250 mm×30 mm. Eluent A: formic acid 0.1% in water, eluent B: acetonitrile; flow rate: 50 ml/min. Program: 0-3 min: 10% B; 3-27 min: gradient to 95% B; 27-34 min: 95% B; 34.01-38 min: 10% B.

Method 6 (preparative HPLC, hydrochloric acid): Column: Grom-Sil 120 ODS-4HE, 10 μm, SNr. 3331, 250 mm×30 mm. Eluent A: hydrochloric acid 0.1% in water, eluent B: acetonitrile; flow rate: 50 ml/min. Program: 0-2 min 10% B, 3-43 min: gradient to 100% B, 43.01-45 min: 100% B.

Method 7 (preparative HPLC): Column: Grom-Sil 120 ODS-4HE, 10 μm, SNr. 3331, 250 mm×30 mm. Eluent A: water, Eluent B: acetonitrile, flow rate: 50 ml/min. Program: 0-3 min: 10% B; 3-27 min: gradient to 95% B; 27-34 min: 95% B; 34.01-38 min: 10% B.

Method 8 (preparative HPLC, trifluoroacetic acid): Column: Grom-Sil 120 ODS-4HE, 10 μm, SNr. 3331, 250 mm×30 mm. Eluent A: trifluoroacetic acid 0.1% in water, eluent B: acetonitrile. Flow rate: 50 ml/min. Program: 0-3 min: 10% B; 3-27 min: gradient to 95% B; 27-34 min: 95% B; 34.01-38 min: 10% B.

Method 9 (analytical HPLC): Instrument: HP 1100 with DAD detection; column: Kromasil 100 RP-18, 60 mm×2.1 mm, 3.5 μm; eluent A: 5 ml perchloric acid (70%)/1 water, eluent B: acetonitrile; gradient: 0 min 2% B, 0.5 min 2% B, 4.5 min 90% B, 9 min 90% B, 9.2 min 2% B, 10 min 2% B; flow rate: 0.75 ml/min; column temperature: 30° C.; UV detection: 210 nm.

Method 10 (analytical HPLC): Instrument: HP 1100 with DAD detection; column: Kromasil 100 RP-18, 60 mm×2.1 mm, 3.5 μm; eluent A: 5 ml perchloric acid (70%)/1 water, eluent B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; column-temperature: 30° C.; UV detection: 210 nm.

Method 11 (LC-MS): MS Instrument type: Micromass TOF (LCT); HPLC instrument type: 2-column system, Waters 2690; column: YMC-ODS-AQ, 50 mm×4.6 mm, 3.0 μm; eluent A: water+0.1% formic acid, eluent B: acetonitrile+0.1% formic acid; gradient: 0.0 min 100% A→0.2 min 95% A→1.8 min 25% A→1.9 min 10% A→2.0 min 5% A→3.2 min 5% A; oven: 40° C.; flow rate: 3.0 ml/min; UV detection: 210 nm.

Method 12 (preparative LC-MS): MS instrument type: Micromass Micromass ZMD; HPLC instrument type: Waters Prep LC 4000; column: Kromasil, 50 mm×20 mm, 100 Å, C18 5 μm; eluent A: water+0.1% formic acid, eluent B: acetonitrile+0.1% formic acid; gradient: 0.0 min 70% A→0.75 min 70% A→5.5 min 100% B→6.5 min 100% B→7.0 min 70% A→flow rate: 40.0 ml/min.

Method 13 (LC-MS): Instrument: Micromass Platform LCZ with HPLC Agilent series 1100; column: Thermo Hypersil GOLD 3μ 20 mm×4 mm; eluent A: 1 l water+0.5 ml 50% formic acid, eluent B: 1 l acetonitrile+0.5 ml 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

The exemplary compounds which comprise a basic nitrogen can depending on the method of their purification be isolated as a free base or in various salt forms. The production method often describes the purification by HPLC with the addition of formic acid (method 5) which leads to the hydroformate or with the addition of other acids such as for example hydrochloric acid (method 6) instead of formic acid whereby the product is isolated as the hydrochloride. Alternatively the product can also be purified by stirring in acetonitrile or by preparative HPLC without the addition of acid (method 7) whereby the product is isolated as a free base.

From the free bases, as well as from the hydroformate, the hydrochloride of a compound can be obtained by subsequent mixing with hydrochloric acid in dioxane and evaporation on a rotary evaporator.

Starting Compounds

Example 1A

8-Chloro-1-cyclopropyl-6-fluoro-7-[4-(2-hydroxyethyl)-1,4-diazepan-1-yl]-4-oxo-1,4-dihydroquinoline-3-carboxylic acid

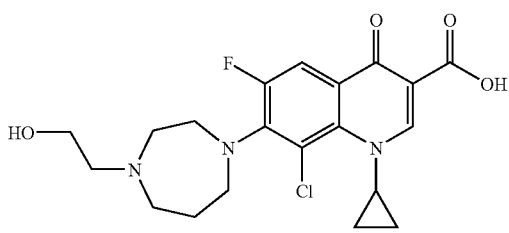

350 mg (1.2 mmol) of 8-Chloro-1-cyclopropyl-6,7-difluoro-4-oxo-1,4-dihydroquinoline-3-carboxylic acid (for preparation see: DE 3420743) are dissolved according to DE 3635218 in 3 ml of dry pyridine and heated at reflux with 202 mg (1.4 mmol) of hexahydro-1H-1,4-diazepine-1-ethanol for 4 hours. After standing overnight the mixture is concentrated, taken up with water and brought to pH 6 using dilute hydrochloric acid. The solution is saturated with sodium chloride at boiling heat. After it has cooled to room temperature, it is extracted a number of times with dichloromethane. The organic extracts are filtered over a little silica gel and concentrated. 288 mg of the target compound are obtained this way. The compound is used as a crude product in the subsequent reaction stages.

LC-MS (Method 3): $R_t$=1.32 min, MS (ES+)=424 (M+H)$^+$

In analogy to the preparation instructions of Example 1A, Examples 2A to 12A are prepared:

Example 2A

8-Chloro-1-cyclopropyl-6-fluoro-7-{4-[2-(2-hydroxyethoxy)ethyl]piperazin-4-yl}-4-oxo-1,4-dihydroquinoline-3-carboxylic acid

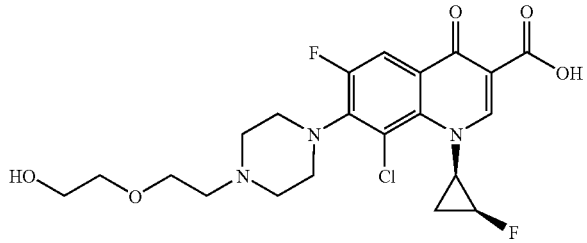

The preparation takes place in analogy to Example 1A from 8-chloro-1-cyclopropyl-6,7-difluoro-4-oxo-1,4-dihydroquinoline-3-carboxylic acid (for preparation see DE 3420743).

LC-MS (Method 2): $R_t$=1.08 min, MS (ES+)=454 (M+H)$^+$

Example 3A

8-Chloro-6-fluoro-1-[(1R,2S)-2-fluorocyclopropyl]-7-{4-[2-(2-hydroxyethoxy)ethyl]piperazine-1-yl}-4-oxo-1,4-dihydroquinoline-3-carboxylic acid

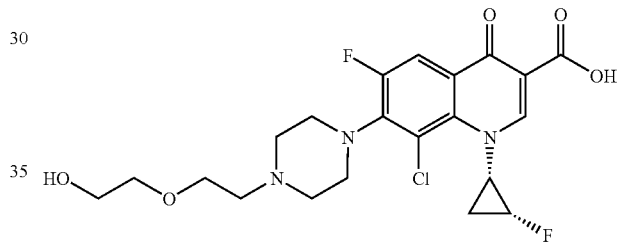

The Preparation takes place in analogy to Example 1A from 8-chloro-6,7-difluoro-1-[(1R,2S)-2-fluorocyclopropyl]-4-oxo-1,4-dihydroquinoline-3-carboxylic acid (for preparation see *Journal of Medicinal Chemistry* (1994) 37:3344-3352).

LC-MS (Method 2): $R_t$=1.28 min, MS (ES+)=472 (M+H)$^+$

Example 4A

8-Chloro-6-fluoro-1-[(1S,2R)-2-fluorocyclopropyl]-7-{4-[2-(2-hydroxyethoxy)ethyl]piperazine-1-yl}-4-oxo-1,4-dihydroquinoline-3-carboxylic acid

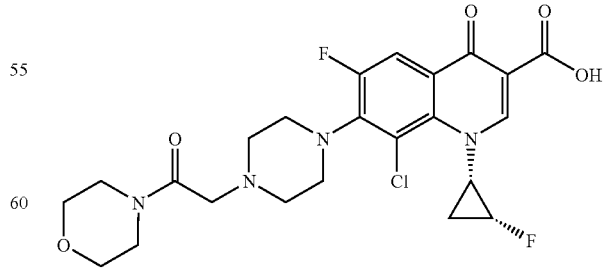

The preparation takes place in analogy to Example 1A from 8-chloro-6,7-difluoro-1-[(1S,2R)-2-fluorocyclopropyl]-4-oxo-1,4-dihydroquinoline-3-carboxylic acid (for preparation see *Journal of Medicinal Chemistry* (1994) 37:3344-3352). The compound is used as a crude product in the subsequent reaction stages.

LC-MS (Method 3): $R_t$=1.82 min, MS (ES+)=472 (M+H)$^+$

Example 5A

8-Chloro-6-fluoro-1-[(1S,2R)-2-fluorocyclopropyl]-7-[4-(2-morpholin-4-yl-2-oxoethyl)piperazin-1-yl]-4-oxo-1,4-dihydroquinoline-3-carboxylic acid The preparation takes place in analogy to Example 1A from 4-[2-(piperazin-1-yl)acetyl]morpholine and 8-chloro-6,7-difluoro-1-[(1S,2R)-2-fluorocyclopropyl]-4-oxo-1,4-dihydroquinoline-3-carboxylic acid (for preparation see *Journal of Medicinal Chemistry (1994) 37:3344-3352). The compound is used as a crude product in the subsequent reaction stages.

LC-MS (Method 1): $R_t$=1.37 min, MS (ES+)=511 (M+H)$^+$

Example 6A

6-Fluoro-1-[(1R,2S)-2-fluorocyclopropyl]-7-{4-[2-(2-hydroxyethoxy)ethyl]piperazin-1-yl}-8-methoxy-4-oxo-1,4-dihydroquinoline-3-carboxylic acid

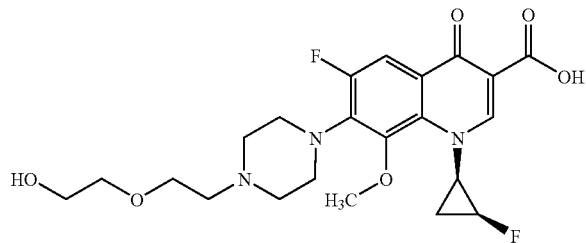

The preparation takes place in analogy to Example 1A from 6,7-difluoro-1-[(1R,2S)-2-fluorocyclopropyl]-8-methoxy-4-oxo-1,4-dihydroquinoline-3-carboxylic acid (for preparation see WO 96/01262). The compound is used as a crude product in the subsequent reaction stages.

LC-MS (Method 3): $R_t$=1.25 min, MS (ES+)=468 (M+H)$^+$

Example 7A

8-Chloro-6-fluoro-1-[(1SR,2RS)-2-fluorocyclopropyl]-7-{4-[2-(2-hydroxyethyl)piperazine-1-yl]-4-oxo-1,4-dihydroquinoline-3-carboxylic acid

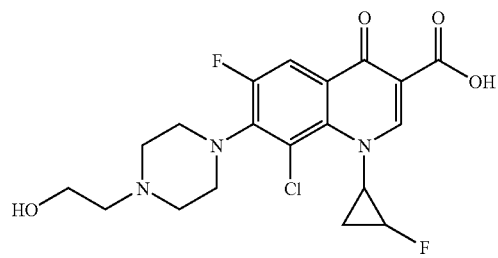

The preparation takes place in analogy to Example 1A from racemic 8-chloro-6,7-difluoro-1-[cis-2-fluorocyclopropyl]-4-oxo-1,4-dihydroquinoline-3-carboxylic acid (for preparation in analogy see Journal of Medicinal Chemistry (1994) 37:3344-3352). The compound is used as crude product in the subsequent reaction stages.

LC-MS (Method 1): $R_t$=1.24 min, MS (ES+)=428 (M+H)$^+$

Example 8A

8-Chloro-6-fluoro-1-[(1SR,2RS)-2-fluorocyclopropyl]-7-(4-methylpiperazin-1-yl)-4-oxo-1,4-dihydroquinoline-3-carboxylic acid

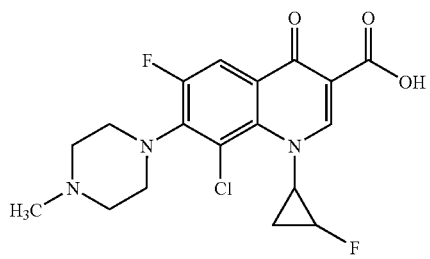

The preparation takes place in analogy to Example 1A from racemic 8-chloro-6,7-difluoro-1-[cis-2-fluorocyclopropyl]-4-oxo-1,4-dihydroquinoline-3-carboxylic acid (for preparation in analogy see Journal of Medicinal Chemistry (1994) 37:3344-3352). The compound is used as a crude product in the subsequent reaction stages.

LC-MS (Method 2): $R_t$=1.01 min, MS (ES+)=398 (M+H)$^+$

Example 9A

8-Chloro-6-fluoro-1-[cis-2-fluorocyclopropyl]-7-{4-[2-(2-hydroxyethoxy)ethyl]piperazine-1-yl}-4-oxo-1,4-dihydroquinoline-3-carboxylic acid

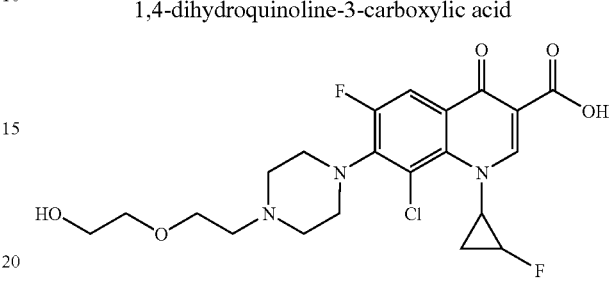

The preparation takes place in analogy to Example 1A from racemic 8-chloro-6,7-difluoro-1-[cis-2-fluorocyclopropyl]-4-oxo-1,4-dihydroquinoline-3-carboxylic acid (for preparation in analogy see Journal of Medicinal Chemistry (1994) 37:3344-3352). The compound is used as a crude product in the subsequent reaction stages.

LC-MS (Method 2): $R_t$=0.99 min, MS (ES+)=472 (M+H)$^+$

Example 10A

1-Cyclopropyl-6-fluoro-7-{4-[2-(2-hydroxyethoxy)ethyl]piperazin-1-yl}-8-methoxy-4-oxo-1,4-dihydroquinoline-3-carboxylic acid

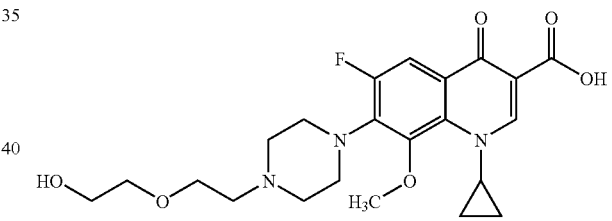

The preparation takes place in analogy to Example 1A from (T-4)-(1-cyclopropyl-6,7-difluoro-1,4-dihydro-8-methoxy-4-oxo-3-quinolinecarboxylato-O3,O4)boron difluoride (for preparation see Journal of Medicinal Chemistry (1995) 38:4478-4487). The compound is used as a crude product in the subsequent reaction stages.

LC-MS (Method 2): $R_t$=0.95 min, MS (ES+)=450 (M+H)$^+$

Example 11A

7-[(3RS,5SR)-3,5-Dimethylpiperazin-1-yl]-6-fluoro-1-[(1R,2S)-2-fluorocyclopropyl]-8-methoxy-4-oxo-1,4-dihydroquinoline-3-carboxylic acid

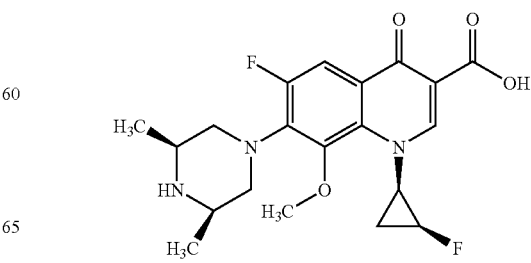

The preparation takes place in analogy to Example 1A from 6,7-difluoro-1-[(1R,2S)-2-fluorocyclopropyl]-8-methoxy-4-oxo-1,4-dihydroquinoline-3-carboxylic acid (for preparation see WO 96/01262).

LC-MS (Method 3): $R_t$=1.38 min, MS (ES+)=408 (M+H)+

Example 12A

1-Cyclopropyl-8-difluoromethoxy-6-fluoro-7-{4-[2-(2-hydroxyethoxy)ethyl]piperazine-1-yl}-4-oxo-1,4-dihydroquinoline-3-carboxylic acid

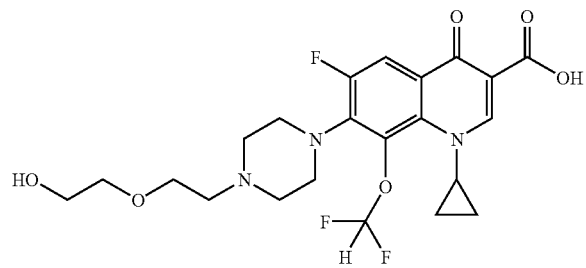

The preparation takes place in analogy to Example 1A from (T-4)-(1-cyclopropyl-8-difluoromethoxy-6,7-difluoro-1,4-dihydro-4-oxo-3-quinolinecarboxylato-O3,O4)boron difluoride (for preparation see EP 352123). The compound is used as a crude product in the subsequent reaction stages.

Example 13A

1-Cyclopropyl-6-fluoro-7-{4-[2-methoxyethyl]piperazin-1-yl}-8-methoxy-4-oxo-1,4-dihydroquinoline-3-carboxylic acid

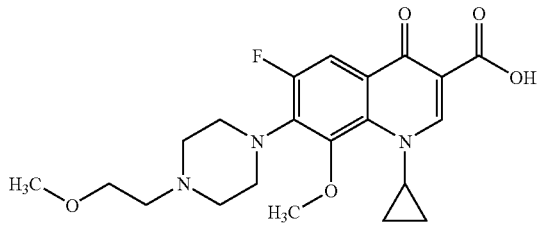

The preparation takes place in analogy to Example 1A from (T-4)-(1-cyclopropyl-6,7-difluoro-1,4-dihydro-8-methoxy-4-oxo-3-quinolinecarboxylato-O3,O4)boron difluoride (for preparation see *Journal of Medicinal Chemistry* (1995) 38:4478-4487). The compound is used as a crude product in the subsequent reaction stages.

$^1$H NMR (300 MHz, DMSO-$d_6$): δ=1.05 (m, 2H), 1.13 (m, 2H), 3.10-3.90 (m, 18 H: in there 3.82 (s, 3H)), 4.18 (m, 1H), 7.82 (d, 1H), 8.73 (s, 1H), 10.78 (bs, 1H).

Example 14A

Ethyl 3-[(2,2,2-trifluoroethyl)amino]-2-(2,4,5-trifluoro-3-methoxybenzoyl)acrylate (E+Z)

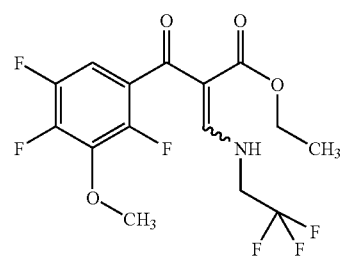

2.00 g (5.79 mmol) of ethyl 3-oxo-3-(2,4,5-trifluoro-3-methoxyphenyl)propanoate are stirred in 3.8 ml (4.14 g, 40.55 mmol) of acetic anhydride and 4.82 ml (4.29 g, 28.96 mmol) of thriethylorthoformate for 2 h under reflux. The solvent is then completely removed on a rotary evaporator and the residue is dissolved in 10 ml of ethanol. 1.03 g (10.43 mmol) of 2,2,2-trifluoro-1-aminoethane are added dropwise to the ice cold solution, the mixture is brought to room temperature and stirred over night at this temperature. For the work-up the solvent is removed and the residue is reacted further as a crude product without purification steps.

LC-MS (Method 2): $R_t$=2.37 min, MS (ES+)=386 (M+H)+.

The following Examples 15A to 22A are prepared in analogy to Example 14A from the corresponding amines.

| Example-No. | Structure | Analytical data LC-MS (Method)/measured values |
|---|---|---|
| 15A (racemic) | 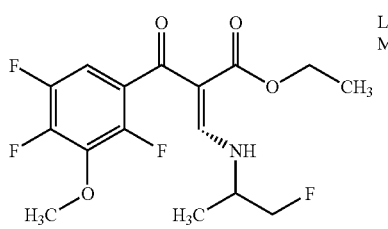 | LC-MS (Method 2): $R_t$ = 2.28 min MS (ES+): m/z = 364 (M + H)+ |

-continued

| Example-No. | Structure | Analytical data LC-MS (Method)/measured values |
|---|---|---|
| 16A (S-enantiomer) | 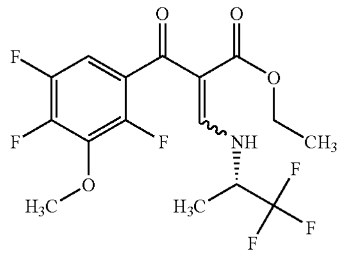 | LC-MS (Method 1): $R_t$ = 2.47 min<br>MS (ES+): m/z = 400 (M + H)$^+$ |
| 17A (R-enantiomer) | 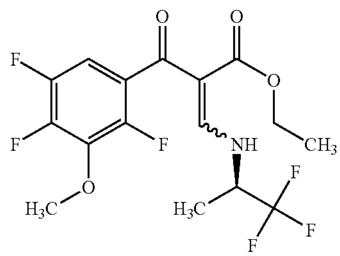 | LC-MS (Method 1): $R_t$ = 2.46 min<br>MS (ES+): m/z = 400 (M + H)$^+$ |
| 18A | 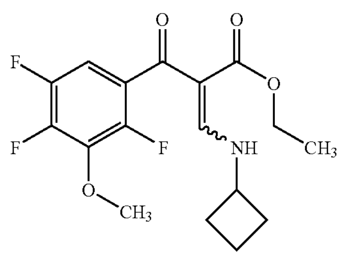 | LC-MS (Method 3): $R_t$ = 2.72 min<br>MS (ES+): m/z = 358 (M + H)$^+$ |
| 19A | 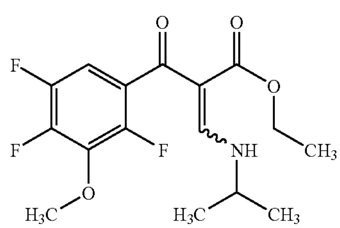 | LC-MS (Method 1): $R_t$ = 2.56 min<br>MS (ES+): m/z = 346 (M + H)$^+$ |
| 20A | 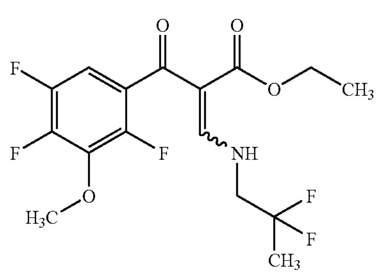 | LC-MS (Method 1): $R_t$ = 2.52 min<br>MS (ES+): m/z = 382 (M + H)$^+$ |
| 21A | 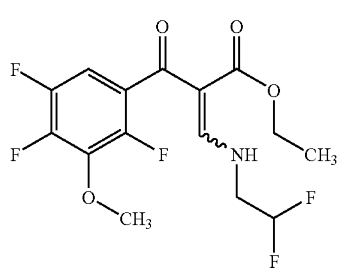 | LC-MS (Method 2): $R_t$ = 2.22 min<br>MS (ES+): m/z = 368 (M + H)$^+$ |

| Example-No. | Structure | Analytical data LC-MS (Method)/measured values |
|---|---|---|
| 22A (1S,2R)- enantiomer | 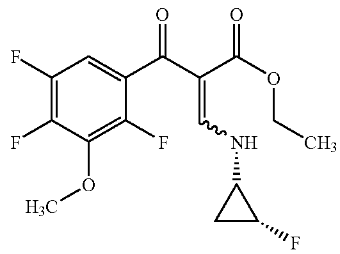 | LC-MS (Method 1): $R_t$ = 2.40 min MS (ES+): m/z = 382 (M + H)$^+$ |

Example 23A

Ethyl 6,7-difluoro-8-methoxy-4-oxo-1-(2,2,2-trifluoroethyl)-1,4-dihydroquinoline-3-carboxylate

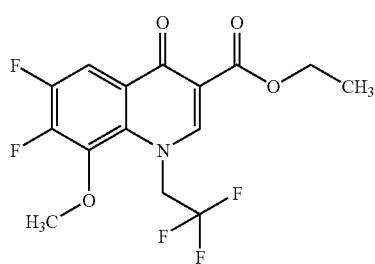

Under an argon atmosphere and ice cooling 0.32 g (8.11 mmol) of 60% sodium hydride are provided in 5 ml of tetrahydrofuran and a solution of 2.23 g (5.79 mmol) of the compound of Example 14A in 15 ml tetrahydrofuran is slowly added dropwise. The mixture is subsequently warmed to room temperature, stirred for 2 h at this temperature and then left standing over night. For the work-up 2 ml of acetic acid are added dropwise and the mixture is stirred for 5 min, diluted with ethyl acetate, washed several times with water and once with a saturated sodium hydrogen carbonate solution, the organic phase is dried over magnesium sulfate, filtered and the solvent is completely removed on a rotary evaporator. The crude product is pre-purified by column chromatography on silica gel 60 (eluent: dichloromethane/methanol 100/1→100/2) and after fine purification by preparative RP-HPLC (Method 5) 1.8 g of product are obtained.

HPLC (Method 10): $R_t$=4.34 min,
MS (DCI (NH$_3$))=366 (M+H)$^+$.
$^1$H NMR (300 MHz, CDCl$_3$): δ=1.41 (t, 3H), 4.15 (s, 3H), 4.41 (q, 2H), 5.23 (q, 2H), 8.11 (dd, 1H), 8.33 (s, 1H).

Examples 24A to 31A listed in the table below are prepared from the corresponding amines in analogy to Example 23A. For the preparation of 2-amino-1-fluoropropane, see *Journal of Organic Chemistry* (1981) 46:4938-4948.

| Example-No. | Structure | Starting material Example No. | Analytical data LC-MS (Method)/measured values HPLC (Method)/measured value MS (Method)/measured value |
|---|---|---|---|
| 24A racemic | 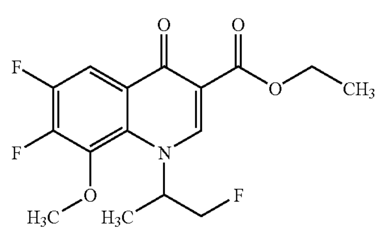 | 15A | HPLC (Method 10): $R_t$ = 4.11 min MS (DCl(NH$_3$)): m/z = 344 (M + H)$^+$ |
| 25A (S)- enantiomer | 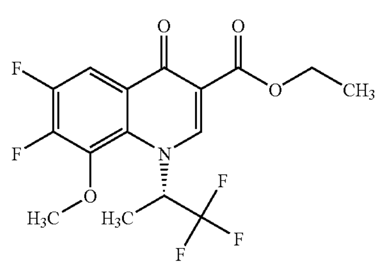 | 16A | LC-MS (Method 1): $R_t$ = 2.22 min MS (ES+): m/z = 380 (M + H)$^+$ |

-continued

| Example-No. | Structure | Starting material Example No. | Analytical data LC-MS (Method)/measured values HPLC (Method)/measured value MS (Method)/measured value |
|---|---|---|---|
| 26A (R)-enantiomer | 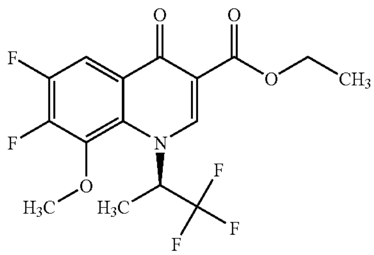 | 17A | LC-MS (Method 1): $R_t$ = 2.22 min<br>MS (ES+): m/z = 380 (M + H)$^+$ |
| 27A | 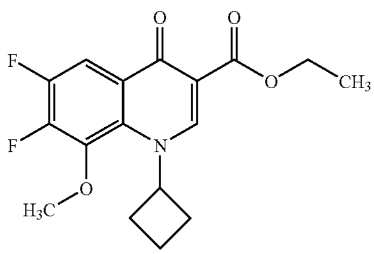 | 18A | LC-MS (Method 3): $R_t$ = 2.33 min<br>MS (ES+): m/z = 338 (M + H)$^+$ |
| 28A | 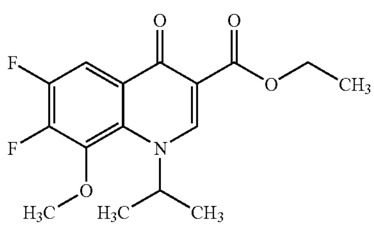 | 19A | LC-MS (Method 1): $R_t$ = 2.16 min<br>MS (ES+): m/z = 326 (M + H)$^+$ |
| 29A | 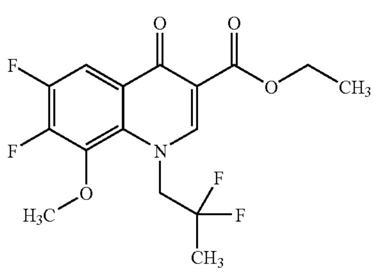 | 20A | LC-MS (Method 1): $R_t$ = 2.11 min<br>MS (ES+): m/z = 362 (M + H)$^+$ |
| 30A | 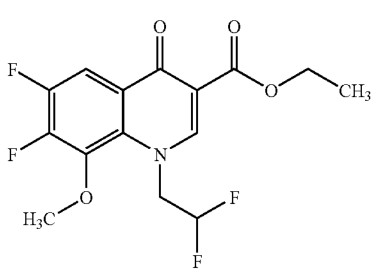 | 1A | LC-MS (Method 2): $R_t$ = 1.83 min<br>MS (ES+): m/z = 348 (M + H)$^+$ |

| Example-No. | Structure | Starting material Example No. | Analytical data LC-MS (Method)/measured values HPLC (Method)/measured value MS (Method)/measured value |
|---|---|---|---|
| 31A (1S,2R)- enantiomer | 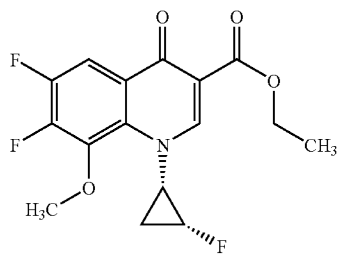 | 22A | LC-MS (Method 2): $R_t$ = 1.76 min MS (ES+): m/z = 342 (M + H)⁺ |

Example 32A

6,7-Difluoro-8-methoxy-4-oxo-1-(2,2,2-trifluoroethyl)-1,4-dihydroquinoline-3-carboxylic acid

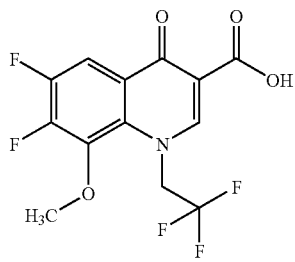

800 mg (2.19 mmol) of the compound of Example 23A are provided in a mixture of 25 ml of acetic acid-water-sulfuric acid 12:8:1 and stirred over night under reflux. For the work-up the solvent is removed to a large extent on a rotary evaporator, the residue is adjusted carefully to pH 3 while cooling with ice with a saturated sodium hydrogen carbonate solution, the suspension is diluted with water, the precipitate is collected by suction filtration and after drying the filter residue under high vacuum, 575 mg of the title compound are obtained.

LC-MS (Method 3): $R_t$=2.41 min, MS (ES+)=338 (M+H)⁺.

¹H NMR (300 MHz, CDCl₃): δ=4.21 (s, 3H), 5.37 (q, 2H), 8.11 (dd, 1H), 8.62 (s, 1H), 14.05 (bs, 1H).

The following Examples 33A bis 40A are prepared in analogy to Example 32A.

| Example-No. | Structure | Starting material | Analytical data LC-MS (Method)/measured values HPLC (Method)/measured value MS (Method)/measured value |
|---|---|---|---|
| 33A racemic | 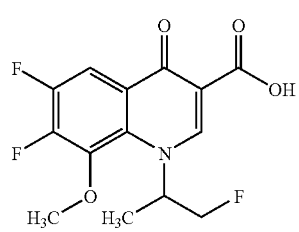 | 24A | HPLC (Method 10): $R_t$ = 4.17 min MS (ESI+): m/z = 316 (M + H)⁺ |
| 34A (S)-enantiomer | 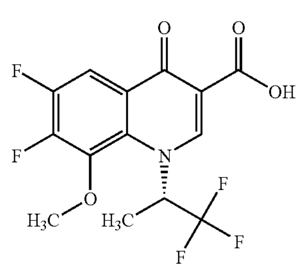 | 25A | HPLC (Method 10): $R_t$ = 4.54 min MS (ESI+): m/z = 374 (M + Na)⁺ |

-continued

| Example-No. | Structure | Starting material | Analytical data<br>LC-MS (Method)/measured values<br>HPLC (Method)/measured value<br>MS (Method)/measured value |
|---|---|---|---|
| 35A<br>(R)-enantiomer | | 26A | LC-MS (Method 3): $R_t$ = 2.47 min<br>MS (ES+): m/z = 352 (M + H)$^+$ |
| 36A | 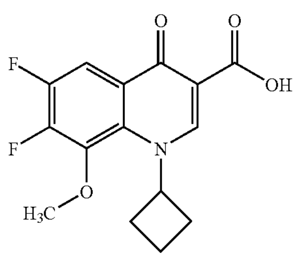 | 7A | LC-MS (Method 3): $R_t$ = 2.35 min<br>MS (ES+): m/z = 310 (M + H)$^+$ |
| 37A | 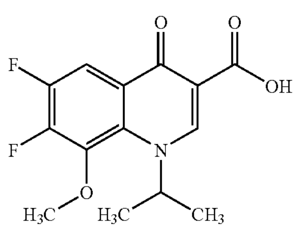 | 28A | LC-MS (Method 3): $R_t$ = 2.27 min<br>MS (ES+): m/z = 298 (M + H)$^+$ |
| 38A | 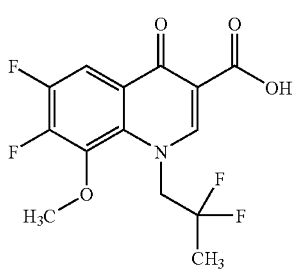 | 29A | LC-MS (Method 1): $R_t$ = 2.22 min<br>MS (ES+): m/z = 334 (M + H)$^+$ |
| 39A | 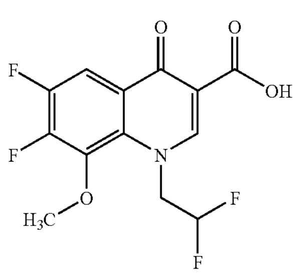 | 30A | HPLC (Method 9): $R_t$ = 4.15 min<br>MS (DCI(NH$_3$)): m/z = 337<br>(M + NH$_4$)$^+$ |

| Example-No. | Structure | Starting material | Analytical data LC-MS (Method)/measured values HPLC (Method)/measured value MS (Method)/measured value |
|---|---|---|---|
| 40A (1S,2R)- enantiomer | 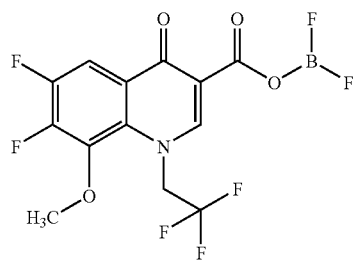 | 31A | LC-MS (Method 2): $R_t$ = 1.84 min MS (ES+): m/z = 313 (M + H)$^+$ |

Example 41A

[6,7-Difluoro-8-methoxy-4-oxo-1-(2,2,2-trifluoroethyl)-1,4-dihydroquinolin-3-yl]carbonyl difluoroborate 1.5 g (4.30 mmol) of the compound of Example 32A are provided in 10 ml of tetrahydrofuran and then 6.81 ml (7.63 g, 53.75 mmol) of borontrifluoride diethylether complex are added and the mixture is stirred at 70° C. over night. For the work-up 50 ml of diethylether are added to the reaction mixture which was cooled to room temperature, the mixture is stirred for 20 min and the precipitate is collected by suction filtration. After drying the residue under high vacuum, 1150 mg of the title compound are obtained and reacted further without purification.

HPLC (Method 9): $R_t$=4.25 min,

MS (DCI (NH$_3$))=402 (M+NH$_4$)$^+$.

$^1$H NMR (300 MHz, DMSO-d$_6$): δ=4.21 (s, 3H), 6.12 (q, 2H), 8.38 (dd, 1H), 9.66 (s, 1H).

The following Examples 42A to 49A are prepared in analogy to Example 41A.

| Example-No. | Structure | Starting material | Analytical data LC-MS (Method)/measured values |
|---|---|---|---|
| 42A | 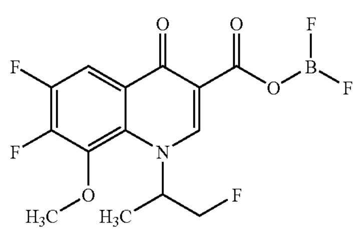 | 33A | LC-MS (Method 1): $R_t$ = 1.96 min MS (ES+): m/z = 364 (M + H)$^+$ |
| 43A (S)-enantiomer | 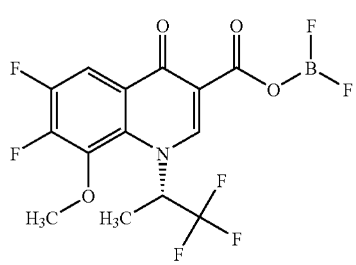 | 34A | LC-MS (Method 2): $R_t$ = 1.98 min MS (ES+): m/z = 400 (M + H)$^+$ |

-continued

| Example-No. | Structure | Starting material | Analytical data LC-MS (Method)/measured values |
|---|---|---|---|
| 44A (R)-enantiomer | 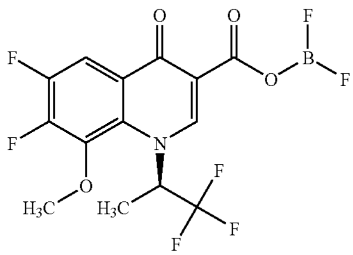 | 35A | LC-MS (Method 2): R$_t$ = 1.98 min MS (ES+): m/z = 400 (M + H)$^+$ |
| 45A | 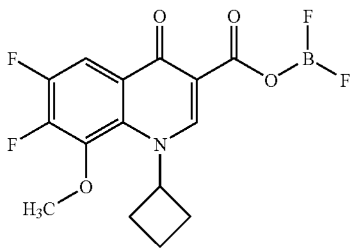 | 36A | LC-MS (Method 1): R$_t$ = 1.92 min MS (ES+): m/z = 358 (M + H)$^+$ |
| 46A | 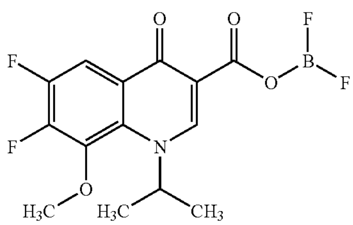 | 37A | LC-MS (Method 3): R$_t$ = 1.83 min MS (ES+): m/z = 346 (M + H)$^+$ |
| 47A | 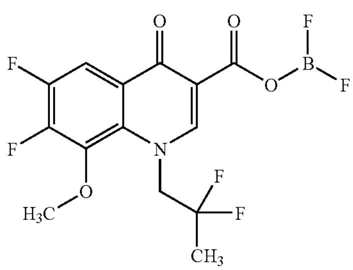 | 38A | LC-MS (Method 2): R$_t$ = 1.89 min MS (ES+): m/z = 382 (M + H)$^+$ |
| 48A | 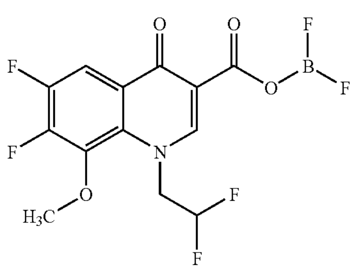 | 39A | LC-MS (Method 3): R$_t$ = 2.09 min MS (ES+): m/z = 368 (M + H)$^+$ |
| 49A (1S,2R)-enantiomer | 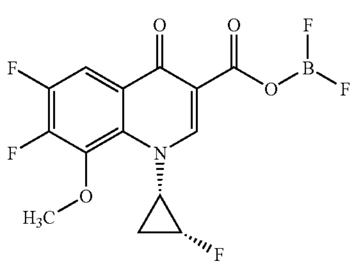 | 40A | LC-MS (Method 2): R$_t$ = 1.74 min MS (ES+): m/z = 361 (M + H)$^+$ |

Example 50A

7-[(3RS,5SR)-3,5-Dimethylpiperazin-1-yl]-6-fluoro-8-methoxy-4-oxo-1-(2,2,2-trifluoroethyl)-1,4-dihydroquinoline-3-carboxylic acid-hydroformate

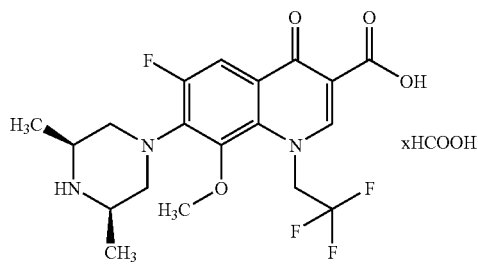

300.0 mg (0.78 mmol) of the compound of Example 41A and 213.6 mg (1.87 mmol) of cis-2,6-dimethylpiperazine are stirred over night at 50° C. in 6 ml of acetonitrile. The solvent is removed completely on a rotary evaporator and the residue is stirred for 1 h under reflux with a mixture of 12 ml of ethanol and 6 ml of triethylamine. For the work-up the solvent is removed on a rotary evaporator and after fine purification by preparative RP-HPLC (method 5) 260 mg of the target compound are obtained.

HPLC (Method 9): $R_t$=3.76 min, MS (ESI+)=432 (M+H)$^+$.

$^1$H NMR (300 MHz, DMSO-d$_6$): δ=1.03 (d, 6H), 2.82 (m, 2H), 3.04 (m, 2H), 3.28 (m, 2H), 3.78 (s, 3H), 5.77 (q, 2H), 7.82 (d, 1H), 8.19 (s, 1H), 8.52 (s, 1H).

The following Examples 51A to 62A are prepared in analogy to Example 50A.

| Example No. | Structure | Starting material | Analytical date LC-MS (Method)/measured values HPLC (Method)/measured value MS (Method)/measured value |
|---|---|---|---|
| 51A racemic | | 42A | LC-MS (Method 9): $R_t$ = 3.67 min MS (ESI+): m/z = 410 (M + H)$^+$ |
| 52A (S)-enantiomer | | 43A | HPLC (Method 10): $R_t$ = 3.76 min MS (ESI+): m/z = 446 (M + H)$^+$ |
| 53A (R)-enantiomer | | 44A | HPLC (Method 10): $R_t$ = 3.77 min MS (ESI+): m/z = 446 (M + H)$^+$ |

-continued

| Example No. | Structure | Starting material | Analytical date<br>LC-MS (Method)/measured values<br>HPLC (Method)/measured value<br>MS (Method)/measured value |
|---|---|---|---|
| 54A | (structure) x CF₃COOH | 45A | LC-MS (Method 2): $R_t$ = 1.16 min<br>MS (ES+): m/z = 404 (M + H)⁺ |
| 55A | (structure) | 46A | HPLC (Method 9): $R_t$ = 3.54 min<br>MS (ESI+): m/z = 392 (M + H)⁺ |
| 56A | (structure) | 47A | LC-MS (Method 2): $R_t$ = 1.10 min<br>MS (ES+): m/z = 428 (M + H)⁺ |
| 57A | (structure) x HCOOH | 48A | HPLC (Method 9): $R_t$ = 3.51 min<br>MS (ESI+): m/z = 414 (M + H)⁺ |
| 58A<br>(1S,2R)-enantiomer | (structure) x HCOOH | 49A | LC-MS (Method 2): $R_t$ = 1.02 min<br>MS (ES+): m/z = 407 (M + H)⁺ |

-continued

| Example No. | Structure | Starting material | Analytical date<br>LC-MS (Method)/measured values<br>HPLC (Method)/measured value<br>MS (Method)/measured value |
|---|---|---|---|
| 59A | 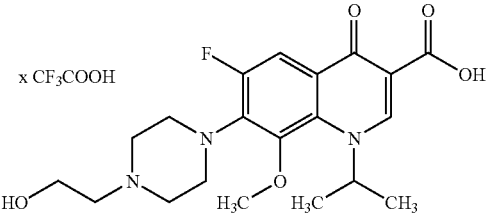 | 46A | HPLC (Method 10): $R_t$ = 3.51 min<br>MS (ESI+): m/z = 408 (M + H)$^+$ |
| 60A | 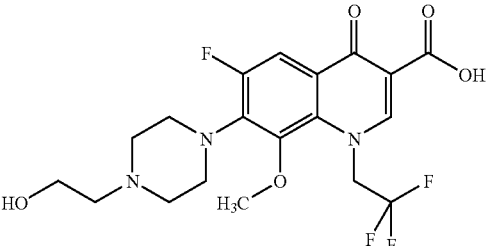 | 41A | HPLC (Method 9): $R_t$ = 3.59 min<br>MS (ESI+): m/z = 448 (M + H)$^+$ |
| 61A<br>racemic | 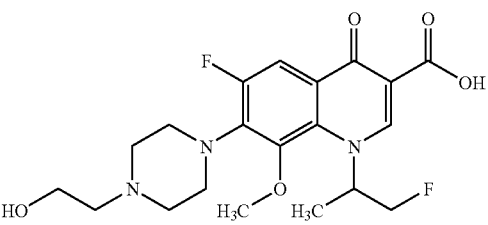 | 42A | HPLC (Method 9): $R_t$ = 3.52 min<br>MS (ESI+): m/z = 426 (M + H)$^+$ |
| 62A | 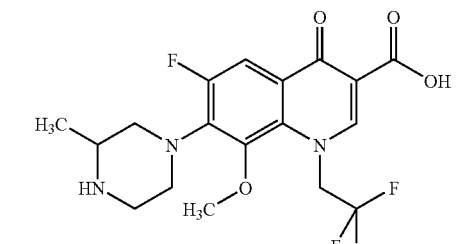 | 41A | LC-MS (Method 2): $R_t$ = 1.14 min<br>MS (ES+): m/z = 418 (M + H)$^+$ |

Example 63A

8-Cyano-1-cyclopropyl-7-[(3RS,5SR)-3,5-dimethylpiperazin-1-yl]-6-fluoro-4-oxo-1,4-dihydroquinoline-3-carboxylic acid-hydrochloride

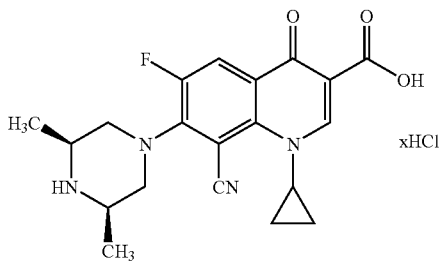

A solution of 500.0 mg (1.63 mmol) of 7-chloro-8-cyano-1-cyclopropyl-6-fluoro-4-oxo-1,4-dihydroquinoline-3-carboxylic acid (for preparation see: DE 19854357) and 446.8 mg (3.91 mmol) of cis-2,6-dimethylpiperazine in 50 ml of acetonitrile is stirred over night at 50° C. The solvent is removed completely on a rotary evaporator, the residue is taken up in 50 ml of water and the pH is adjusted to pH 11 with a 1N sodium hydroxide solution (the residue dissolves). The solution is then adjusted to pH 7 with 1N hydrochloric acid. The precipitate is filtered off, washed with water and diethylether and dried under high vacuum. 157 mg of the title compound are obtained. The filtrate is extracted with dichloromethane, the organic phase is concentrated and the residue is purified by RP-HPLC. An additional 351 mg of the title compound are obtained.

LC-MS (Method 2): $R_t$=0.83 min, MS (ES+): m/z=385 (M+H)$^+$.

Example 64A

2-Chloro-4-methoxybenzonitrile

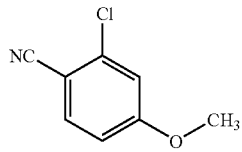

2.6 g of sodium hydride (60% in oil) are added to 2.0 g of 2-chloro-4-hydroxybenzonitrile in 50 ml of THF under argon at 0° C. After 10 min 9.24 g of methyliodide are added and the mixture is stirred over night at room temperature. For the work-up 2 ml of glacial acidic acid are added cautiously, the mixture is concentrated on a rotary evaporator and the residue is subjected to an extractive work-up with 1N hydrochloric acid and ethyl acetate. The organic phase is dried with sodium sulfate and concentrated on a rotary evaporator. After HPLC purification (method 5) 0.70 g of product are obtained.

MS (DCI/NH$_3$): m/z=184.9 (M+NH$_4$)$^+$.

$^1$H NMR (300 MHz, CDCl$_3$): δ=7.58 (d, 1H), 7.01 (d, 1H), 6.87 (dd, 1H).

Example 65A

2-Bromo-4-chlorobenzonitrile

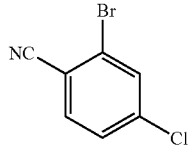

588 mg of 2-bromo-4-chlorobenzoic acid and 300 mg of urea are dissolved in dichloromethane/methanole and deposited onto 364 mg of aluminum oxide on a rotary evaporator. The residue is irradiated for 60 min in a microwave at 150° C. After cooling the residue is stirred with ethyl acetate and water, the mixture is filtered and the aqueous phase is removed. The organic phase is washed with a sodium hydrogencarbonate solution dried over sodium sulfate, concentrated on a rotary evaporator and then dried under high vacuum. The product is reacted further without additional purification.

$^1$H NMR (300 MHz, CDCl$_3$): δ=7.72 (d, 1H), 7.60 (d, 1H), 7.42 (dd, 1H).

Example 66A

2-Chloro-4-(trifluoromethoxy)phenyl trifluoromethylsulfonate

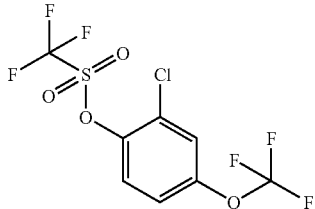

4.00 g of 2-chloro-4-trifluoromethoxyphenol are provided in 50 ml of toluene and 50 ml of a 30% solution of potassium phosphate in water at 0° C., 3.82 ml of trifluoromethanesulfonic anhydride are added slowly and the mixture is stirred for 1.5 h at room temperature. The aqueous phase is removed and the organic phase is washed with water, dried over sodium sulfate and concentrated. The crude product is reacted onto Example 67A without purification.

Example 67A

2-Chloro-4-(trifluoromethoxy)benzonitrile

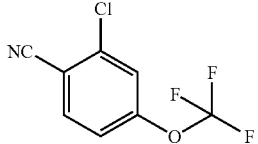

3.00 g of the compound of Example 66A are dissolved with 2.04 g of zinc cyanide and 1.00 g of tetrakis(triphenylphosphine)palladium in 12 of ml degased DMF and heated under argon for 2 h at 120° C. After cooling the reaction mixture is diluted with ethyl acetate and extracted twice with a saturated sodium hydrogencarbonate solution and then a saturated sodium chloride solution. The organic phase is dried over sodium sulfate and concentrated. The residue is purified by silica gel chromatography (cyclohexane/ethyl acetate 10:1).

$^1$H NMR (300 MHz, DMSO-d$_6$): δ=7.62 (dd, 1H), 7.95 (d, 1H), 8.18 (d, 1H).

Example 68A

2-Methyl-4-(trifluoromethoxy)benzamide

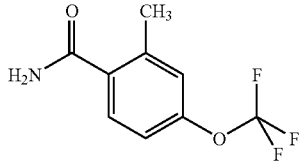

795 mg (3.61 mmol) of 2-methyl-4-(trifluoromethoxy) benzoic acid are heated with 4 ml (54.8 mmol) of thionyl chloride and a drop of DMF for 30 min under reflux. After cooling the reaction mixture is added slowly dropwise into an ice-cooled concentrated aqueous ammonia solution. The resulting precipitate is collected by suction filtration, taken up in 30 ml of water and stirred for 1 h at 60° C. The reaction mixture is left to cool, the solid is collected by filtration and dried under vacuum. Yield: 562 mg (71% of theory)

LC-MS (Method 2): R$_t$=1.61 min, MS (ESI+): m/z=220 (M+H)$^+$ $^1$H NMR (400 MHz, DMSO-d$_6$): δ=7.79 (bs, 1H), 7.42-7.50 (m, 2H), 7.19-7.28 (m, 2H), 2.39 (s, 3H).

Example 69A

2-Methyl-4-(trifluoromethoxy)benzylamine

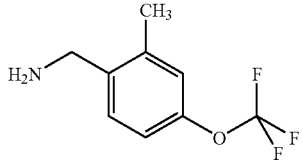

18.8 ml (18.8 mmol) of borane-THF-complex (1M) are provided under argon and ice cooling. A solution of 823 mg (3.76 mmol) of 2-methyl-4-(trifluoromethoxy)benzamide (Example 68A) in 80 ml of THF is added dropwise and the reaction mixture is subsequently stirred for 8 h under reflux. Under ice cooling 80 ml of 1N hydrochloric acid are added dropwise (until the end of the evolution of gas) and the reaction mixture is heated for 1 h under reflux. The reaction mixture is subsequently adjusted to an alkaline pH with a 1N sodium hydroxide solution, extracted three times with dichloromethane and the combined organic phases are dried over sodium sulfate and the solvent is removed under vacuum. An oil is obtained which is reacted further without further purification. Yield: 732 mg (95% of theory).

LC-MS (Method 3): $R_t$=1.41 min, MS (ESI+): m/z=206 (M+H)$^+$ $^1$H NMR (400 MHz, CDCl$_3$): δ=7.32-7.40 (m, 1H), 6.99-7.11 (m, 2H), 3.95-4.01 (m, 2H), 2.40 (s, 3H).

Example 70A

2-Bromo-4-chlorobenzylamine

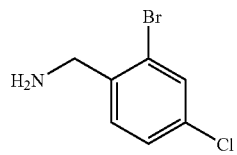

13.9 ml of borane-THF complex are provided under ice cooling. A solution of 2.0 g of 2-bromo-4-chlorobenzonitrile (Example 65A) in 60 ml of THF is added slowly. The reaction mixture is then heated for 1 h under reflux, cooled and under ice cooling 20 ml of 1N hydrochloric acid are added dropwise. The mixture is heated under reflux for 1 h and left to cool. For the work-up the solution is adjusted to an alkaline pH with a 1N sodium hydroxide solution and extracted with dichloromethane. The organic phase is dried over sodium sulfate and concentrated on a rotary evaporator. The crude product is reacted further without purification.

$^1$H NMR (300 MHz, CDCl$_3$): δ=3.89(s, 2H), 7.35-7.45 (m [ABM], 2H), 7.55 (d, 1H).

Example 71A

4-Bromo-2-chlorobenzylamine hydrochloride

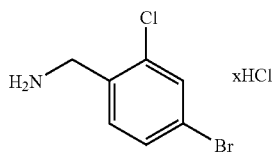

46.2 ml of borane-THF complex are provided under ice cooling. A solution of 2.0 g of 4-bromo-4-chlorobenzonitrile in 240 ml of THF is added slowly. The reaction mixture is then heated for 1 h under reflux, cooled and 20 ml of 1N hydrochloric acid are added dropwise while cooling on ice. The mixture is heated under reflux for 1 h and left to cool. For the work-up the solution is adjusted to an alkaline pH with a 1N sodium hydroxide solution and extracted with dichloromethane. The organic phase is dried over sodium sulfate and concentrated on a rotary evaporator. 6 ml of hydrochloric acid in dioxane (4N) are added and the precipitated hydrochloride is collected by suction filtration. 1.3 g of product are obtained.

$^1$H NMR (300 MHz, DMSO-d$_6$): δ=4.09 (s, 2H), 7.58 (dd, 1H), 7.68 (dd, 1H), 7.83 (d, 1H), 8.55 (bs, 3H).

Example 72A

4-Bromo-2-methylbenzylamine

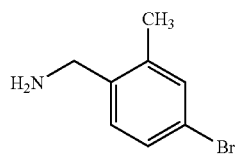

The preparation takes place in analogy to Example 70A from 4-bromo-2-methyl-benzonitrile.

$^1$H NMR (300 MHz, CDCl$_3$): δ=ca. 1.7 (br.s, NH2), 2.60 (s, 3H), 3.81 (s, 2H), 7.19 (d, 1H), 7.28 (s, 1H), 7.30 (d, 1H).

Example 73A

2-Chloro-4-methoxybenzalamine hydrochloride

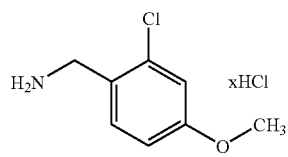

The preparation takes place in analogy to Example 71A from the compound of Example 64A.

$^1$H NMR (300 MHz, DMSO-d$_6$): δ=3.80 (s, 3H), 4.04 (s, 2H), 7.01 (dd, 1H), 7.12 (d, 1H), 7.53 (d, 1H), 8.38 (bs, 3H).

Example 74A

2-Chloro-4-trifluoromethoxybenzylamine hydrochloride

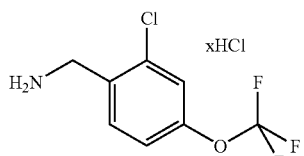

The preparation takes place in analogy to Example 71A from the compound of Example 67A.

$^1$H NMR (300 MHz, DMSO-d$_6$): δ=4.15 (s, 2H), 7.52 (d, 1H), 7.70 (s, 1H), 7.78 (d, 1H), 8.56 (bs, 3H).

Example 75A

2-Chloro-4-trifluoromethylbenzylamine hydrochloride

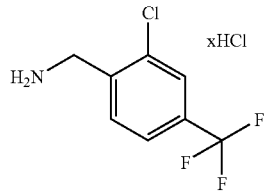

The preparation takes place in analogy to Example 71A from 2-chloro-4-trifluoromethylbenzonitrile.

$^1$H NMR (300 MHz, DMSO-d$_6$): δ=4.22 (s, 2H), 7.30-7.90 (m [AB], 2H), 7.40 (s, 1H), 8.00 (s, 1H), 8.60 (bs, 3H).

Example 76A 2,4-Dichloro-6-methylbenzylamine hydrochloride

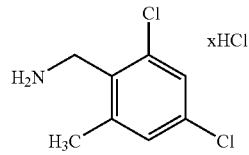

The preparation takes place in analogy to Example 71A from 2,4-dichloro-6-methylbenzonitrile.

$^1$H NMR (300 MHz, DMSO-d$_6$): δ=2.5 (s, 3H), 4.10 (s, 2H), 7.40 (s, 1H), 7.60 (s, 1H), 8.40 (bs, 3H).

LC-MS (Method 13): R$_t$=2.44 min, MS (ES+)=190 (M+H)$^+$.

Example 77A

4-Chloro-2-trifluoromethylbenzylamine hydrochloride

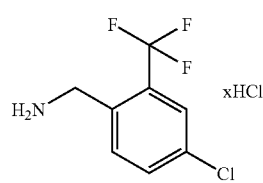

The preparation takes place in analogy to Example 71A from 4-chloro-2-trifluoromethyl-benzonitrile.

$^1$H NMR (300 MHz, DMSO-d$_6$): δ=4.18 (d, 2H), 7.82 (d, 1H), 7.88-7.98 (m, 2H), 8.58 (bs, 3H).

Example 78A

2-Methyl-4-trifluoromethylbenzylamine hydrochloride

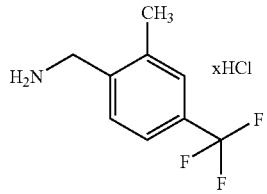

The preparation takes place in analogy to Example 71A from 2-methyl-4-trifluoromethylbenzonitrile.

$^1$H NMR (400 MHz, DMSO-d$_6$): δ=2.44 (s, 3H), 4.10 (s, 2H), 7.52 (s, 3H), 8.55 (bs, 3H).

Example 79A

8-Chloro-1-cyclopropyl-N-(2,4-dichlorobenzyl)-6,7-difluoro-4-oxo-1,4-dihydroquinoline-3-carboxamide

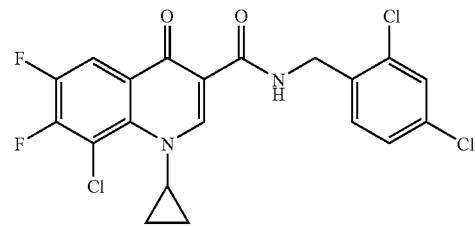

15.0 g of 8-chloro-1-cyclopropyl-6,7-difluoro-4-oxo-1,4-dihydroquinoline-3-carboxylic acid (for preparation see DE 3420743 or Y. Kimura et al., *J. Med. Chem.* (1994) 37:3344) are dissolved in 500 ml of DMF and 31.3 g of PyBOP and 10.6 g of 2,4-dichlorobenzylamine are added. After a day the solvent is removed and the residue is purified by flash chromatography on silica gel (toluene/ethyl acetate 95:5).

LC-MS (Method 1): R$_t$=3.10 min, MS (ES+)=457 (M+H)$^+$.

Example 80A

7-[(3R,5S)-4-(Chloroacetyl)-3,5-dimethylpiperazin-1-yl]-1-cyclopropyl-N-(2,4-dichlorobenzyl)-6-fluoro-8-methoxy-4-oxo-1,4-dihydroquinoline-3-carboxamide

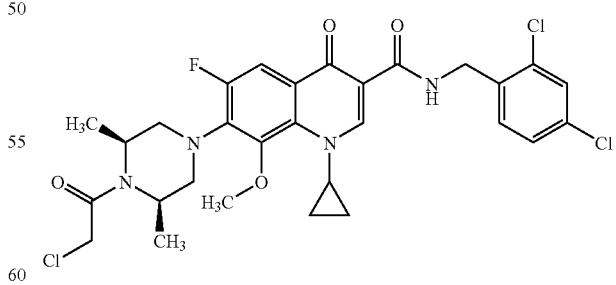

0.17 ml (0.25 g, 2.19 mmol) of chloroacetyl chloride are provided in 5 ml of dichloromethane, the solution is cooled to 0° C., and subsequently 1.00 g (1.83 mmol) of the compound of Example 12 are added, the mixture is warmed to room temperature and stirred for 1 h at this temperature. For the work-up 0.49 g of the target compound are isolated from the solution by negative pressure column chromatography on silica gel 60 with an eluent mixture of dichloromethane:ethanol 95:5.

LC-MS (Method 3): $R_t$=3.05 min, MS (ES+)=623 (M+H)$^+$.

$^1$H NMR (400 MHz, DMSO-$d_6$): δ=0.95 (m, 2H), 1.09 (m, 2H), 1.40 (m, 6H), 3.28 (m, 2H), 3.69 (s, 3H), 4.03-4.70 (m, 9H: in there 4.58 (d, 2H)), 7.35-7.47 (m, 2H), 7.63 (d, 1H), 7.78 (d, 1H), 8.69 (s, 1H), 10.25 (t, 1H).

Example 81A

7-[(3RS,5SR)-4-(Chloroacetyl)-3,5-dimethylpiperazin-1-yl]-N-(2,4-dichlorobenzyl)-6-fluoro-8-methoxy-1-(2,2,2-trifluoroethyl)-4-oxo-1,4-dihydroquinoline-3-carboxamide

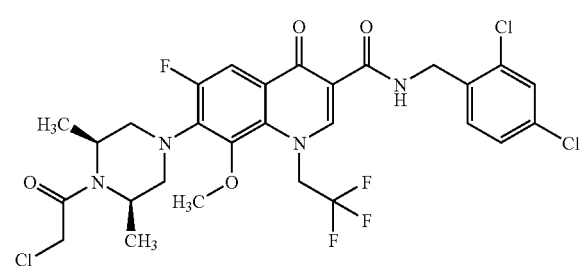

In analogy to Example 80A the title compound is obtained from the compound of Example 47.

LC-MS (Method 2): $R_t$=2.91 min, MS (ES+)=666 (M+H)$^+$.

Example 82A

7-[(3RS,5SR)-4-(Azidoacetyl)-3,5-dimethylpiperazin-1-yl]-1-cyclopropyl-N-(2,4-dichlorobenzyl)-6-fluoro-8-methoxy-4-oxo-1,4-dihydroquinoline-3-carboxamide hydrochloride

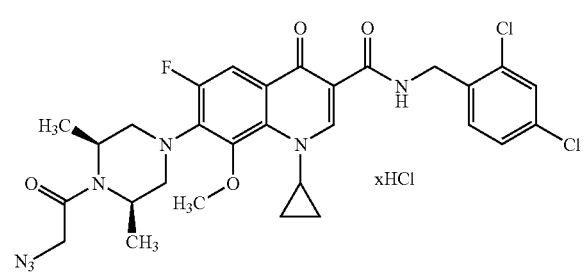

50.0 mg of the compound of Example 80A and 15.6 mg (0.24 mmol) of sodium azide are stirred in 3 ml of N,N-dimethylformamide in a closed reaction vessel at 90° C. over night. After fine purification by preparative RP-HPLC (Method 6) 46 mg of the target compound are obtained.

LC-MS (Method 1): $R_t$=3.03 min, MS (ES+)=630 (M+H)$^+$.

Example 83A

7-[(3RS,5SR)-4-(Azidoacetyl)-3,5-dimethylpiperazin-1-yl]-N-(2,4-dichlorobenzyl)-6-fluoro-8-methoxy-1-(2,2,2-trifluoroethyl)-4-oxo-1 4-dihydroquinoline-3-carboxamide

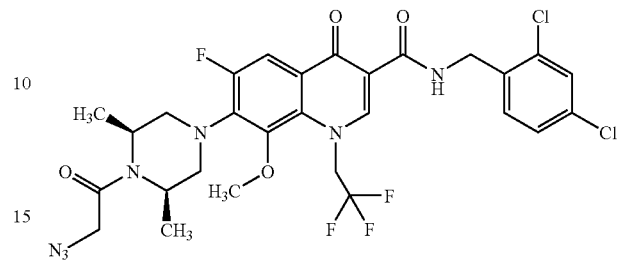

In analogy to Example 82A but at room temperature in the presence of 0.1 eq. of potassium iodide the title compound is prepared from the compound of Example 81A.

LC-MS (Method 3): $R_t$=3.17 min, MS (ES+): m/z=671 (M+H)$^+$.

Example 84A

Ethyl 4-[3-{1-cyclopropyl-[(2,4-dichlorobenzyl)amino]carbonyl}-1-fluoro-8-methoxy-4-oxo-1,4-dihydroquinolin-7-yl]-(2RS,6SR)-2,6-dimethylpiperazin-1-yl}ethanoate hydrochloride

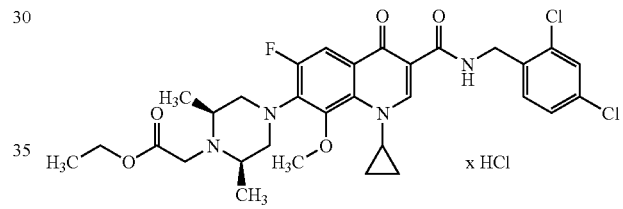

1 g of the compound of Example 12 is heated with 343 mg of ethyibromoacetate, 312 mg of potassium iodide and 590 mg of potassium carbonate in 60 ml of acetonitrile for 2 h under reflux. After cooling the reaction mixture is separated by preparative HPLC (Method 6). 862 mg (75% of theory) of the title compound are obtained.

LC-MS (Method 2): $R_t$=2.39 min. MS (ESI): m/z=633 (M+H)$^+$.

$^1$H NMR (400 MHz, DMSO-$d_6$): δ=0.98 (m, 2H), 1.12 (m, 2H), 1.29 (t, 3H), 1.33 (d, 6H), 3.35-3.69 (m, 4H), 3.72-3.90 (m, 5H: in there 3.79 (s, 3H)), 4.11 (m, 1H), 4.23-4.51 (m, 4H: in there 4.29 (q, 2H)), 4.59 (d, 2H), 7.39 (d, 1H), 7.42 (dd, 1H), 7.53 (d, 1H), 7.78 (d, 1H), 8.69 (s, 1H), 10.22 (t, 1H).

Example 85A

4-[3-{1-Cyclopropyl-[(2,4-dichlorobenzylamino]carbonyl}-1-fluoro-8-methoxy-4-oxo-1,4-dihydroquinolin-7-yl]-(2RS,6SR)-2,6-dimethylpiperazin-1-yl}ethanoic acid

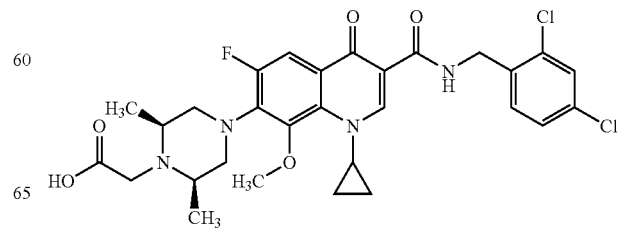

200 mg of the compound of Example 84A are dissolved in 5 ml of dioxane, subsequently 5 ml of a 1M lithium hydroxide solution are added and the mixture is stirred for 2 h at 50° C. For the work-up the solvent is removed on a rotary evaporator and the residue is taken up in water and acidified with 1M hydrochloric acid (pH 3-4). The precipitate is collected by filtration, washed with water and dried under high vacuum. 140 mg (73% of theory) of the title compound are obtained.

LC-MS (Method 1): $R_t$=2.06 min, MS (ESI): m/z=605 (M+H)$^+$.

$^1$H NMR (300 MHz, DMSO-d$_6$): δ=0.99 (m, 2H), 1.18 (m, 2H), 1.38 (d, 6H), 3.46 (m, 2H), 3.55 (m, 2H), 3.70 (s, 3H), 3.78 (m, 4H), 3.95 (m, 1H), 4.68 (d, 2H), 7.20 (dd, 1H), 7.38 (m, 2H), 7.86 (d, 1H), 1H), 8.84 (s, 1H), 10.28 (t, 1H).

Example 86A

7-[(3RS,5SR)-4-(Chloroacetyl)-3,5-dimethylpiperazin-1-yl]-6-fluoro-8-methoxy-N-[2-methyl-4-(trifluoromethoxy)benzyl]-1-(2,2,2-trifluoroethyl)-4-oxo-1,4-dihydroquinoline-3-carboxamide

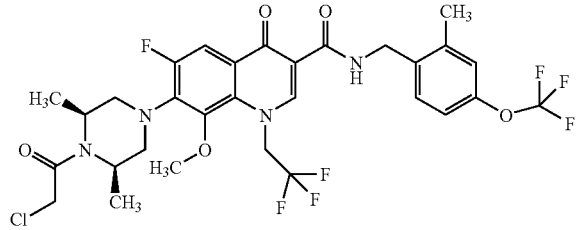

The title compound is prepared in analogy to Example 80A from the compound of Example 52.

LC-MS (Method 1): $R_t$=3.09 min, MS (ES+): m/z=695 (M+H)$^+$.

Example 87A

7-[(3RS,5SR)-4-(Azidoacetyl)-3,5-dimethylpiperazin-1-yl]-6-fluoro-8-methoxy-N-[2-methyl-4-(trifluoromethoxy)benzyl]-1-(2,2,2-trifluoroethyl)-4-oxo-1,4-dihydroquinoline-3-carboxamide

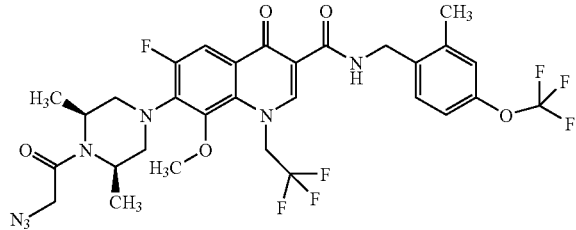

The title compound is prepared in analogy to Example 82A from the compound of Example 86A.

LC-MS (Method 3): $R_t$=3.15 min, MS (ES+): m/z=702 (M+H)$^+$.

$^1$H NMR (400 MHz, CDCl$_3$): δ=1.51 (d, 6H), 2.40 (s, 3H), 3.30 (d, 2H), 3.44 (br.d, 2H), 3.75 (s, 3H), 4.00 (br.s, 2H), 4.62 (d, 2H), 5.20 (q, 2H), 7.00-7.06 (m, 2H), 7.35 (d, 1H), 7.95 (d, 1H), 8.60 (s, 1H), 9.99 (t, 1H).

Exemplary Embodiments

Example 1

8-Chloro-1-cyclopropyl-N-(2,4-dichlorobenzyl)-6-fluoro-7-[4-(2-hydroxyethyl)-1,4-diazepan-1-yl]-4-oxo-1,4-dihydroquinoline-3-carboxamide

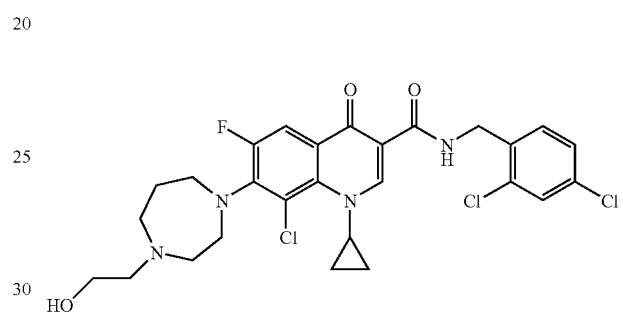

110 mg (0.26 mmol) of the compound of Example 1A are dissolved in 2 ml of dimethylformamide and 35 mg (0.26 mmol) of 1-hydroxybenzotriazole, 46 mg (0.26 mmol) of 2,4-dichlorobenzylamine and 55 mg (0.29 mmol) of N-(3-dimethylaminopropyl)-N'-ethylcarbodiimide hydrochloride are added. After two days of stirring at room temperature the batch is diluted with 2 ml of water. The batch is purified by preparative HPLC (Method 4). 34.5 mg of the target compound are obtained.

LC-MS (Method 3): $R_t$=1.95 min, MS (ES+)=581 (M+H)$^+$

In analogy to the preparation instructions of Example 1, Examples 2 to 6 are prepared:

Example 2

8-Chloro-1-cyclopropyl-N-(2,4-dichlorobenzyl)-6-fluoro-7{4-[2-(2-hydroxyethoxy)ethyl]piperazin-1-yl}-4-oxo-1,4-dihydroquinoline-3-carboxamide

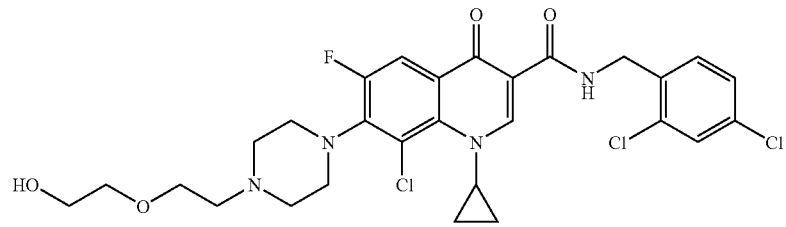

The preparation takes place in analogy to Example 1 from Example 2A.

LC-MS (Method 2): $R_t$=1.78 min, MS (ES+)=611 (M+H)$^+$ $^1$H NMR (300 MHz, DMSO-d$_6$): δ=0.9 (m, 2H), 1.2 (m, 2H), 2.6-2.7 (m, about 6H), 3.3 (signals under the solvent), 3.4-3.6 (m, about 6H), 4.3 (m, 1H), 4.5 (d, 2H), 7.4 (m, 2H), 7.65 (d, 1H), 7.9 (d, 1H), 8.8 (s, 1H), 10.1 (t, 1H).

Example 3

8-Chloro-N-(2,4-dichlorobenzyl)-6-fluoro-1-[(1R,2S)-2-fluorocyclopropyl]-7-{4-[2-(2-hydroxyethoxy)ethyl]piperazin-1-yl}-4-oxo-1 4-dihydroquinoline-3-carboxamide

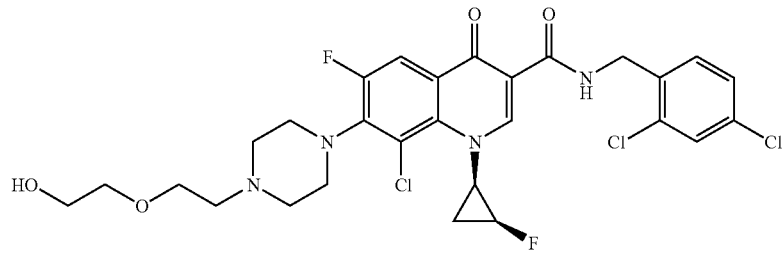

The preparation takes place in analogy to Example 1 from Example 3A.

LC-MS (Method 2): $R_t$=1.76 min, MS (ES+) 629 (M+H)$^+$

Example 4

8-Chloro-N-(2,4-dichlorobenzyl)-6-fluoro-1-[(1S,2R)-2-fluorocyclopropyl]-7-{4-[2-(2-hydroxyethoxy)ethyl]piperazin-1-yl} -4-oxo-1,4-dihydroquinoline-3-carboxamide

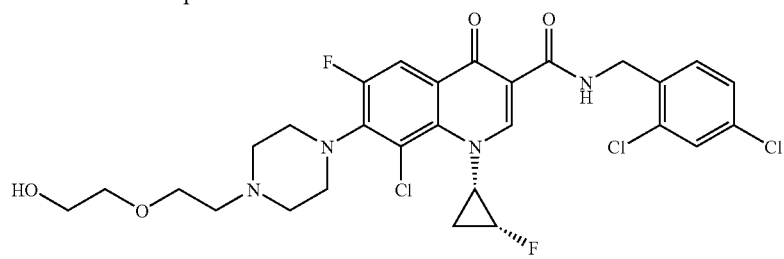

The preparation takes place in analogy to Example 1 from Example 4A.

LC-MS (Method 1): $R_t$=1.98 min. MS (ES+)=629 (M+H)$^+$

Example 5

8-Chloro-1-cyclopropyl-N-(2,4-dichlorobenzyl)-7-[(3RS,5SR)-3,5-dimethylpipierazin-1-yl]-6-fluoro-4-oxo-1,4-dihydroquinoline-3-carboxamide

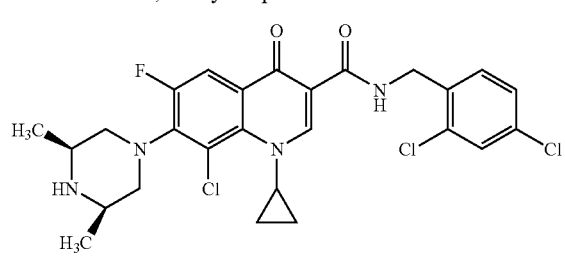

The preparation takes place in analogy to Example 1 from 8-chloro-1-cyclopropyl-7-[(3RS,5SR)-3,5-dimethylpiperazin-1-yl]-6-fluoro-4-oxo-1,4-dihydroquinoline-3-carboxylic acid (for preparation see DE 3635218)

LC-MS (Method 2): $R_t$=1.86 min, MS (ES+)=551 (M+H)$^+$ $^1$H NMR (400 MHz, CDCl$_3$): δ=0.9 (m, 2H), 1.11 (d, 6H), 1.2-1.3 (m, 2H), 2.7-2.9 (m, 2H), 3.1-3.3 (m, 4H), 4.3 (m, 1H), 4.7 (d, 2H), 7.2 (dd, 2H), 7.4 (m, 2H), 8.0 (d, 1H), 8.9 (s, 1H), 10.2 (t, 1H).

Example 6

8-Chloro-N-(2,4-dichlorobenzyl)-6-fluoro-1-[(1S,2R)-2-fluorocyclopropyl]-7-[4-(2-morpholin-4-yl-2-oxoethyl)piperazin-1-yl]-4-oxo-1,4-dihydroquinoline-3-carboxamide

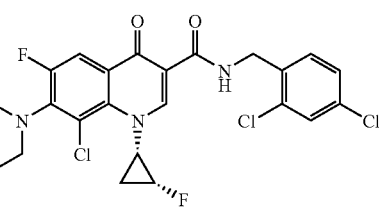

The preparation takes place in analogy to Example 1 from Example 5A.

LC-MS (Method 1): $R_t$=2.08 min. MS (ES+)=668 (M+H)$^+$

Example 7

N-(2,4-Dichlorobenzyl)-6-fluoro-1-[(1R,2S)-2-fluorocyclopropyl]-7-{4-[2-(2-hydroxyethoxy)ethyl]piperazin-1-yl}-8-methoxy-4-oxo-1,4-dihydroquinoline-3-carboxamide

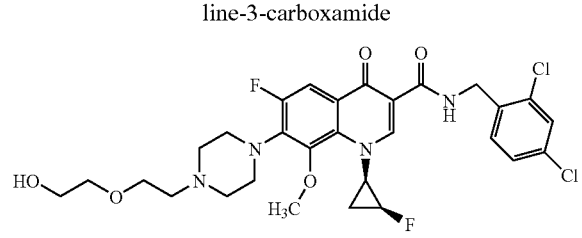

140 mg (0.27 mmol) of 1-benzotriazolyloxytripyrrolidinophosphonium hexafluorophosphate, 47 mg (0.27 mmol) of 2,4-dichlorobenzylamine and 35 mg (0.27 mmol) of diisopropylethylamine are added under argon to 105 mg (0.14 mmol) of the carboxylic acid of Example 6A in 2 ml of dimethylformamide and the mixture is stirred at room temperature for 2 days. The reaction mixture is diluted with 2 ml of water and without further work-up purified by preparative HPLC (Method 4). 52 mg of the target compound are obtained.

LC-MS (Method 1): $R_t$=1.91 min, MS (ES+)=625 (M+H)$^+$

In analogy to the preparation instructions of Example 7, Examples 8 to 18 are prepared:

Example 8

8-Chloro-N-(4-chloro-2-methylbenzyl)-1-cyclopropyl-6-fluoro-7-{4-[2-(2-hydroxyethoxy)ethyl]piperazin-1-yl}-4-oxo-1,4-dihydroquinoline-3-carboxamide

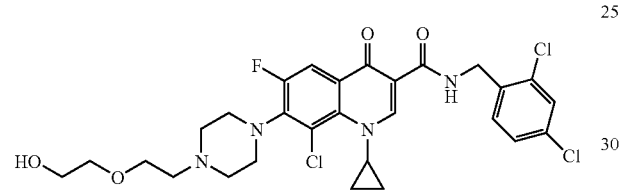

The preparation takes place in analogy to Example 7 from Example 2A.

LC-MS (Method 3): $R_t$=1.91 min, MS (ES+)=591 (M+H)$^+$ $^1$H NMR (400 MHz, CDCl$_3$): δ=0.9 (m, 2H), 1.2 (m, 2H), 2.4 (s, 3H), 2.6-2.7 (m, about 6H), 3.4 (m, about 4H), 3.6-3.8 (m, 6H), 4.2 (m, 1H), 4.6 (d, 2H), 7.2 (m, 2H), 7.35 (dd, 2H), 7.9 (d, 1H), 8.9 (s, 1H), 10.0 (t, 1H).

Example 9

8-Chloro-N-(2,4-dichlorobenzyl)-6-fluoro-1-[(1SR,2RS)-2-fluorocyclopropl]-7-{4-[2-(2-hydroxyethyl)piperazin-1-yl]-4-oxo-1,4-dihydroquinoline-3-carboxamide

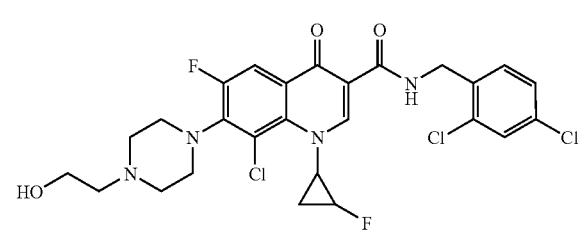

The preparation takes place in analogy to Example 7 from Example 7A.

LC-MS (Method 2): $R_t$=1.63 min, MS (ES+)=585 (M+H)$^+$

Example 10

Chloro-N-(2,4-dichlorobenzyl)-6-fluoro-1-[(1SR,2RS)-2-fluorocyclopropyl]-7-(4-methylpiperazin-1-yl)-4-oxo-1,4-dihydroquinoline-3-carboxamide

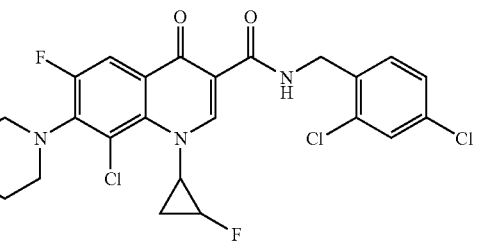

The preparation takes place in analogy to Example 7 from Example 8A.

LC-MS (Method 2): $R_t$=1.70 min, MS (ES+)=555 (M+H)$^+$

Example 11

Chloro-N-(2,4-dichlorobenzyl)-6-fluoro-1-[(1SR,2RS)-2-fluorocyclopropyl]-7-{4-[2-hydroxyethoxy)ethyl]piperazin-1-yl}-4-oxo-1,4-dihydroquinoline-3-carboxamide

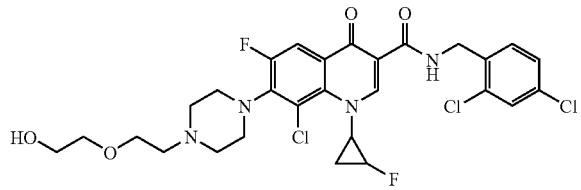

The preparation takes place in analogy to Example 7 from Example 9A.

LC-MS (Method 3): $R_t$=1.89 min, MS (ES+)=629 (M+H)$^+$

Example 12

1-Cyclopropyl-N-(2,4-dichlorobenzyl)-7-[(3RS,5SR)-3,5-dimethylpiperazin-1-yl]-6-fluoro-8-methoxy-4-oxo-1,4-dihydroquinoline-3-carboxamide

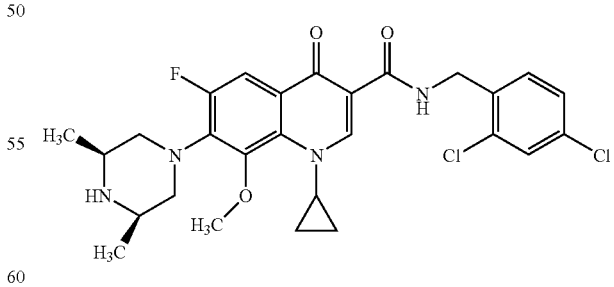

The preparation takes place in analogy to Example 7 from 1-cyclopropyl-7-(cis-3,5-dimethylpiperazin-1-yl)-6-fluoro-8-methoxy-4-oxo-1,4-dihydroquinoline-3-carboxylic acid (for preparation see *Journal of Medicinal Chemistry* (1995) 38:4478-4487).

LC-MS (Method 2): $R_t$=1.77 min, MS (ES+)=547 (M+H)$^+$

Example 13

1-Cyclopropyl-N-(2,4-dichlorobenzyl)-8-difluoromethoxy-7-[(3RS,5SR)-3,5-dimethylpiperazin-1-yl]-6-fluoro-4-oxo-1,4-dihydroquinoline-3-carboxamide

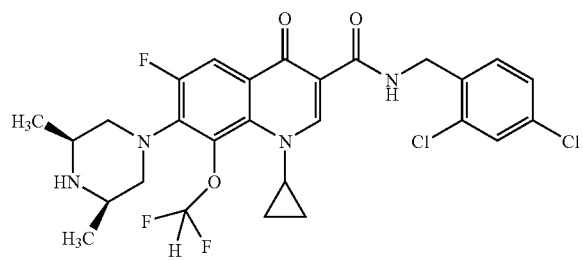

The preparation takes place in analogy to Example 7 from 1-cyclopropyl-7-(cis-3,5-dimethylpiperazin-1-yl)-8-difluoromethoxy-6-fluoro-4-oxo-1,4-dihydroquinoline-3-carboxylic acid (for preparation see EP 352123).

LC-MS (Method 2): $R_t$=2.05 min, MS (ES+)=583 (M+H)$^+$

Example 14

N-(4-Chloro-2-methylbenzyl)-1-cyclopropyl-6-fluoro-7-{4-[2-(2-hydroxyethoxy)ethyl]piperazin-1-yl}-8-methoxy-4-oxo-1,4-dihydroquinoline-3-carboxamide

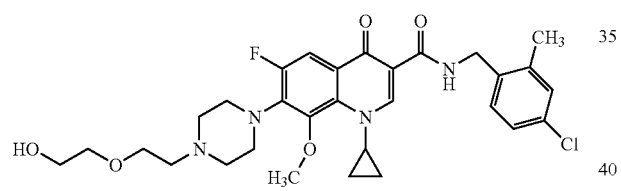

The preparation takes place in analogy to Example 7 from Example 10A.

LC-MS (Method 2): $R_t$=1.70 min, MS (ES+)=587 (M+H)$^+$

Example 15

8-Chloro-N-(4-chloro-2-methylbenzyl)-6-fluoro-1-[(1S,2R)-2-fluorocyclopropyl]-7-[4-(2-morpholin-4-yl-2-oxoethyl)piperazin-1-yl]-4-oxo-1,4-dihydroquinoline-3-carboxamide

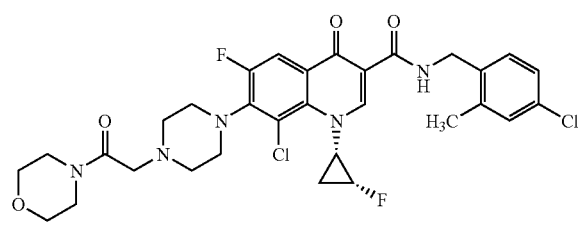

The preparation takes place in analogy to Example 7 from Example 5A.

LC-MS (Method 2): $R_t$=1.66 min, MS (ES+)=648 (M+H)$^+$

Example 16

N-(2,4-Dichlorobenzyl)-7-[(3RS,5SR)-3,5-dimethylpiperazin-1-yl]-6-fluoro-1-[(1R,2S)-2-fluorocyclopropyl]-8-methoxy-4-oxo-1,4-dihydroquinoline-3-carboxamide

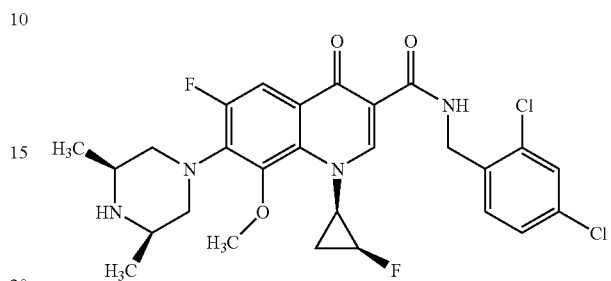

The preparation takes place in analogy to Example 7 from Example 11A.

LC-MS (Method 2): $R_t$=1.66 min, MS (ES+)=565 (M+H)$^+$ $^1$H NMR (300 MHz, CDCl$_3$): δ=1.1 (d, 6H), 1.4-1.7 (m), 2.7-2.9 (m, 2H), 3.0-3.2 (m, 2H), 3.2-3.4 (m, 2H), 3.7 (s, 3H), 3.8-3.9 (m, 1H), 4.6-4.9 (m, about 3H), 7.1-7.2 (dd, 1H), 7.3-7.5 (m, 2H), 7.8-7.9 (d, 1H), 8.8 (s, 1H), 10.3-10.4 (t, 1H).

Example 17

N-(4-Chloro-2-methylbenzyl)-7-[(3RS,5SR)-3 5-dimethylpiperazin-1-yl]-6-fluoro-1-[(1R,2S)-2-fluorocyclopropyl]-8-methoxy-4-oxo-1,4-dihydroquinoline-3-carboxamide

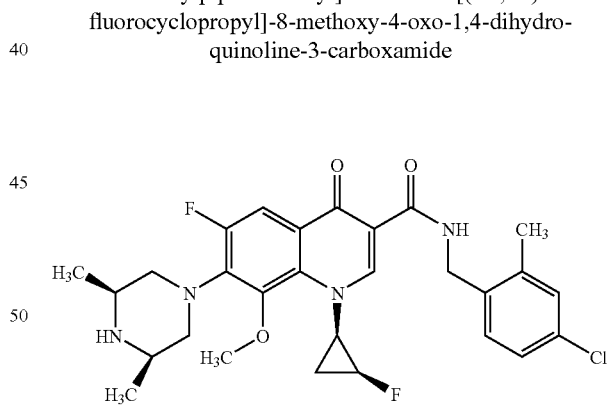

The preparation takes place in analogy to Example 7 from Example 11A.

LC-MS (Method 3): $R_t$=1.89 min, MS (ES+)=545 (M+H)$^+$ $^1$H NMR (300 MHz, CDCl$_3$): δ=1.1 (d, 6H), 1.4-1.7 (m), 2.4 (s, 3H), 2.7-2.9 (m, 2H), 3.0-3.2 (m, 2H), 3.2-3.4 (m, 2H), 3.7 (s, 3H), 3.8-3.9 (m, 1H), 4.5-4.65 (m, 1H), 4.65-5.0 (m, 2H), 7.1-7.2 (m, 2H), 7.3 (m, about 1H), 7.75 (d, 1H), 8.8 (s, 1H), 10.2 (t, 1H).

Example 18

1-Cyclopropyl-N-(2,4-dichlorobenzyl)-8-difluoromethoxy-6-fluoro-7-{4-[2-(2-hydroxyethoxy)ethyl]piperazin-1-yl}-4-oxo-1,4-dihydroquinoline-3-carboxamide

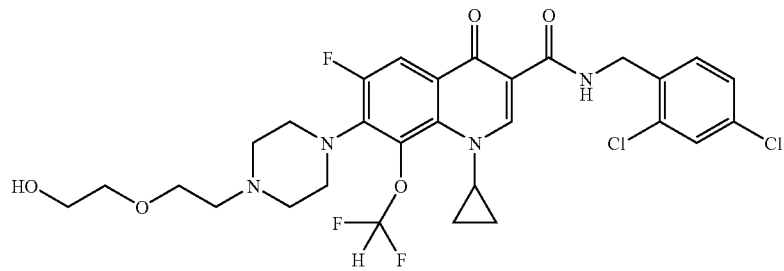

The preparation takes place in analogy to Example 7 from Example 12A.

LC-MS (Method 2): $R_t$=1.66 min, MS (ES+)=643 (M+H)$^+$ $^1$H NMR (400 MHz, CDCl$_3$): δ=0.9 (m, 2H), 1.2 (m, 2H), 2.7 (m, about 6H), 3.4 (m, 4H), 3.6-3.8 (m, 6H), 4.1 (m, 1H), 4.7 (d, 2H), 6.5 (dd, 1H), 7.2 (m, 1H), 7.4 (m, 2H), 8.0 (d, 1H), 8.8 (s, 1H), 10.2 (t, 1H).

Example 19

N-(4-Bromo-2-chlorobenzyl)-1-cyclopropyl-7-[(3RS,5RS-3,5-dimethyl)piperazin-1-yl]-6-fluoro-8-methoxy-4-oxo-1,4-dihydroquinoline-3-carboxamide hydroformate

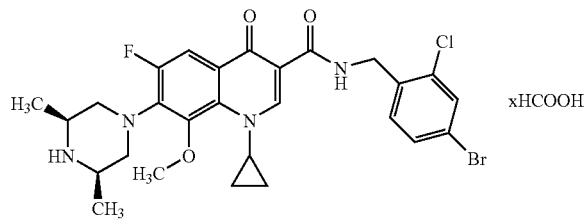

130 mg (0.25 mmol) of PyBOP, 78 mg (0.36 mmol) of 2-bromo-4-chlorobenzylamine (Example 70A) and 127 mg (0.98 mmol) of N,N-diisopropylethylamine are added to 75 mg (0.19 mmol) 1-cyclopropyl-7-(cis-3,5-dimethylpiperazin-1-yl)-6-fluoro-8-methoxy-4-oxo-1,4-dihydroquinoline-3-carboxylic acid (for preparation see: *Journal of Medicinal Chemistry* (1995) 38:4478-4487) in 2 ml dimethylformamide under argon and the mixture is stirred over night at room temperature. The reaction mixture is diluted with 2 ml of water and without further work-up purified by preparative HPLC (Method 5). 92 mg of the title compound are obtained.

LC-MS (Method 1): $R_t$=1.96 min, MS (ES+)=591 (M+H)$^+$, ($^{79}$Br$^{35}$Cl), 593 (M+H)$^+$ ($^{81}$Br$^{35}$Cl).

$^1$H NMR (300 MHz, CDCl$_3$): δ=0.97 (m, 2H), 1.18 (m, 2H), 1.38 (d, 6H), 3.34-3.52 (m, 6H), 3.77 (s, 3H), 3.95 (m, 1H), 4.69 (d, 2H), 4.86 (m, 1H), 7.33 (m, 2H), 7.52 (s, 2H), 7.91 (d, 1H), 8.43 (s, 1H), 8.86 (s, 1H), 10.34 (t, 1H)

From the same acid and in analogy to the preparation instructions of Example 19 Examples 20 to 27 are prepared from the corresponding amines (commercially available or described in Examples 69A to 78A).

| Example-No. | Structure | Analytical data<br>LC-MS (Method)/measured values<br>HPLC (Method)/measured value<br>MS (Method)/measured value<br>NMR-spectrum |
|---|---|---|
| 20 | ![structure] | LC-MS (Method 1): $R_1$ = 1.84 min<br>MS (ES+): m/z = 571 (M + H, $^{79}$Br)$^+$;<br>m/z = 573 (M + H, $^{79}$Br)$^+$;<br>m/z = 573 (M + H, $^{81}$Br)$^+$<br>$^1$H NMR (400 MHz, CDCl$_3$): δ = 0.97(m, 2H), 1.18(m, 2H), 1.34(d, 6H), 2.37(s, 3H), 3.21-3.51(m, 6H), 3.77(s, 3H), 3.95(m, 1H), 4.56 (d, 2H), 7.21(m, 1H), 7.31(m, 2H), 7.88(d, 1H), 8.47(s, 1H), 8.86(s, 1H), 10.16(m, 1H) |

-continued

| Example-No. | Structure | Analytical data<br>LC-MS (Method)/measured values<br>HPLC (Method)/measured value<br>MS (Method)/measured value<br>NMR-spectrum |
|---|---|---|
| 21 | (structure) x HCOOH | LC-MS (Method 3): $R_t$ = 1.92 min<br>MS (ES+): m/z = 591 (M + H, $^{79}$Br)$^+$;<br>m/z = 593 (M + H, $^{81}$Br)$^+$ |
| 22 | (structure) x HCOOH | HPLC (Method 10): $R_t$ = 4.27 min<br>MS (ESI): m/z = 545 (M + H)$^+$ |
| 23 | (structure) x HCl | LC-MS (Method 1): $R_t$ = 1.82 min<br>MS (ES+): m/z = 581 (M + H)$^+$ |
| 24 | (structure) x HCl | LC-MS (Method 3): $R_t$ = 1.93 min<br>MS (ES+): m/z = 561 (M + H)$^+$<br>$^1$H NMR (300 MHz, DMSO-d$_6$): δ = 0.98(m, 2H), 1.12(m, 2H), 1.28(d, 6H), 2.41(s, 3H) 3.15-3.56(m 6H), 3.79(s, 3H), 4.11(m, 1H), 4.59(d, 2H), 7.42(d, 1H), 7.52(d, 1H), 7.58 (s, 1H), 7.75(d, 1H), 8.72(s, 1H), 10.18(t, 1H) |
| 25 | (structure) x HCOOH | HPLC (Method 9): $R_t$ = 4.60 min<br>MS (ESI): m/z = 597 (M + H)$^+$<br>$^1$H NMR (400 MHz, CDCl$_3$): δ = 0.97(m, 2H), 1.18(m, 2H), 1.32(d, 6H), 3.19-3.41(m, 4H), 3.45(d, 2H), 3.77(s, 3H), 3.95(m, 1H), 4.71 (d, 2H), 7.09(d, 1H), 7.49(d, 1H), 7.91(d, 1H), 8.40(s, 1H), 8.36(s, 1H), 10.38(t, 1H) |

-continued

| Example-No. | Structure | Analytical data LC-MS (Method)/measured values HPLC (Method)/measured value MS (Method)/measured value NMR-spectrum |
|---|---|---|
| 26 | (structure) | LC-MS (Method 3): $R_t$ = 1.72 min<br>MS (ES+): m/z = 581 (M + H)$^+$ |
| 27 | (structure) | LC-MS (Method 3): $R_t$ = 1.91 min<br>MS (ES+): m/z = 561 (M + H)$^+$ |

Example 28

N-(2,4-Dichlorobenzyl)-7-[(3RS,5RS-3,5-dimethyl)piperazin-1-yl]-6-fluoro-1-(2-fluoroethyl)-8-methoxy-4-oxo-1,4-dihydroquinoline-3-carboxamide hydroformate

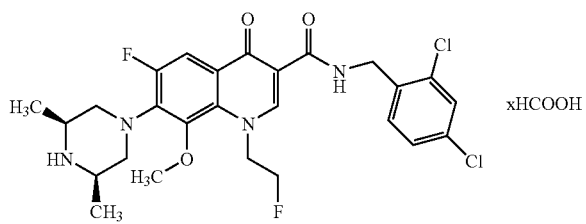

Preparation takes place in analogy to Example 19 from 7-(cis-3,5-dimethylpiperazin-1-yl)-6-fluoro-1-(2-fluoroethyl)-8-methoxy-4-oxo-1,4-dihydroquinoline-3-carboxylic acid (for preparation see: EP 0241206) and 2,4-dichlorobenzylamine.

HPLC (Method 9): $R_t$=4.46 min, MS (ESI)=553 (M+H)$^+$.

$^1$H NMR (400 MHz, DMSO-d$_6$): δ=1.15 (d, 6H), 2.88-3.07 (m, 2H), 3.11-3.56 (m, 4H under the water signal of the DMSO), 3.78 (s, 3H), 4.59 (d, 2H), 4.76 (dd, 2H), 4.95 (d, 2H), 7.35-7.50 (m, 2H), 7.64 (s, 1H), 7.83 (d, 1H), 8.16 (s, 1H), 8.72 (s, 1H), 10.27 (t, 1H).

In analogy to the preparation instructions for Example 19 the Examples 29 to 51 are prepared from various carboxylic acids and benzylamines.

| Example No. | Structure | Starting material Example No. | Analytical data LC-MS (Method)/measured values HPLC (Method)/measured value MS (Method)/measured value NMR-spectrum |
|---|---|---|---|
| 29 | (structure) | See example-No. 28 | HPLC (Method 10): $R_t$ = 4.33 min<br>MS (ESI): m/z = 533 (M + H)$^+$ |

-continued

| Example No. | Structure | Starting material Example No. | Analytical data LC-MS (Method)/measured values HPLC (Method)/measured value MS (Method)/measured value NMR-spectrum |
|---|---|---|---|
| 30 | 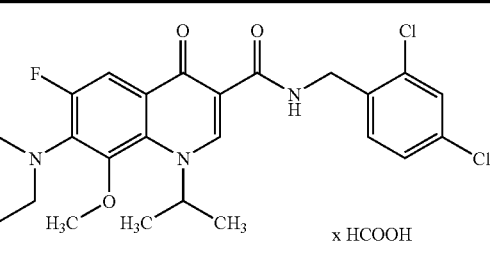 | 59A | HPLC (Method 9): $R_t$ = 4.42 min<br>MS (ESI): m/z = 565 (M + H)$^+$<br>$^1$H NMR (300 MHz, CDCl$_3$): δ = 1.52(d, 6H), 2.98(m, 2H), 3.08(m, 4H), 3.62(m, 4H), 3.79(s, 3H), 3.91(m, 2H), 4.70(d, 2H), 5.76(m, 1H), 7.21(dd, 1H), 7.38(s, 1H), 7.41(d, 1H), 7.97(d, 1H), 8.27(s, 1H), 8.86(s, 1H), 10.43(t, 1H) |
| 31 | 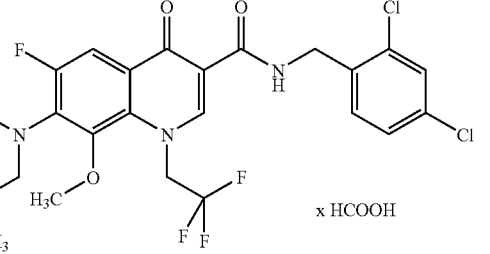 | 50A | HPLC (Method 9): $R_t$ = 4.47 min<br>MS (ESI): m/z = 605 (M + H)$^+$<br>$^1$H NMR (300 MHz, CDCl$_3$): δ = 1.33(d, 6H), 3.21-3.45(m, 6H), 3.82(s, 3H), 4.70(d, 2H), 5.25(q, 2H), 7.21(dd, 1H), 7.38(d, 1H), 7.40(d, 1H), 7.95(d, 1H), 8.42(s, 1H), 8.57(s, 1H), 10.22(t, 1H) |
| 32 | 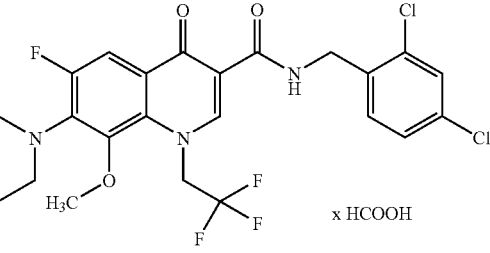 | 60A | HPLC (Method 9): $R_t$ = 4.46 min<br>MS (ESI): m/z = 533 (M + H)$^+$ |
| 33 | 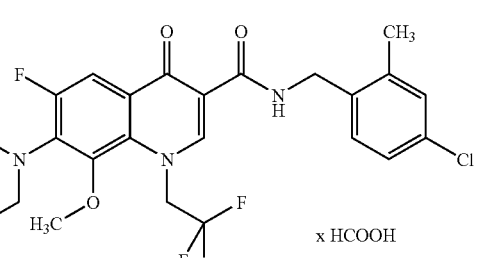 | 50A | HPLC (Method 10): $R_t$ = 4.52 min<br>MS (ESI): m/z = 569 (M + H)$^+$ |
| 34 enantiomerically pure | 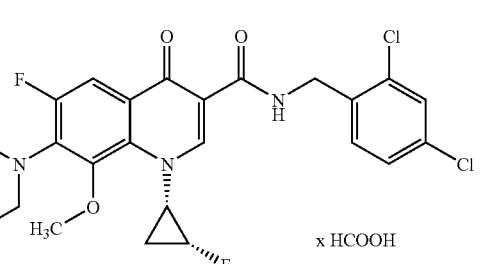 | 58A | LC-MS (Method 1): $R_t$ = 1.98 min<br>MS (ES+): m/z = 565 (M + H)$^+$ |

-continued

| Example No. | Structure | Starting material Example No. | Analytical data<br>LC-MS (Method)/measured values<br>HPLC (Method)/measured value<br>MS (Method)/measured value<br>NMR-spectrum |
|---|---|---|---|
| 35 | 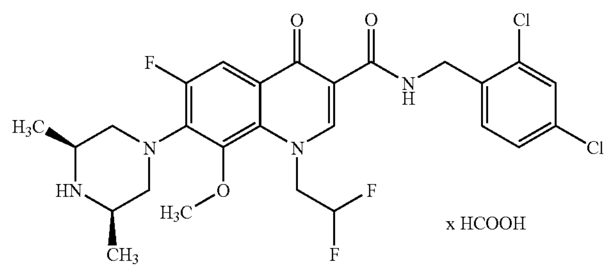 | 57A | HPLC (Method 10): $R_t$ = 4.57 min<br>MS (ESI): m/z = 571 (M + H)$^+$<br>$^1$H NMR (300 MHz, CDCl$_3$): δ =<br>1.35(d, 6H), 3.31-3.48(m, 6H), 3.85<br>(s, 3H), 4.69(d, 2H), 4.83(td, 2H),<br>6.04(tt, 1H), 7.21(dd, 1H), 7.37-<br>7.42(m, 2H), 7.98(d, 1H,<br>8.41(s, 1H), 8.59(s, 1H), 10.26(t, 1H) |
| 36 racemic | 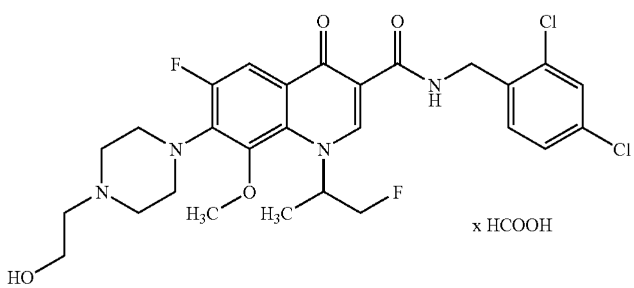 | 61A | LC-MS (Method 1): $R_t$ = 1.75 min<br>MS (ES+): m/z = 583 (M + H)$^+$ |
| 37 racemic | 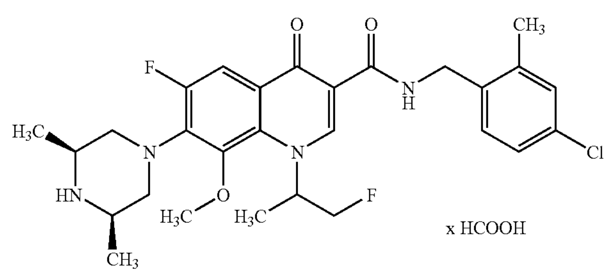 | 51A | LC-MS (Method 1): $R_t$ = 1.81 min<br>MS (ES+): m/z = 547 (M + H)$^+$ |
| 38 | 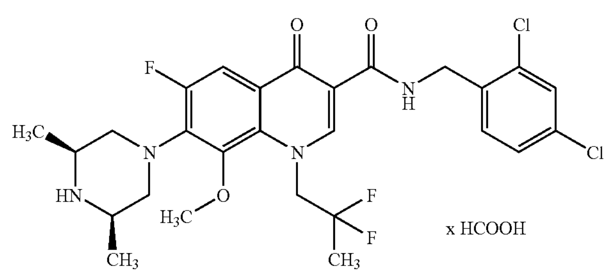 | 56A | LC-MS (Method 2): $R_t$ = 1.73 min<br>MS (ES+): m/z = 565 (M + H)+<br>$^1$H NMR (300 MHz, DMSO-$_6$): δ =<br>1.24(d, 6H), 1.56(t, 3H), 3.14(m,<br>2H), 3.43(m, 2H), 3.49(m, 2H),<br>3.81(s, 3H), 4.59(d, 2H), 5.31(t,<br>2H), 7.37-7.47(m, 2H), 7.64(s, 2H),<br>7.82(d, 1H), 8.72(s, 1H), 10.16(t,<br>1H) |
| 39 | 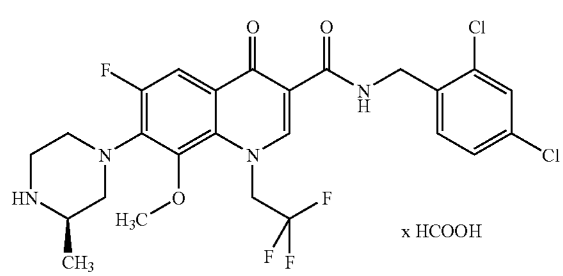 | 62A | LC-MS (Method 3): $R_t$ = 1.92 min<br>MS (ES+): m/z = 575 (M + H)$^+$ |

|Example No.|Structure|Starting material Example No.|Analytical data LC-MS (Method)/measured values HPLC (Method)/measured value MS (Method)/measured value NMR-spectrum|
|---|---|---|---|
| 40 | (structure with F, methoxy, cyclobutyl, dimethylpiperazine, N-(2,4-dichlorobenzyl)carboxamide) × CF₃COOH | 54A | LC-MS (Method 1): $R_t$ = 2.16 min<br>MS (ES+): m/z = 561 (M + H)⁺<br>purification (Method 8) |
| 41 | (structure with F, CN, cyclobutyl, dimethylpiperazine, N-(2,4-dichlorobenzyl)carboxamide) × HCl | 63A | LC-MS (Method 1): $R_t$ = 1.97 min<br>MS (ES+): m/z = 542 (M + H)⁺<br>¹H NMR (400 MHz, DMSO-$d_6$): δ = 1.22(m, 2H), 1.26-1.38(m, 8H): in there 1.30(d, 6H)), 3.41-3.57(m, 4H), 3.79(m, 2H), 4.15(m, 1H), 4.59(d, 2H), 7.36-7.46(m, 2H), 7.64 (s, 1H), 8.19(d, 1H), 8.70(s, 1H), 10.09(t, 1H) |
| 42 | (structure with F, methoxy, 2,2-difluoroethyl, dimethylpiperazine, N-(4-chloro-2-methylbenzyl)carboxamide) × HCOOH | 57A | HPLC (Method 10): $R_t$ = 4.48 min<br>MS (ESI): m/z = 551 (M + H)⁺ |
| 43 | (structure with F, methoxy, fluorocyclopropyl, dimethylpiperazine, N-(4-chloro-2-methylbenzyl)carboxamide) | 58A | LC-MS (Method 3): $R_t$ = 1.97 min<br>MS (ES+): m/z = 545 (M + H)⁺<br>¹H NMR (400 MHz, DMSO-$d_6$): δ = 1.06(d, 6H), 1.43-1.68(m, 2H), 2.32(s, 3H), 2.72-2.91(m, 2H), 3.06(m, 2H), 3.25(m, 2H), 3.77(s, 3H), 4.08(m, 1H), 4.51 (d, 2H), 4.93/5.10(2m, 1H), 7.19-7.32(m, 3H), 7.71(d, 1H), 8.68(s, 1H), 10.08(t, 1H) |
| 44 | (structure with F, methoxy, 2,2-difluoropropyl, dimethylpiperazine, N-(4-chloro-2-methylbenzyl)carboxamide) × HCOOH | 56A | LC-MS (Method 2): $R_t$ = 1.77 min<br>MS (ES+): m/z = 585 (M + H)⁺ |

-continued

| Example No. | Structure | Starting material Example No. | Analytical data LC-MS (Method)/measured values HPLC (Method)/measured value MS (Method)/measured value NMR-spectrum |
|---|---|---|---|
| 45 (S)-enantiomer | 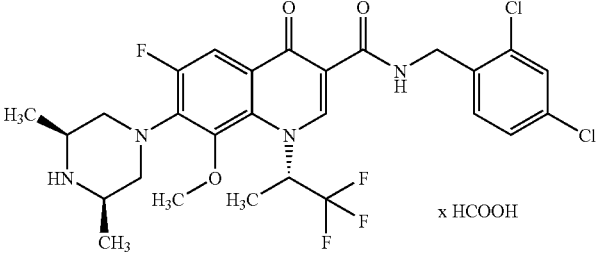 x HCOOH | 52A | HPLC (Method 9): $R_t$ = 4.75 min MS (ESI): m/z = 603 (M + H)⁺ |
| 46 (R)-enantiomer | 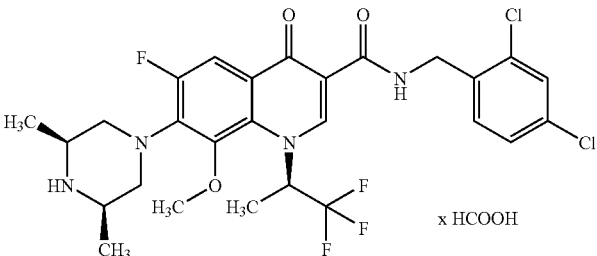 x HCOOH | 53A | LC-MS (Method 2): $R_t$ = 1.78 min MS (ES+): m/z = 603 (M + H)⁺ |
| 47 HCl salt of Example 31 | 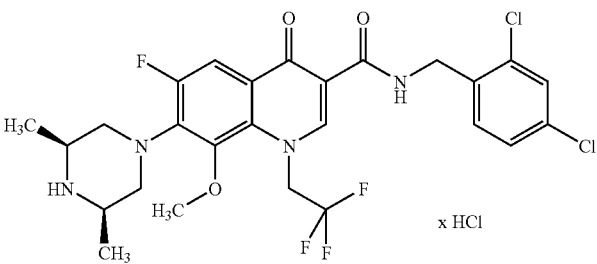 x HCl | 50A | HPLC (Method 9): $R_t$ = 4.58 min MS (ESI): m/z = 589 (M + H)⁺ |
| 48 | 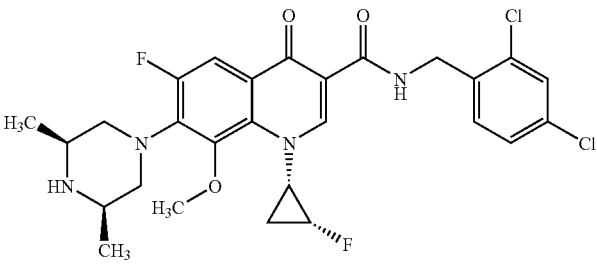 | 58A | LC-MS (Method 3): $R_t$ = 1.86 min MS (ES+): m/z = 565 (M + H)⁺ |
| 49 | 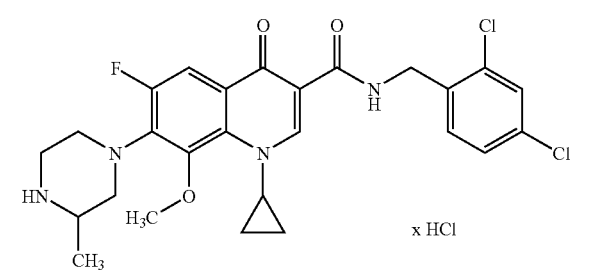 x HCl | Gatifloxacin | LC-MS (Method 2): $R_t$ = 2.05 min MS (ES+): m/z = 542 (M + H)⁺ |

-continued

| Example No. | Structure | Starting material Example No. | Analytical data LC-MS (Method)/measured values HPLC (Method)/measured value MS (Method)/measured value NMR-spectrum |
|---|---|---|---|
| 50 | 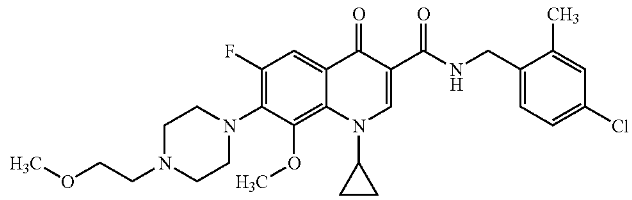 | 13A | LC-MS (Method 2): $R_t$ = 1.94 min<br>MS (ES+): m/z = 557 (M + H)$^+$ |
| 51 | 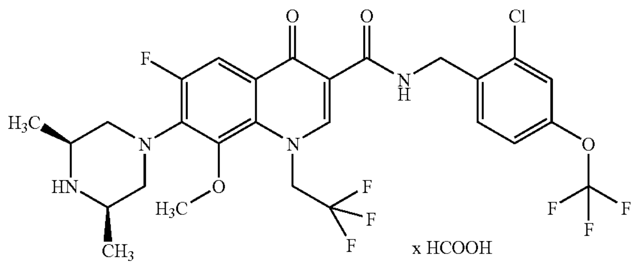 | 50A | HPLC (Method 9): $R_t$ = 4.71 min<br>MS (ESI): m/z = 639 (M + H)$^+$ |

Example 52

7-[(3RS,5SR)-3,5-Dimethylpiperazin-1-yl]-6-fluoro-8-methoxy-N-[2-methyl-4-(trifluoromethoxy)benzyl]-4-oxo-1-(2,2,2-trifluoroethyl)-1,4-dihydroquinoline-3-carboxamide

Example 53

{(2RS,6SR)-4-[3-{[(2,4-Dichlorobenzyl)amino]carbonyl}-6-fluoro-8-methoxy-4-oxo-1-(2,2,2-trifluoroethyl)-1,4-dihydroquinolin-7-yl]-2,6-dimethylpiperazin-1-yl}acetamide

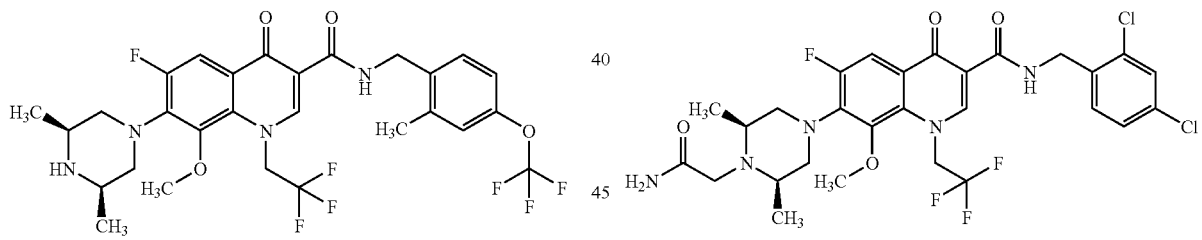

212 mg (0.49 mmol) of 7-[(3RS,5SR)-3,5-dimethylpiperazin-1-yl]-6-fluoro-8-methoxy-4-oxo-1-(2,2,2-trifluoroethyl)-1,4-dihydroquinoline-3-carboxylic acid (salt free compound of Example 50A) and 366 mg (0.98 mmol) of 2-methyl-4-trifluoromethoxybenzylamine (Example 69A) are dissolved together with 357 mg (0.69 mmol) of PyBOP and 30 mg (0.25 mmol) of 4-dimethylaminopyridine in 4 ml of DMF and stirred for 12 h at room temperature. The reaction mixture is then purified by preparative HPLC (Method 7). A solid is obtained. Yield: 170 mg (56% of theory).

LC-MS (Method 1): $R_t$=2.00 min, MS (ES+): m/z=619 (M+H)$^+$ $^1$H NMR (400 MHz, DMSO-$d_6$): δ=10.0 (t, 1H), 8.85 (bs, 1H), 7.76 (d, 1H), 7.37 (d, 1H), 7.22 (m, 1H), 7.15-7.19 (m, 1H), 5.71 (q, 2H), 4.55 (d, 2H), 3.78 (s, 3H), 3.17-3.24 (m, 2H), 2.92-3.06 (m, 2H), 2.70-2.83 (m, 2H), 2.37 (s, 3H), 1.00 (d, 6H).

243 mg (0.41 mmol) of N-(2,4-dichlorobenzyl)-7-[(3RS, 5SR)-3,5-dimethylpiperazin-1-yl]-6-fluoro-8-methoxy-4-oxo-1-(2,2,2-trifluoroethyl)-1,4-dihydroquinoline-3-carboxamide (released from the hydrochloride of the compound of Example 47), 46.3 mg (0.49 mmol) of chloroacetamide, 75 mg (0.45 mmol) of potassium iodide and 143 mg (1.03 mmol) of potassium carbonate are stirred over night under reflux in 4 ml of acetonitrile. After cooling the mixture is filtered and separated by preparative HPLC (Method 5). For fine purification the obtained product is stirred in hot acetonitrile, cooled and filtered. After drying under high vacuum 46 mg (16% of theory) of the title compound are obtained.

LC-MS (Method 3): $R_t$=2.05 min, MS (ES+): m/z=646 (M+H)$^+$.

$^1$H NMR (400 MHz, CDCl$_3$): δ=1.12 (d, 6H), 2.82 (m, 2H), 3.04 (m, 2H), 3.21 (m, 2H), 3.33 (m, 2H), 3.84 (s, 3H), 4.69 (d, 2H), 5.23 (m, 2H), 5.45 (s, 1H), 7.21 (m, 1H), 7.34-7.44 (m, 2H), 7.93 (d, 1H), 8.54 (s, 1H), 10.19 (m, 1H).

In analogy to the preparation of Example 53 the following Examples 54 to 75 are prepared from the corresponding piperazines with electrophiles. As electrophiles chloroacetamide, N-methylchloroacetamide, N,N-dimethylchloroacetamide, N-methylsulfonylchloroacetamide (for preparation see: DE 19937024), 2-chloropropionamide, various alkylchloromethylketones or 3-bromopropionamide are used.

| Example No. | Structure | Starting material Example No. | Analytical date LC-MS (Method)/measured values HPLC (Method)/measured value MS (Method)/measured value NMR-spectrum |
|---|---|---|---|
| 54 | 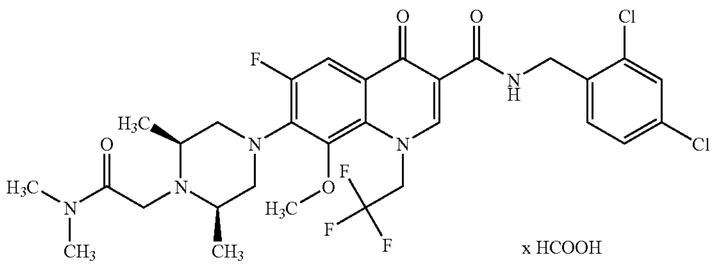 | 47 | HPLC (Method 9): $R_t$ = 4.77 min<br>MS (ESI): m/z = 674 (M + H)+ |
| 55 | 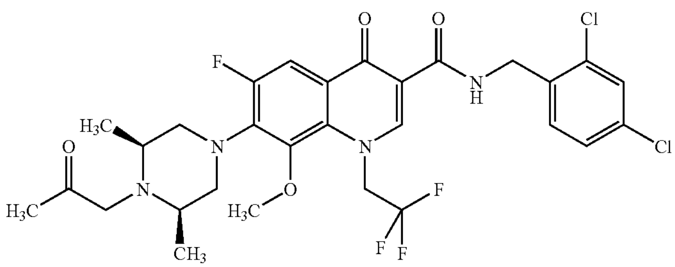 | 47 | HPLC (Method 9): $R_t$ = 4.74 min<br>MS (ESI): m/z = 645 (M + H)+ |
| 56 | 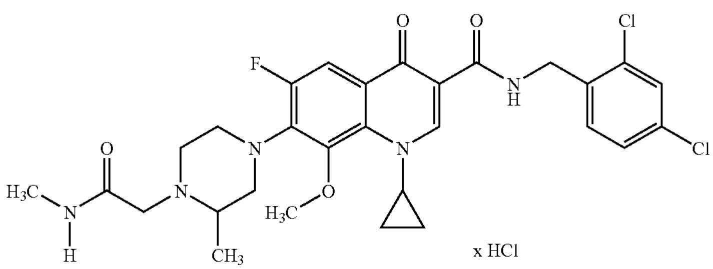 | 49 | LC-MS (Method 3): $R_t$ = 2.05 min<br>MS (ES+): m/z = 604 (M + H)+ |
| 57 | 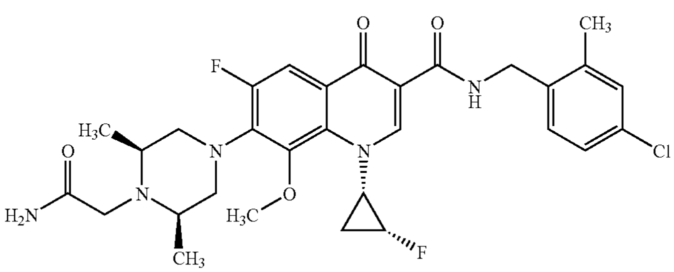 | 43 | LC-MS (Method 1): $R_t$ = 2.02 min<br>MS (ES+): m/z = 603 (M + H)+ |
| 58 | 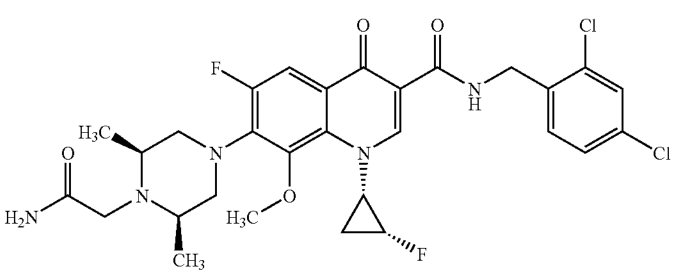 | 48 | LC-MS (Method 2): $R_t$ = 1.91 min<br>MS (ES+): m/z = 622 (M + H)+ |

-continued

| Example No. | Structure | Starting material Example No. | Analytical date LC-MS (Method)/measured values HPLC (Method)/measured value MS (Method)/measured value NMR-spectrum |
|---|---|---|---|
| 59 | 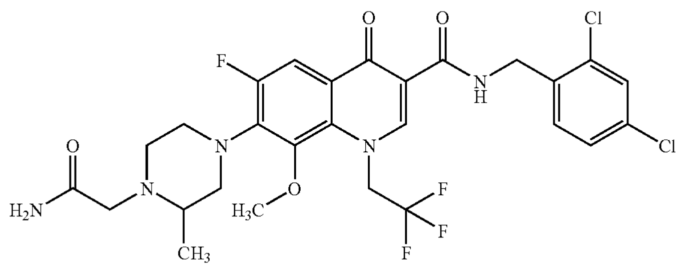 | 39 | LC-MS (Method 2): $R_t$ = 1.83 min<br>MS (ES+): m/z = 632 (M + H)$^+$ |
| 60 | 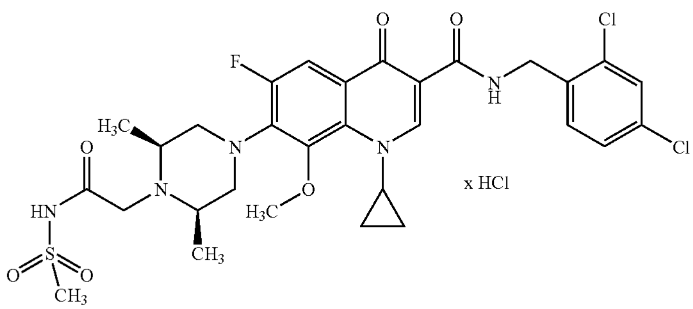 | 12 | LC-MS (Method 3): $R_t$ = 2.22 min<br>MS (ES+): m/z = 542 (M + H)$^+$<br>$^1$H NMR (400 MHz, DMSO-d$_6$): δ = 0.97(m, 2H), 1.11(m, 2H), 1.28 (d, 6H), 3.12-3.33(m, 5H: in there 1.29(s, 3H)), 3.75(m, 2H), 3.79 (s, 3H), 4.09(m, 1H), 4.15(m, 2H), 4.58(d, 2H), 7.33-7.48(m, 2H), 7.63(s, 2H), 7.78(d, 1H), 8.68(s, 1H), 10.22(t, 1H) |
| 61 | 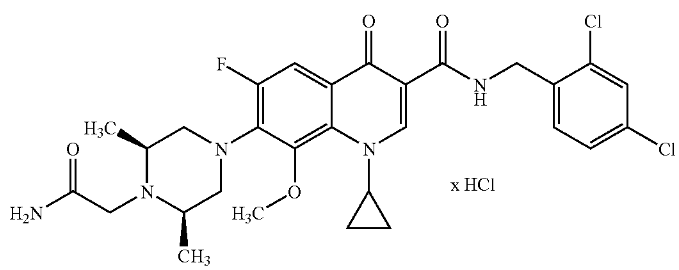 | 12 | LC-MS (Method 2): $R_t$ = 1.86 min<br>MS (ES+): m/z = 604 (M + H)$^+$ |
| 62 | 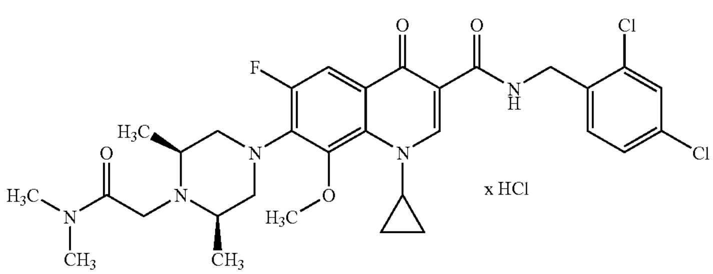 | 12 | LC-MS (Method 3): $R_t$ = 1.91 min<br>MS (ES+): m/z = 632 (M + H)$^+$ |
| 63 | 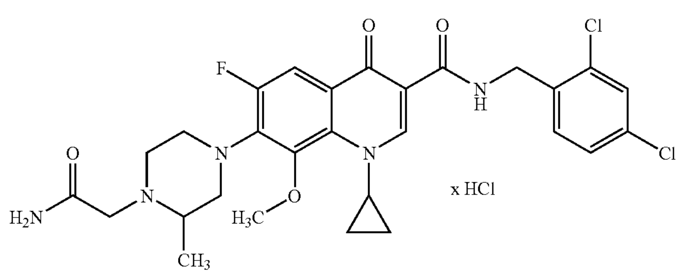 | 49 | LC-MS (Method 1): $R_t$ = 1.97 min<br>MS (ES+): m/z = 542 (M + H)$^+$ |

-continued

| Example No. | Structure | Starting material Example No. | Analytical date LC-MS (Method)/measured values HPLC (Method)/measured value MS (Method)/measured value NMR-spectrum |
|---|---|---|---|
| 64 | 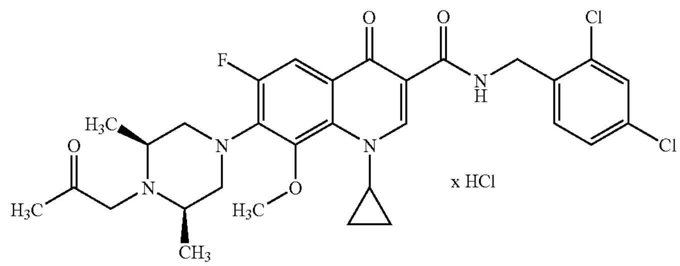 | 12 | LC-MS (Method 2): $R_t$ = 1.67 min<br>MS (ES+): m/z = 590 (M + H)$^+$<br>$^1$H NMR (300 MHz, CDCl$_3$): δ = 0.96(m, 2H), 1.17(m, 2H), 1.49 (d, 6H), 2.32(s, 3H), 3.42-3.58(m, 2H), 3.81(s, 3H), 3.95(m, 1H), 4.0-4.15(m, 2H), 4.23(m, 2H), 4.31(m, 2H), 4.68(d, 2H), 7.21 (dd, 1H), 7.39(m, 2H), 7.94(d, 1H), 8.85(s, 1H), 10.31(t, 1H), 13.08(bs, 1H) |
| 65 | 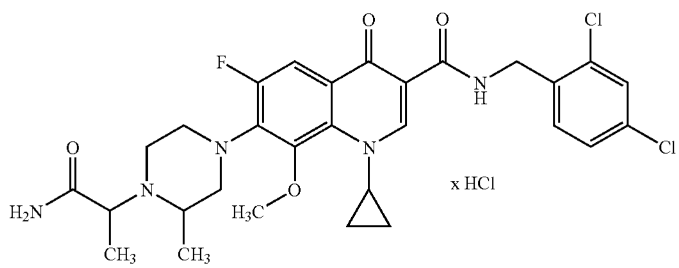 | 49 | LC-MS (Method 2): $R_t$ = 1.89 min<br>MS (ES+): m/z = 604 (M + H)$^+$ |
| 66 | 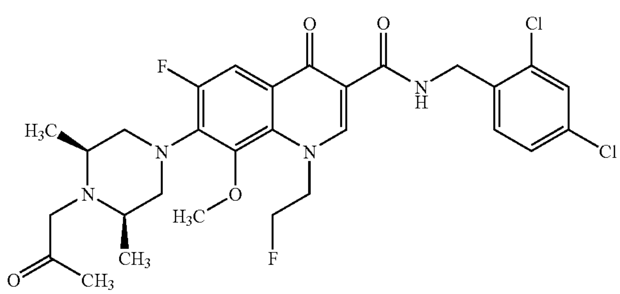 | 28 | HPLC (Method 9): $R_t$ = 4.65 min<br>MS (ES+): m/z = 610 (M + H)$^+$ |
| 67 | 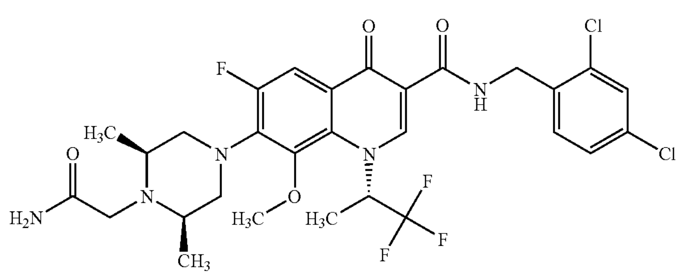 | 45 | HPLC (Method 9): $R_t$ = 4.38 min<br>MS (ES+): m/z = 660 (M + H)$^+$ |
| 68 | 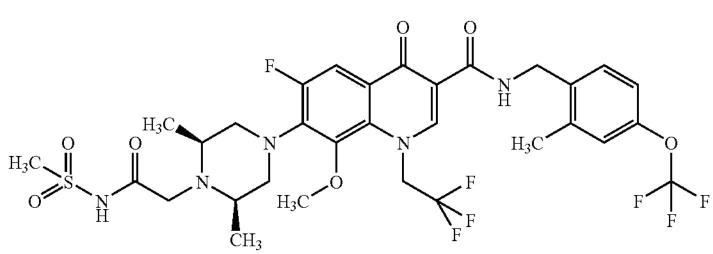 | 52 | LC-MS (Method 1): $R_t$ = 2.34 min<br>MS (ES+): m/z = 754 (M + H)$^+$ |

-continued

| Example No. | Structure | Starting material Example No. | Analytical date LC-MS (Method)/measured values HPLC (Method)/measured value MS (Method)/measured value NMR-spectrum |
|---|---|---|---|
| 69 | 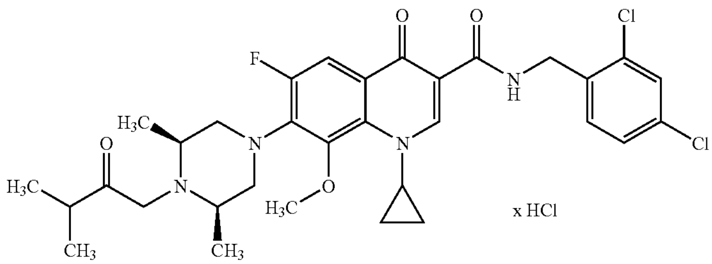 | 12 | LC-MS (Method 3): $R_t$ = 2.07 min<br>MS (ES+): m/z = 631 (M + H)$^+$ |
| 70 | 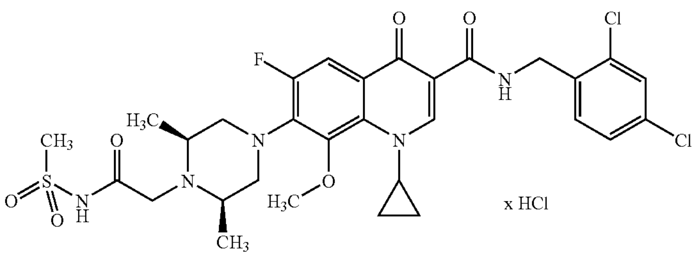 | 47 | HPLC (Method 9): $R_t$ = 4.66 min<br>MS (ES+): m/z = 724 (M + H)$^+$ |
| 71 | 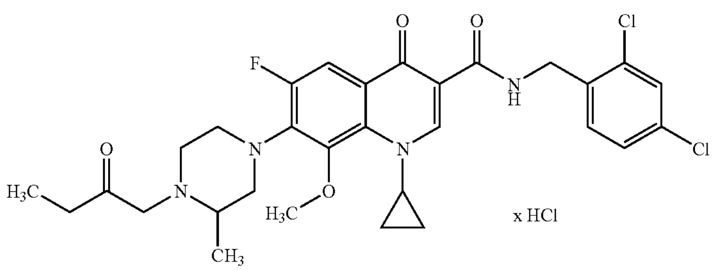 | 49 | LC-MS (Method 3): $R_t$ = 1.95 min<br>MS (ES+): m/z = 603 (M + H)$^+$ |
| 72 | 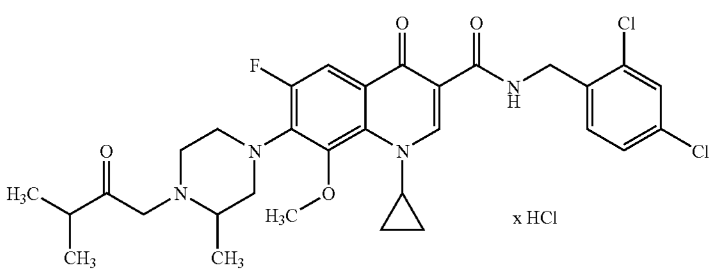 | 49 | LC-MS (Method 3): $R_t$ = 2.04 min<br>MS (ES+): m/z = 617 (M + H)$^+$ |
| 73 | 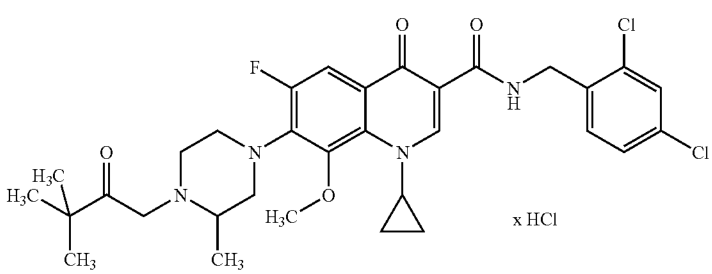 | 49 | LC-MS (Method 3): $R_t$ = 2.07 min<br>MS (ES+): m/z = 631 (M + H)$^+$ |

| Example No. | Structure | Starting material Example No. | Analytical date LC-MS (Method)/measured values HPLC (Method)/measured value MS (Method)/measured value NMR-spectrum |
|---|---|---|---|
| 74 | 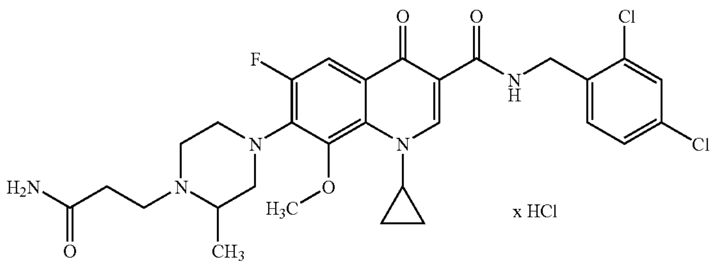 | 49 | LC-MS (Method 3): $R_t$ = 1.85 min<br>MS (ES+): m/z = 604 (M + H)$^+$ |
| 75 | 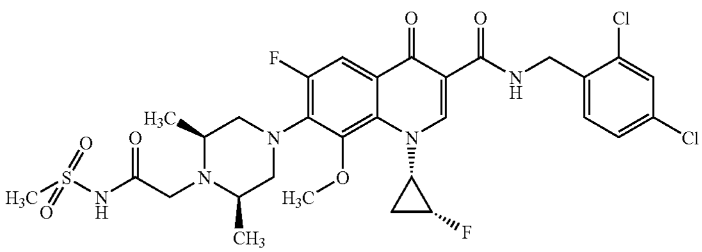 | 48 | LC-MS (Method 2): $R_t$ = 2.01 min<br>MS (ES+): m/z = 700 (M + H)$^+$ |

Example 76

N-Ethyl-{4-[1-cyclopropyl-3-{[(2,4-dichlorobenzyl)amino]carbonyl}-6-fluoro-8-methoxy-4-oxo-1,4-dihydroquinolin-7-yl]-(2RS,6SR)-2,6-dimethylpiperazin-1-yl}acetamide hydrochloride

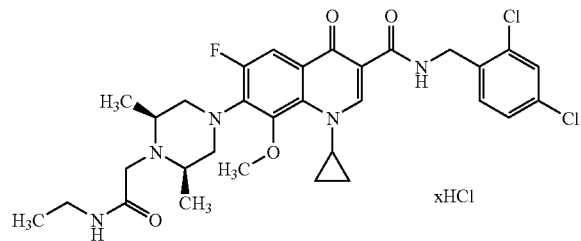

50 mg of the compound of Example 84A are provided in 2 ml of DMF. An ethylamine solution (2M in THF) with 103 mg of PyBOP and 35 µl of Hünig's base are added and the mixture is left stirring for 24 h at room temperature. The complete reaction mixture is separated by preparative HPLC (Method 6). 36 mg (69% of theory) of the title compound are obtained.

LC-MS (Method 3): $R_t$=2.17 min, MS (ES+): m/z=632 (M+H)$^+$ $^1$H NMR (400 MHz, DMSO-d$_6$): δ=0.97 (m, 2H), 1.05-1.14 (m, 5H), 1.33 (d, 6H), 3.20 (m, 2H), 3.49 (d, 2H), 3.60 (t, 2H), 3.74-3.80 (m, 5H, underneath there 3.78 (s, 3H)), 4.02-4.10 (m, 3H), 4.58 (d, 2H), 7.37-7.43 (m, 2H), 7.52 (s, 1H), 7.77 (d, 1H), 8.69 (s, 1H), 10.22 (t, 1H).

In analogy to Example 76 the following compounds are obtained with the corresponding amines:

| Example No. | Structure | Analytical data LC-MS (Method)/measured value HPLC (Method)/measured value MS (Method)/measured value |
|---|---|---|
| 77 | 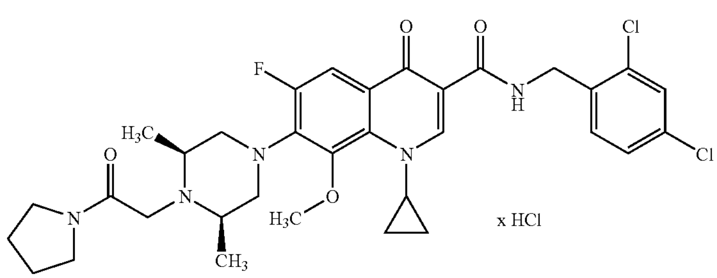 | LC-MS (Method 3): $R_t$ = 2.05 min<br>MS (ES+): m/z = 658 (M + H)$^+$ |

-continued

| Example No. | Structure | Analytical data<br>LC-MS (Method)/measured value<br>HPLC (Method)/measured value<br>MS (Method)/measured value |
|---|---|---|
| 78 | 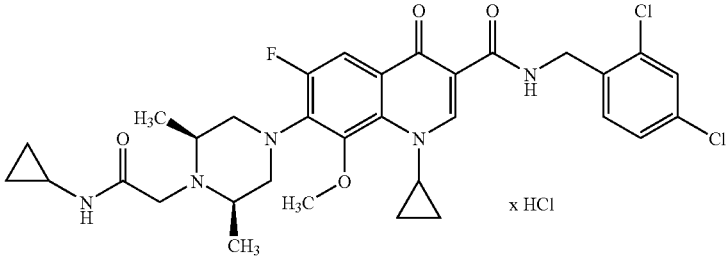 x HCl | LC-MS (Method 3): $R_t$ = 2.10 min<br>MS (ES+): m/z = 644 (M + H)$^+$ |

Example 79

1-Cyclopropyl-N-(2,4-dichlorobenzyl)-6-fluoro-7-[(3RS,5SR)-4-glycyl-3,5-dimethylpiperazin-1-yl]-8-methoxy-4-oxo-1,4-dihydroquinoline-3-carboxamide hydrochloride

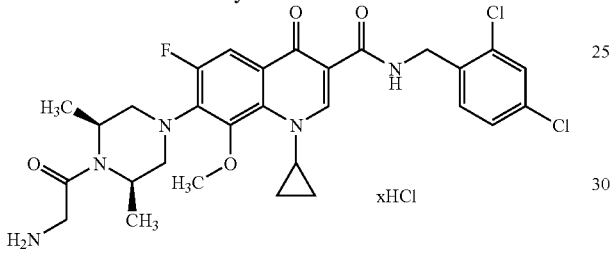

46.0 mg (0.07 mmol) of the compound of Example 82A are provided in 2 ml of tetrahydrofuran, the solution is cooled to 0° C., 21.1 mg (0.08 mmol) of triphenylphosphine, dissolved in 1 ml of tetrahydrofuran are added dropwise, the reaction mixture is warmed to room temperature and stirred over night at this temperature. For the work-up the solvent is removed completely on a rotary evaporator, the residue is prepurified by preparative RP-HPLC (Method 6) and after fine purification by column chromatography on silica gel 60 (eluent: dichloromethane:ethanol 90:10) and concentrating the fractions with the addition of hydrochloric acid 24 mg of the target compound are obtained.

LC-MS (Method 1): $R_t$=1.86 min, MS (ES+): m/z=604 (M+H)$^+$ $^1$H NMR (400 MHz, DMSO-d$_6$): δ=0.95 (m, 2H), 1.09 (m, 2H), 1.38 (d, 3H), 1.46 (d, 3H), 3.39 (m, 2H), 3.57 (s, 2H), 3.70 (s, 3H), 3.75 (m, 1H), 4.03 (m, 1H), 4.10 (m, 2H), 4.55 (m, 1H), 4.59 (d, 2H), 7.37-7.47 (m, 2H), 7.65 (d, 1H), 7.78 (d, 1H), 8.05 (m, 2H), 8.70 (s, 1H), 10.25 (t, 1H).

Example 80

N-(2,4-Dichlorobenzyl)-6-fluoro-7-[(3RS,5 SR)-4-glycyl-3,5-dimethylpiperazin-1-yl]-8-methoxy-1-(2,2,2-trifluoroethyl)-4-oxo-1,4-dihydroquinoline-3-carboxamide hydrochloride

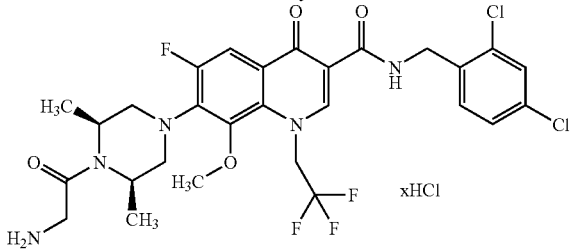

The title compound is prepared in analogy to Example 79 from the compound of Example 83A.

LC-MS (Method 3): $R_t$=2.03 min. MS (ES+): m/z=646 (M+H)$^+$.

Example 81

7-[(3RS,5SR)-4-(Azetidin-1-ylacetyl)-3 5-dimethylpiperazin-1-yl]-1-cyclopropyl-N-(2,4-dichlorobenzyl)-6-fluoro-8-methoxy-4-oxo-1,4-dihydroguinoline-3-carboxamide

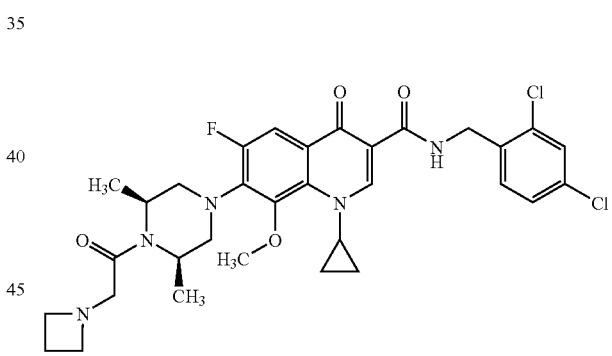

50 mg (0.08 mmol) of the compound of Example 80A and 22.9 mg (0.40 mmol) of azetidine are stirred in 3 ml of ethanol in a closed reaction vessel over night at 90° C. For the work-up the solvent is removed completely on a rotary evaporator and the residue is purified by preparative RP-HPLC (Method 6). The target compound is obtained with 24 mg.

LC-MS (Method 1): $R_t$=1.97 min. MS (ES+): m/z=644 (M+H)$^+$ $^1$H NMR (400 MHz, DMSO-d$_6$): δ=0.95 (m, 2H), 1.08 (m, 2H), 1.37 (d, 3H), 1.48 (d, 3H), 2.23-2.58 (m, 2H), 3.22-3.49 (m, 4H), 3.70 (s, 3H), 3.87 (m, 1H), 3.95-4.38 (m, 6H), 4.45-4.67 (m, 4H: in there 4.58 (d, 2H)), 7.35-7.47 (m, 2H), 7.64 (d, 1H), 7.78 (d, 1H), 8.69 (s, 1H), 10.25 (t, 1H).

In analogy to Example 81 the following Examples 82 to 84 are prepared:

| Example No. | Structure | Analytical data<br>LC-MS (Method)/measured value<br>MS (Method)/measured value |
|---|---|---|
| 82 | 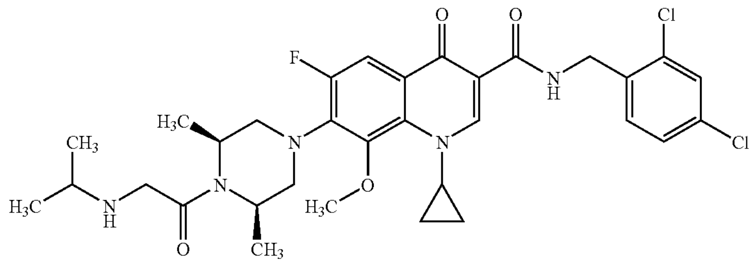 | LC-MS (Method 1): $R_t$ = 1.95 min<br>MS (ES+): m/z = 646 (M + H)$^+$ |
| 83 | 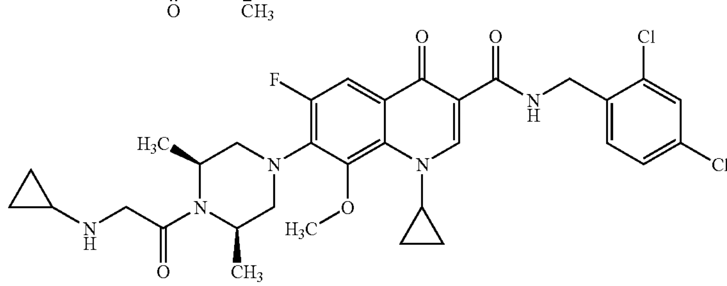 | LC-MS (Method 1): $R_t$ = 1.95 min<br>MS (ES+): m/z = 644 (M + H)$^+$ |
| 84 | 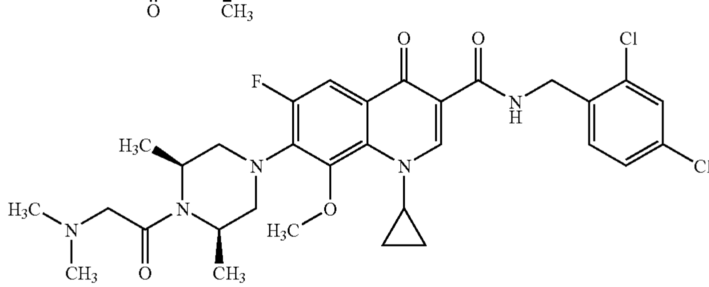 | LC-MS (Method 1): $R_t$ = 1.91 min<br>MS (ES+): m/z = 632 (M + H)$^+$ |

Example 85
8-Chloro-1-cyclopropyl-N-(2,4-dichlorobenzyl)-7-[4-acetylpiperazin-1-yl]-6-fluoro-4-oxo-1,4-dihydroquinoline-3-carboxamide

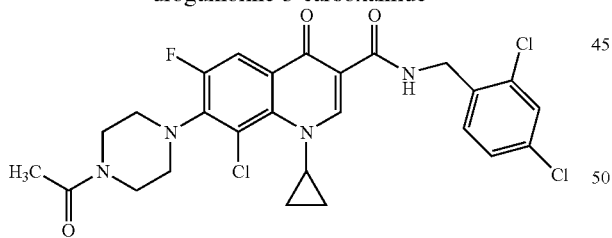

28 µl (0.2 mmol) of triethylamine and 12.8 mg (0.1 mmol) of 1-acetylpiperazine are added to 45.6 mg (0.1 mmol) of 8-chloro-1-cyclopropyl-N-(2,4-dichlorobenzyl)-6,7-difluoro-4-oxo-1,4-dihydroquinoline-3-carboxamide (Example 79A) in 400 µl of DMF. The mixture is stirred for 14 h at 100° C., filtered and purified by preparative LC-MS (Method 12).

In analogy to Example 85 the Examples 86 to 88 listed in the following table are prepared.

| Example No. | Structure | Analytical data<br>LC-MS (Method)/measured value |
|---|---|---|
| 86 | 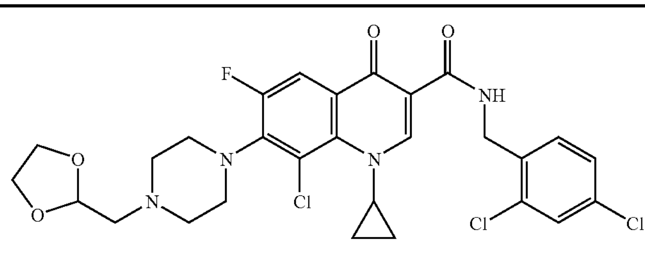 | LC-MS (Method 11): $R_1$ = 1.73 min<br>MS (ES+): m/z = 606 (M + H)$^+$ |

| Example No. | Structure | Analytical data LC-MS (Method)/measured value |
|---|---|---|
| 87 | 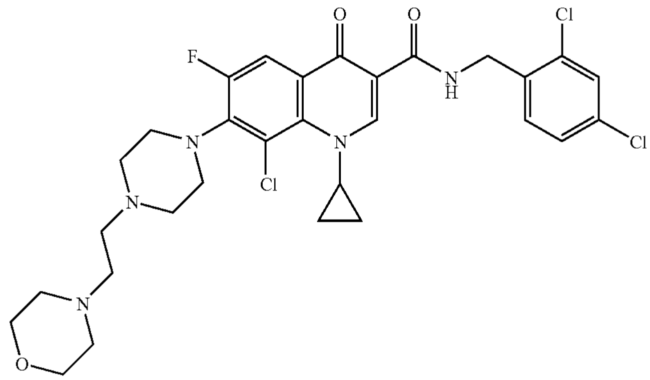 | LC-MS (Method 11): $R_1$ = 1.67 min<br>MS (ES+): m/z = 636 (M + H)$^+$ |
| 88<br>(prepared at 120° C. in DMSO instead of DMF) | | LC-MS (Method 2): $R_1$ = 1.66 min<br>MS (ES+): m/z = 581 (M + H)$^+$ |

Example 89

1-Cyclopropyl-N-(2,4-dichlorobenzyl)-6-fluoro-7-[4-(2-hydroxy-2-methylpropyl)-3-methylpiperazin-1-yl]-8-methoxy-4-oxo-1,4-dihydroquinoline-3-carboxamide hydrochloride

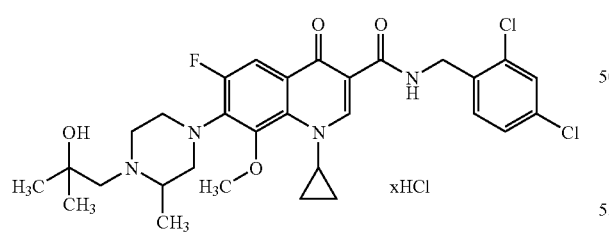

100 mg of 1-cyclopropyl-N-(2,4-dichlorobenzyl)-6-fluoro-8-methoxy-7-(3-methylpiperazine)-4-oxo-1,4-dihydroquinoline-3-carboxamide (free base of Example 49) are stirred with 152 mg of isobutylene oxide (2 eq.) and 75 mg of lithium perchlorate (4 eq.) over night in 10 ml of acetonitrile under reflux. The reaction mixture is purified after cooling directly by preparative RP-HPLC (Method 6).

LC-MS (Method 2): $R_t$=1.62 min, MS (ESI): m/z=605 (M+H)$^+$

Example 90

1-Cyclopropyl-N-(2,4-dichlorobenzyl)-7-[(3RS, 5SR)-3,5-dimethyl-4-(2-hydroxy-2-methylpropyl)piperazin-1-yl]-6-fluoro-8-methoxy-4-oxo-1,4-dihydroquinoline-3-carboxamide hydrochloride

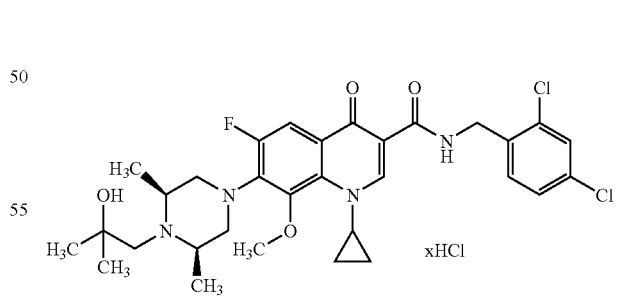

The compound is prepared in analogy to Example 89 from the compound of Example 12 and 1,2-epoxy-2-methylpropane.

LC-MS (Method 3): $R_t$=1.95 min, MS (ES+): m/z=619 (M+H)$^+$

Example 91

1-Cyclopropyl-N-(2,4-dichlorobenzyl)-7-{(3RS,5SR)-4-[(2R)-2,3-dihydroxypropyl]-3,5-dimethylpiperazin-1-yl}-6-fluoro-8-methoxy-4-oxo-1,4-dihydroquinoline-3-carboxamide hydrochloride

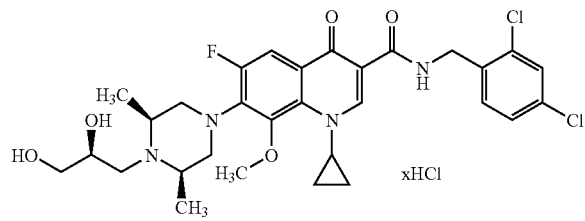

The title compound is prepared in analogy to Example 89 from Example 12 with (2R)-3-butanoyloxy-1,2-epoxypropane and subsequent hydrolysis of the butyrate with 1 equivalent of a 1M lithium hydroxide solution at 70° C. for 1 h. For the work-up the solvent is removed on a rotary evaporator, the residue is adjusted to a neutral pH using 1N hydrochloric acid and buffer pH 7 and extracted with dichloromethane. Purification takes place by RP-HPLC (Method 6).

LC-MS (Method 3): $R_t$=1.77 min, MS (ES+): m/z=621 $(M+H)^+$ $^1$H NMR (400 MHz, DMSO-$d_6$): δ=0.96 (m, 2H), 1.12 (m, 2H), 1.39 (d, 3H), 1.45 (d, 3H), 3.22-3.38 (m, 3H), 3.39-3.78 (m, 7H), 3.80 (s, 3H), 3.85 (m, 1H), 4.02 (m, 1H), 4.11 (m, 1H), 4.58 (d, 2H), 7.38 (d, 1H), 7.42 (dd, 1H), 7.63 (d, 1H), 7.76 (d, 1H), 8.69 (s, 1H), 10.22 (t, 1H), 10.61 (bs, 1H).

In analogy to Example 91 the following Example 92 is prepared.

| Example No. | Structure | Starting material Example No. | Analytical data LC-MS (Method)/ measured values |
|---|---|---|---|
| 92 | 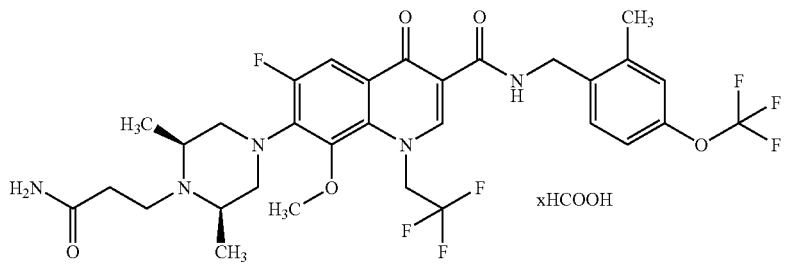 | 12 | LC-MS (Method 3): $R_t$ = 1.86 min MS (ES+): m/z = 621 (M + H)$^+$ |

Example 93

7-[(3RS,5SR)-4-(3-Amino-3-oxopropyl)-3,5-dimethylpiperazin-1-yl]-6-fluoro-8-methoxy-N-[2-methyl-4-(trifluoromethoxy)benzyl]-4-oxo-1-(2,2,2-trifluoroethyl)-1,4-dihydroquinoline-3-carboxamide hydroformate A few drops of acetonitrile are added at room temperature to 55 mg of the compound of Example 52, 18 mg of acrylamide and 35 mg of lithium perchlorate, so that a stirrable suspension results. The mixture is heated to 70° C. over night and left to cool. After the addition of DMSO the whole mixture is separated by preparative HPLC (Method 5). After concentrating the suitable fractions and drying under high vacuum 30 mg (40% of theory) of the title compound are obtained.

LC-MS (Method 1): $R_t$=2.00 min, MS (ES+)=690 $(M+H)^+$.

Example 94

1-Cyclopropyl-7-{(3RS,5SR)-4-[(cyclopropylamino)carbonyl]-3,5-dimethylpiperazin-1-yl}-N-(2,4-dichlorobenzyl)-6-fluoro-8-methoxy-4-oxo-1,4-dihydroquinoline-3-carboxamide

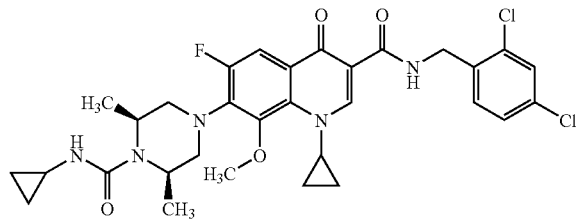

30 μl (24.3 mg, 0.29 mmol) of cyclopropylisocyanate are dissolved in dichloromethan, 80.0 mg (0.146 mmol) of the compound of Example 12 are added and the mixture is stirred over night at room temperature. For the work-up the solvent is removed completely and after fine purification by preparative RP-HPLC (Method 6) 55 mg of the target compound are obtained.

LC-MS (Method 3): $R_t$=2.97 min, MS (ES+)=630 $(M+H)^+$.

$^1$H NMR (400 MHz, DMSO-$d_6$): δ=0.41 (m, 2H), 0.55 (m, 2H), 0.94 (m, 2H), 1.09 (m, 2H), 1.28 (d, 6H), 3.22 (m, 2H), 3.32 (m, 2H), 3.69 (s, 3H), 4.11 (m, 4H), 4.58 (d, 2H), 6.49 (bs, 1H), 7.39 (d, 1H), 7.43 (dd, 1H), 7.63 (d, 1H), 7.74 (d, 1H), 8.68 (s, 1H), 10.25 (t, 1H).

In analogy to Example 94 the following Examples 95 to 97 are prepared.

| Example-No. | Structure | Analytical data<br>LC-MS (Method)/measured value<br>MS (Method)/measured value |
|---|---|---|
| 95 | 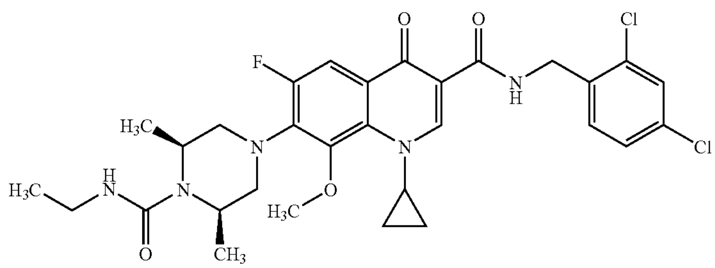 | LC-MS (Method 1): $R_1$ = 2.81 min<br>MS (ES+): m/z = 618 $(M + H)^+$ |
| 96 | 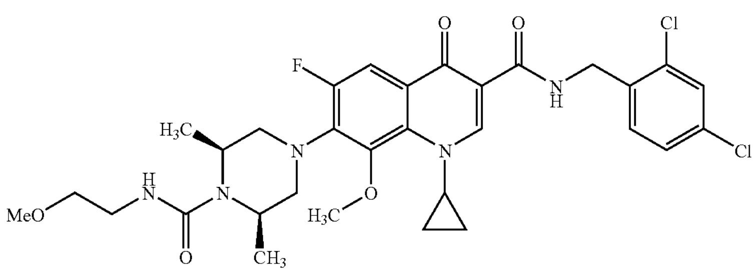 | LC-MS (Method 1): $R_1$ = 2.73 min<br>MS (ES+): m/z = 648 $(M + H)^+$ |
| 97 | 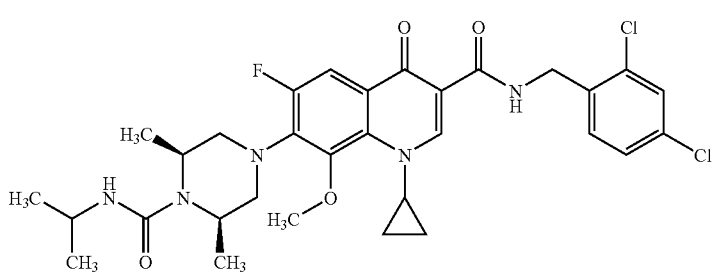 | LC-MS (Method 1): $R_1$ = 2.96 min<br>MS (ES+): m/z = 632 $(M + H)^+$ |

Example 98

6-Fluoro-7-[(3RS,5SR)-4-glycyl-3,5-dimethylpiperazin-1-yl]-8-methoxy-N-(2-methyl-4-trifluoromethoxy)-1-(2,2,2-trifluoroethyl)-4-oxo-1,4-dihydroquinoline-3-carboxamide hydrochloride

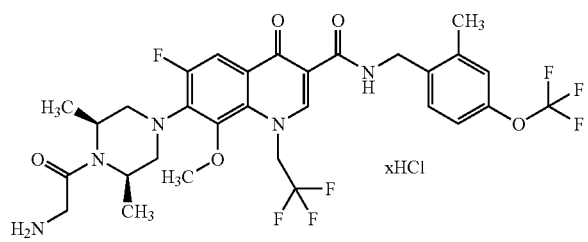

The title compound is prepared in analogy to Example 79 from the compound of Example 87A.

LC-MS (Method 13): $R_t$=3.51 min, MS (ES+): m/z=676 (M+H)$^+$.

Example 99

N-(2,4-Dichlorobenzyl)-7-{(3RS,5SR)-3,5-dimethyl-4-[(5-oxo-4,5-dihydro-1H-1,2,4-triazol-3-yl)methyl]piperazin-1-yl}-6-fluoro-8-methoxy-4-oxo-1-(2,2,2-trifluoroethyl)-1,4-dihydroquinoline-3-carboxamide

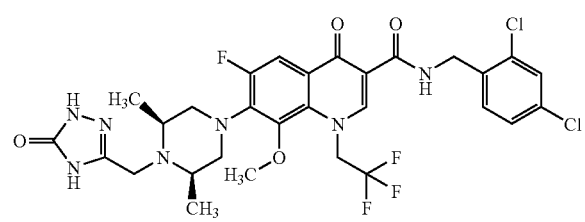

50.0 mg (0.09 mmol) of the free base of the compound of Example are provided in acetonitrile, 17.0 mg (0.13 mmol) of 5-(chloromethyl)-2,4-dihydro-3H-1,2,4-triazol-3-one (for preparation see: Cowden, Camaron J.; Tetrahedron Lett., 41 (44), 2000; 8661-8665), 16.9 mg (0.10 mmol) of potassium iodide and 35.2 mg (0.25 mmol) of potassium carbonate are added and the mixture is stirred over night at 50° C. For the work-up the cooled reaction mixture is filtered through silica gel, which is washed with acetonitrile and dichloromethane/methanol (10/1), the filtrate is removed on a rotary evaporator and from the obtained residue 23 mg (40% of theory) of the product are obtained after fine purification on silica gel 60 (eluent: dichloromethane/ethanol 100/1→50/1→20/1→10/1).

LC-MS (Method 1): $R_t$=2.10 min, MS (ES+): m/z=686 (M+H)$^+$;

$^1$H NMR (400 MHz, DMSO-d$_6$): δ=1.09 (d, 6H), 2.81 (m, 2H), 2.95 (m, 2H), 3.22 (m, 2H), 3.76 (s, 3H), 4.59 (d, 2H), 5.69 (q, 2H), 7.39 (d, 1H), 7.43 (dd, 1H), 7.64 (d, 1H), 7.76 (d, 1H), 8.82 (s, 1H), 10.12 (t, 1H), 11.22 (s, 1H), 11.28 (s, 1H).

Example 100

1-Cyclopropyl-N-(2,4-dichlorobenzyl)-6-fluoro-8-methoxy-7-[3-methyl-4-(2-{[(methylamino)carbonyl]amino}-2-oxoethyl)piperazin-1-yl]-4-oxo-1,4-dihydroquinoline-3-carboxamide hydrochloride

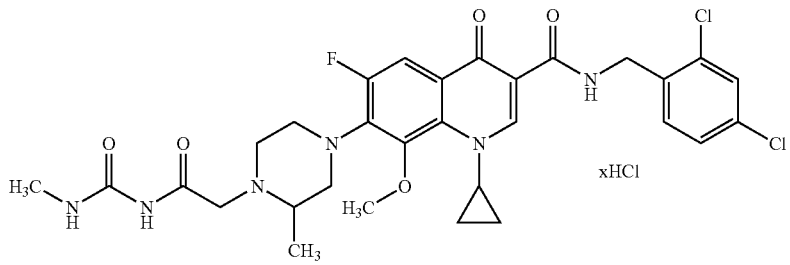

In analogy to the instructions of Example 99 the title compound is obtained from 80.0 mg (0.14 mmol) of the compound of Example 49 and 25.4 mg (0.17 mmol) of 2-chloro-N-[(methylamino)carbonyl]acetamide (for preparation see: patent DE 167138) with 60 mg (62% of theory).

LC-MS (Method 1): $R_t$=2.27 min, MS (ES+): m/z=647 (M+H)$^+$;

$^1$H NMR (300 MHz, DMSO-d$_6$): δ=0.95 (m, 2H), 1.11 (m, 2H), 1.32 (m, 3H), 2.72 (d, 2H), 3.27-3.95 (m, 9H: in there 3.79 (s, 3H)), 4.11 (m, 1H), 4.25 (m, 1H), 4.41 (m, 1H), 4.58 (d, 2H), 7.38 (d, 1H), 7.43 (dd, 1H), 7.64 (d, 1H), 7.71-7.98 (m, 2H: in there 7.78 (d, 1H)), 8.79 (s, 1H), 10.22 (t, 1H), 10.81 (s, 1H).

In analogy to Example 91 the following Examples 101 and 102 are prepared.

| Example No. | Structure | Starting material Example No. | Analytical data LC-MS (Method)/ measured values NMR-spectrum |
|---|---|---|---|
| 101 | (structure with x HCOOH) | 52 | LC-MS (Method 3):<br>$R_t$ = 1.98 min<br>MS (ES+): m/z = 693 (M + H)$^+$<br>$^1$H NMR (400 MHz, CDCl$_3$):<br>δ = 1.33(d, 3H), 2.40(s, 3H), 2.85(br. d, 1H), 3.05-3.22(m, 3H), 3.28-3.47(m, 4H), 3.57 (dd, 1H), 3.76(dd, 1H), 3.81(s, 3H), 3.98(m, 1H), 4.52(d, 2H), 5.23(q, 2H), 7.02(d, 1H), 7.03(s, 1H), 7.37(d, 1H), 7.91(d, 1H), 8.25(s, 1H, HCOOH), 8.60(s, 1H), 10.2(t, 1H). |
| 102 | (structure with x HCOOH) | 52 | LC-MS (Method 3):<br>$R_t$ = 1.97 min<br>MS (ES+): m/z = 693 (M + H)$^+$ |

B. Assessment of the Physiological Activity

The in vitro effect of the compounds of the invention can be shown in the following assays:

Anti-HCMV (Anti-human Cytomegalovirus) Cytopathogenicity Tests

The test compounds are employed as 50 millimolar (mM) solutions in dimethyl sulfoxide (DMSO). Ganciclovir®, Foscarnet® and Cidofovir® are used as reference compounds. After the addition of 2 µl of the 50, 5, 0.5 and 0.05 mM DMSO stock solutions respectively to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. 150 µl of a suspension of 1×10$^4$ cells (human prepuce fibroblasts [NHDF]) are then pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% CO$_2$ for 6 days, i.e. until all the cells in the virus controls are infected (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (plaque multiplier from Technomara).

The following data can be obtained from the test plates:
- $CC_{50}$ (NHDF)=substance concentration in µM at which no visible cytostatic effects on the cells are evident by comparison with the untreated cell control;
- $EC_{50}$ (HCMV)=substance concentration in µM which inhibits the CPE (cytopathic effect) by 50% compared with the untreated virus control;
- SI (selectivity index)=$CC_{50}$ (NHDF)/$EC_{50}$ (HCMV).

Representative in vitro data for the effects of the compounds of the invention are shown in Table A:

TABLE A

| Example No. | NHDF $CC_{50}$ [µM] | HCMV $EC_{50}$ [µM] | SI HCMV |
|---|---|---|---|
| 1 | 2.5 | 0.20 | 12.5 |
| 5 | 6.0 | 0.23 | 26 |
| 8 | 7.7 | 0.19 | 41 |
| 16 | 7.8 | 0.10 | 78 |
| 22 | 8.4 | 0.38 | 22 |
| 24 | 4.7 | 0.25 | 19 |
| 28 | 6.1 | 0.10 | 63 |
| 31 | 4.5 | 0.032 | 151 |
| 34 | 8.4 | 0.019 | 442 |
| 35 | 4.8 | 0.0365 | 138 |
| 38 | 11.0 | 0.053 | 208 |
| 40 | 11.0 | 0.11 | 100 |
| 45 | 2.4 | 0.077 | 31 |
| 51 | 5.3 | 0.011 | 482 |
| 52 | 7.7 | 0.019 | 405 |
| 53 | 4.3 | 0.01 | 430 |
| 54 | 21.0 | 0.0085 | 2471 |
| 68 | 24.0 | 0.002 | 12000 |
| 74 | 2.6 | 0.092 | 28 |
| 79 | 7.7 | 0.053 | 145 |
| 92 | 5.3 | 0.031 | 171 |

The suitability of the compounds of the invention for the treatment of HCMV infections can be shown in the following animal model:

HCMV Xenograft Gelfoam® Model

Animals:

5-6-week old immunodeficient mice (16-20 g), Fox Chase SCID.NOD or NOD.CB17-Prkdc/J, are purchased from commercial breeders (Taconic M&B, Denmark; Jackson, USA). The animals are kept under sterile conditions (including bedding and feed) in isolators.

Virus Growing:

Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 20% foetal calf serum (FCS) (v/v), 1% glutamine (v/v), 1% Pen/Strep (v/v) with 10% DMSO at −80° C. After serial ten-fold dilutions of the virus-infected cells, the titer is determined on 24-well plates of confluent NHDF cells after fixing and staining with a Giemsa formaldehyde solution.

Preparation of the Sponges, Transplantation, Treatment and Evaluation:

Collagen sponges 1×1×1 cm in size (Gelfoam®; Peasel & Lorey, order no. 407534; K. T. Chong et al., *Abstracts of 39th Interscience Conference on Antimicrobial Agents and Chemotherapy* (1999) p. 439) are initially wetted with phosphate-buffered saline (PBS), the trapped air bubbles are removed by degassing, and then stored in MEM, 10% FCS (v/v), 1% glutamine (v/v), 1% Pen/Strep (v/v). $1 \times 10^6$ virus-infected NHDF cells (infection with HCMV Davis or HCMV AD169 M.O.I=0.03) are detached 3 hours after infection and added dropwise in 20 µl of MEM, 10% FCS (v/v), 1% glutamine (v/v), 1% Pen/Strep (v/v) to a moist sponge. The sponges are incubated for 3-4 hours to allow the cells to adhere. Then, following the addition of medium (MEM, 10% FCS) (v/v), 1% glutamine (v/v), 1% Pen/Strep (v/v)), the sponges are incubated overnight. For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue or clips. 4-6 hours after the transplantation, the mice can be treated for the first time (one treatment is given on the day of the operation). On subsequent days, oral treatment with the substance is carried out three times a day (7.00 h and 14.00 h and 19.00 h), twice a day (8 h and 18 h) or once a day (9 h) over a period of 8 days. The daily dose is for example 1 or 3 or 10 or 30 or 100 mg/kg of body weight, the volume administered is 10 ml/kg of body weight. The substances are formulated in the form of a 0.5% Tylose suspension/PBS with 2% DMSO or another suitable mixture aiding solubility of the substances, e.g. 2% ethanol, 2.5% Solutol, 95.5% PBS. 10 days after transplantation and about 16 hours after the last administration of substance, the animals are painlessly sacrificed and the sponge is removed. The virus-infected cells are released from the sponge by collagenase digestion (330 U/1.5 ml) and stored in the presence of MEM, 10% FCS (v/v), 1% glutamine (v/v), 1% Pen/Strep (v/v), 10% DMSO at −140° C. Evaluation takes place after serial ten-fold dilutions of the virus-infected cells by determining the titer on 24-well plates of confluent NHDF cells after fixing and staining with a Giemsa formaldehyde solution. The number of infected cells or infectious virus particles (infectious centre assay) after the substance treatment compared with the placebo-treated control group is determined. Statistical evaluation takes place by suitable computer programs, such as GraphPad Prism.

C. Exemplary Embodiments of Pharmaceutical Compositions

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension Which Can Be Administered Orally:

Composition:

1000 mg of the compound of Example 1, 1000 mg of ethanol (96%), 400 mg of Rhodigel (xanthan gum, FMC, Pennsylvania, USA) and 99 g of water.

10 ml of oral suspension are equivalent to a single dose of 100 mg of the compound of the invention.

Production:

The Rhodigel is suspended in ethanol, and the active ingredient is added to the suspension. The water is added while stirring. The mixture is stirred for about 6 h until the swelling of the Rhodigel is complete.

Solution Which Can Be Administered Intravenously:

Composition:

10-500 mg of the compound of Example 1, 15 g of polyethylene glycol 400 and 250 g of water for injections.

Production:

The compound of Example 1 is dissolved together with polyethylene glycol 400 in the water with stirring. The solution is sterilized by filtration (pore diameter 0.22 µm) and dispensed under aseptic conditions into heat-sterilized infusion bottles. The latter are closed with infusion stoppers and crimped caps.

The invention claimed is:

1. A compound of formula

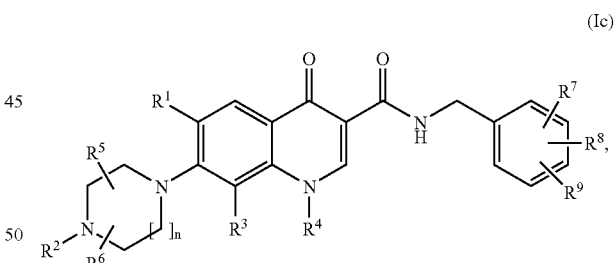

in which n represents a number 1 or 2, $R^1$ represents fluorine, chlorine or trifluoromethyl, $R^2$ represents hydrogen or $C_1$-$C_6$-alkyl, whereby alkyl can be substituted with 1 to 2 substituents, whereby the substituents are selected independently of one another from the group consisting of hydroxy, aminocarbonyl, $C_1$-$C_6$-alkoxy, $C_1$-$C_6$-alkylcarbonyl, $C_1$-$C_6$-alkylaminocarbonyl, $C_3$-$C_8$-cycloalkylaminocarbonyl, $C_1$-$C_6$-alkylaminocarbonylaminocarbonyl, $C_1$-$C_6$-alkylsulfonylaminocarbonyl, phenoxy, morpholin-2-yl, morpholin-3-yl, morpholin-4-yl, morpholin-2-ylcarbonyl, morpholin-3-ylcarbonyl, morpholin-4-ylcarbonyl, piperidin-1-ylcarbonyl, piperidin-2-ylcarbonyl, piperidin-3-ylcarbonyl, piperidin-4-ylcarbonyl, pyrrolidin-2-ylcarbonyl and pyrrolidin-3-ylcarbonyl, wherein alkoxy in turn can be substituted with a substituent, whereby the substituent is selected from the group consisting of hydroxyl, and phenyl, or $R^2$ represents $C_1$-$C_6$-alkylcarbonyl, optionally once $C_1$-$C_4$-alkoxy-substituted $C_1$-$C_6$-alkylaminocarbonyl, or $C_3$-$C_8$-cycloalkylaminocarbonyl, whereby alkylcarbonyl can be substituted with a substituent, whereby the substituent is selected from the group consisting of amino, $C_1$-$C_6$-alkylamino and $C_3$-$C_8$-cycloalkylamino, $R^3$ represents halogen, cyano, methoxy, monofluoromethoxy, difluoromethox: trifluoromethoxy or ethynyl, $R^4$ represents $C_1$-$C_6$-alkyl or $C_3$-$C_8$-cycloalkyl, whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl, and whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl, $R^5$ and $R^6$ independently of one another represent hydrogen, methyl or ethyl, $R^7$ and $R^8$ independently of one another represent halogen, hydroxy, cyano, trifluoromethyl, monofluoromethoxy, difluoromethoxy, trifluoromethoxy, $C_3$-alkyl or $C_1$-$C_3$-alkoxy, $R^9$ represents hydrogen, halogen, hydroxy, cyano, trifluoromethyl, mono-fluoromethoxy, difluoromethoxy, trifluoromethoxy, $C_1$-$C_3$-Alkyl or $C_1$-$C_3$-alkoxy, or one of its salts.

2. The compound of claim 1, corresponding to formula

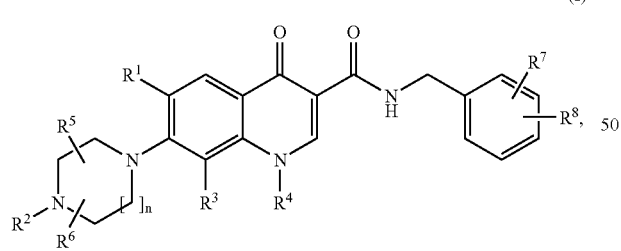

(I)

in which n represents a number 1 or 2, $R^1$ represents fluorine, chlorine or trifluoromethyl, $R^2$ represents hydrogen or $C_1$-$C_6$-alkyl, whereby alkyl can be substituted with 1 to 2 substituents, whereby the substituents are selected independently of one another from the group consisting of hydroxy, aminocarbonyl, $C_1$-$C_6$-alkoxy, $C_1$-$C_6$-alkylcarbonyl, $C_1$-$C_6$-alkylaminocarbonyl, $C_3$-$C_8$-cycloalkylaminocarbonyl, $C_1$-$C_6$-alkylsulfonyl-aminocarbonyl, phenoxy, morpholin-2-yl, morpholin-3-yl, morpholin-4-yl, morpholin-2-ylcarbonyl, morpholin-3-ylcarbon, morpholin-4-ylcarbonyl, piperidin-1-ylcarbonyl, piperidin-2-ylcarbonyl, piperidin-3-ylcarbonyl, piperidin-4-ylcarbonyl, pyrrolidin-2-ylcarbonyl and pyrrolidin-3-ylcarbonyl, wherein alkoxy in turn can be substituted with a substituent, whereby the substituent is selected from the group consisting of hydroxy, and phenyl, or $R^2$ represents $C_1$-$C_6$-alkylcarbonyl, optionally once $C_1$-$C_4$-alkoxy-substituted $C_1$-$C_6$-alkylaminocarbonyl, or $C_3$-$C_8$-cycloalkylaminocarbonyl, whereby alkylcarbonyl can be substituted with a substituent, whereby the substituent is selected from the group consisting of amino, $C_1$-$C_6$-alkylamino, and $C_3$-$C_8$-cycloalkylamino, $R^3$ represents halogen, cyano, methoxy, monofluoromethoxy, difluoromethoxy, trifluoromethoxy or ethynyl, $R^4$ represents $C_1$-$C_6$-alkyl or $C_3$-$C_8$-cycloalkyl, whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl, and whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl, $R^5$ and $R^6$ independently of one another represent hydrogen, methyl or ethyl, $R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy, or one of its salts.

3. The compound of claim 2, corresponding to formula

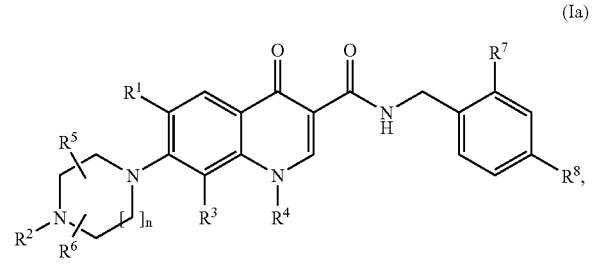

(Ia)

in which n represents a number 1 or 2, $R^1$ represents fluorine, $R^2$ represents hydrogen or $C_1$-$C_6$-alkyl, whereby alkyl can be substituted with 1 or 2 substituents, whereby the substituents are selected independently of one another from the group consisting of hydroxy, $C_1$-$C_6$-alkoxy, morpholin-2-yl, morpholin-3-yl, morph-olin-4-yl, morpholin-2-ylcarbonyl, morpholin-3-ylcarbonyl, morpholin-4-ylcarbonyl, piperidin-1-ylcarbonyl, piperidin-2-ylcarbonyl, piperidin-3-ylcarbonyl, piperidin-4-ylcarbonyl, pyrrolidin-2-ylcarbonyl and pyrrolidin-3-ylcarbonyl,
wherein alkoxy in turn can be substituted with a substituent, whereby the substituent is hydroxy, or $R^2$ represents $C_1$-$C_6$-alkylcarbonyl,
whereby alkylcarbonyl is substituted with an amino substituent, $R^3$ represents fluorine, chlorine, methoxy, monofluoromethoxy, difluoromethoxy, trifluoromethoxy or ethynyl, $R^4$ represents $C_1$-$C_4$-alkyl or $C_3$-$_5$-cycloalkyl,
whereby alkyl can be substituted with 1 to 3 substituents, whereby the substituents are selected independently of one another from the group consisting of hydroxy and $C_1$-$C_3$-alkoxy, and
whereby cycloalkyl can be substituted with 1 to 3 substituents, whereby the substituents are selected independently of one another from the group consisting of halogen, hydroxy, trifluoromethyl, $C_1$-$C_3$-alkyl and $C_1$-$C_3$-alkoxy, $R^5$ and $R^6$ independently of one another represent hydrogen or methyl, $R^7$ and $R^8$ independently of one another represent fluorine, chlorine, cyano, trifluoromethyl, difluoromethoxy, trifluoromethoxy, $C_1$-$C_3$-alkyl or $C_1$-$C_3$-alkoxy.

4. The compound of claim 2, corresponding to formula

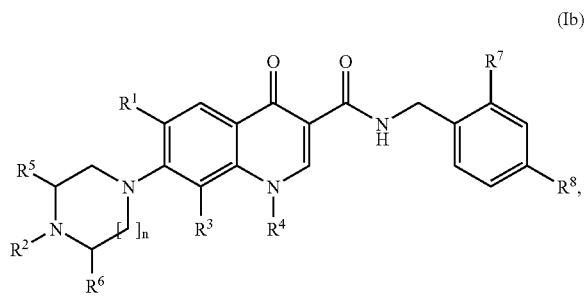

(Ib)

in which
n represents a number 1 or 2,
$R^1$ represents fluorine,
$R^2$ represents hydrogen or $C_1$-$C_3$-alkyl,
whereby alkyl can be substituted with 1 or 2 substituents, whereby the substituents are selected independently of one another from the group consisting of hydroxy, morpholin-2-ylcarbonyl, morpholin-3-ylcarbonyl, morpholin-4-ylcarbonyl, piperidin-1-ylcarbonyl, piperidin-2-ylcarbonyl, piperidin-3-ylcarbonyl, piperidin-4-ylcarbonyl, pyrrolidin-2-ylcarbonyl, pyrrolidin-3-ylcarbonyl and $C_1$-$C_3$-alkoxy which is optionally substituted with a hydroxy substituent, or $R^2$ represents $C_1$-$C_4$-alkylcarbonyl,
whereby alkylcarbonyl is substituted with an amino substituent, $R^3$ represents chlorine, methoxy, difluoromethoxy or trifluoromethoxy, $R^4$ represents methyl, ethyl or cyclopropyl,
whereby ethyl can be substituted with 1 to 3 fluorine substituents, and
whereby cyclopropyl can be substituted with 1 to 2 fluorine substituents, $R^5$ and $R^6$ independently of one another represent hydrogen or methyl, $R^7$ and $R^8$ independently of one another represent chlorine, trifluoromethyl, trifluoromethoxy or methyl.

5. A medicament comprising a compound of claim 1 in combination with an inert, non-toxic, pharmaceutically acceptable excipient.

6. A method of controlling an infection with a virus selected from the group consisting of the human cytomegalovirus (HCMV) and other representatives of the group of herpes viridae by administering an antivirally effective amount of at least one compound of claim 1 to a human or animal in need thereof.

7. A method of controlling an infection with a virus selected from the group consisting of the human cytomegalovirus (HCMV) and other representatives of the group of herpes viridae by administering an antivirally effective amount of at least one medicament of claim 5 to a human or animal in need thereof.

8. A medicament comprising a compound of claim 2 in combination with an inert, non-toxic, pharmaceutically acceptable excipient.

9. A medicament comprising a compound of claim 3 in combination with an inert, non-toxic, pharmaceutically acceptable excipient.

10. A medicament comprising a compound of claim 4 in combination with an inert, non-toxic, pharmaceutically acceptable excipient.

11. A method of controlling an infection with a virus selected from the group consisting of the human cytomegalovirus (HCMV) and other representatives of the group of herpes viridae by administering an antivirally effective amount of at least one medicament of claim 8 to a human or animal in need thereof.

12. A method of controlling an infection with a virus selected from the group consisting of the human cytomegalovirus (HCMV) and other representatives of the group of herpes viridae by administering an antivirally effective amount of at least one medicament of claim 9 to a human or animal in need thereof.

13. A method of controlling an infection with a virus selected from the group consisting of the human cytomegalovirus (HCMV) and other representatives of the group of herpes viridae by administering an antivirally effective amount of at least one medicament of claim 10 to a human or animal in need thereof.

14. A method of controlling an infection with a virus selected from the group consisting of the human cytomegalovirus (HCMV) and other representatives of the group of herpes viridae by administering an antivirally effective amount of at least one compound of claim 2 to a human or animal in need thereof.

15. A method of controlling an infection with a virus selected from the group consisting of the human cytomegalovirus (HCMV) and other representatives of the group of herpes viridae by administering an antivirally effective amount of at least one compound of claim 3 to a human or animal in need thereof.

16. A method of controlling an infection with a virus selected from the group consisting of the human cytomegalovirus (HCMV) and other representatives of the group of herpes viridae by administering an antivirally effective amount of at least one compound of claim 4 to a human or animal in need thereof.

* * * * *

UNITED STATES PATENT AND TRADEMARK OFFICE
CERTIFICATE OF CORRECTION

PATENT NO. : 7,867,992 B2  
APPLICATION NO. : 11/655589  
DATED : January 11, 2011  
INVENTOR(S) : Holger Zimmermann et al.

Page 1 of 1

It is certified that error appears in the above-identified patent and that said Letters Patent is hereby corrected as shown below:

<u>On the Title page, item [75]</u>:

First column, line 12, "Grevenbroich" should be -- Neuss --.

Signed and Sealed this

Twenty-sixth Day of July, 2011

David J. Kappos  
*Director of the United States Patent and Trademark Office*